(12) United States Patent
Lee et al.

(10) Patent No.: US 9,850,196 B2
(45) Date of Patent: *Dec. 26, 2017

(54) COMPOUNDS HAVING NEGATIVE OPTICAL DISPERSION, NEGATIVE OPTICAL DISPERSION COMPOSITION COMPRISING THE COMPOUNDS, AND OPTICALLY ANISOTROPIC BODY COMPRISING THE COMPOSITION

(71) Applicant: LG CHEM, LTD., Seoul (KR)

(72) Inventors: Min Hyung Lee, Daejeon (KR); Sung-Ho Chun, Daejeon (KR); Kyung Chang Seo, Daejeon (KR); Jung Hyun Kim, Daejeon (KR); Mi Ra Hong, Daejeon (KR); Hyeong Bin Jang, Daejeon (KR); Jeong Wook Mun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/913,589

(22) PCT Filed: Sep. 19, 2014

(86) PCT No.: PCT/KR2014/008751
§ 371 (c)(1),
(2) Date: Feb. 22, 2016

(87) PCT Pub. No.: WO2015/046826
PCT Pub. Date: Apr. 2, 2015

(65) Prior Publication Data
US 2016/0200662 A1   Jul. 14, 2016

(30) Foreign Application Priority Data

Sep. 30, 2013 (KR) .................. 10-2013-0116533
Sep. 18, 2014 (KR) .................. 10-2014-0124468

(51) Int. Cl.
| C07C 69/76 | (2006.01) |
| C07C 69/86 | (2006.01) |
| C07C 69/94 | (2006.01) |
| G02B 5/00 | (2006.01) |
| C09K 19/30 | (2006.01) |
| G02B 1/08 | (2006.01) |
| G02B 5/30 | (2006.01) |
| C09K 19/38 | (2006.01) |
| C09K 19/04 | (2006.01) |

(52) U.S. Cl.
CPC .............. C07C 69/86 (2013.01); C07C 69/94 (2013.01); C09K 19/3068 (2013.01); C09K 19/3852 (2013.01); G02B 1/08 (2013.01); G02B 5/00 (2013.01); G02B 5/3083 (2013.01); C07C 2601/14 (2017.05); C09K 2019/0448 (2013.01); C09K 2019/0496 (2013.01)

(58) Field of Classification Search
CPC ..... C07C 2101/14; C07C 69/86; C07C 69/94; C07C 2601/14; C09K 19/3068; C09K 19/3852; C09K 2019/0448; C09K 2019/0496; G02B 5/00; G02B 5/3083; G02B 1/08

See application file for complete search history.

(56) References Cited

U.S. PATENT DOCUMENTS

| 2007/0298191 A1* | 12/2007 | Yamahara ......... C08F 222/1006 428/1.1 |
| 2009/0159857 A1* | 6/2009 | Uehira ................ C07D 339/06 252/585 |
| 2010/0045901 A1* | 2/2010 | Uehira ................ C07D 277/64 349/75 |
| 2015/0115199 A1* | 4/2015 | Choi ................ G02F 1/133784 252/299.61 |

FOREIGN PATENT DOCUMENTS

| JP | 2000-169403 A | 6/2000 |
| JP | 2001-11459 A | 1/2001 |
| JP | 2007-70285 A | 3/2007 |
| JP | 2008-110948 A | 5/2008 |
| KR | 10-2006-0119879 A | 11/2006 |
| KR | 10-2010-0016054 A | 2/2010 |
| KR | 10-2010-0130179 A | 12/2010 |
| KR | 10-2011-0043776 A | 4/2011 |
| TW | 2009-07029 A | 2/2009 |
| TW | 2009-38613 A | 9/2009 |
| TW | 2010-12904 A | 4/2010 |
| WO | 2008/119427 A1 | 10/2008 |
| WO | 2011/050896 A1 | 5/2011 |
| WO | WO2011050896 * | 5/2011 |
| WO | WO2012/020643 * | 2/2012 |
| WO | 2013/157888 A1 | 10/2013 |

OTHER PUBLICATIONS

Carsten Tschierske, et al.: "Definitionen von Grundbegriffen mit Bezug zu nieder-molekularen und polymeren Fluessigkristallen", Angew. Chem. 2004, 116, pp. 6340-6368 and English Reference, C. Noel et al.: "Definitions of Basic Terms Relating to Low-Molecular-Mass and Polymer Liquid Crystals", Pure Appl. Chem. vol. 73, No. 5, 2001, pp. 845-895.

* cited by examiner

Primary Examiner — Yevegeny Valenrod
Assistant Examiner — Blaine G Doletski
(74) Attorney, Agent, or Firm — Dentons US LLP

(57) ABSTRACT

The present invention relates to a reverse wavelength dispersion compound, a reverse wavelength dispersion composition including the same, and an optically anisotropic body including the same. The reverse wavelength dispersion composition according to the present invention can provide a stronger and more stable reverse wavelength dispersion property, and makes it possible to provide an optically anisotropic body having excellent optical properties.

3 Claims, 20 Drawing Sheets

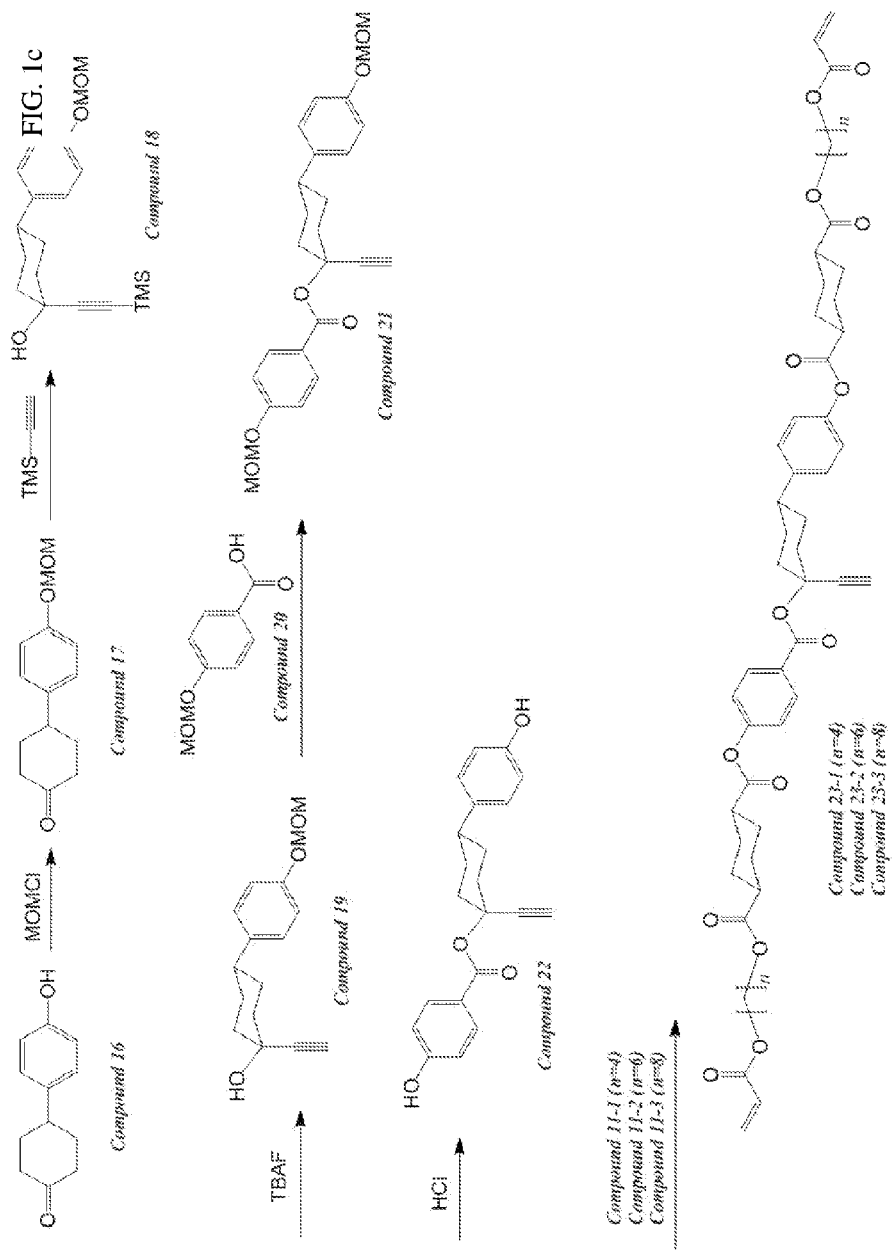

COMPOUNDS HAVING NEGATIVE OPTICAL DISPERSION, NEGATIVE OPTICAL DISPERSION COMPOSITION COMPRISING THE COMPOUNDS, AND OPTICALLY ANISOTROPIC BODY COMPRISING THE COMPOSITION

This application is a National Stage Entry of International Application No. PCT/KR2014/008751, filed on Sep. 19, 2014, and claims the benefit of and priority to Korean Application No. 10-2013-0116533, filed on Sep. 30, 2013, and Korean Application No. 10-2014-0124468, filed on Sep. 18, 2014, all of which are incorporated herein by reference in their entirety for all purposes as if fully set forth herein.

TECHNICAL FIELD

The present invention relates to a reverse wavelength dispersion compound, a reverse wavelength dispersion composition including the same, and an optically anisotropic body including the same.

BACKGROUND OF ART

As the share of liquid crystal displays (LCD) increases in the display field, there is a rising interest in organic light emitting diode (OLED) displays which are mentioned as a next generation display.

The OLED displays are spotlighted as a future display because they are superior in various aspects such as thickness, power consumption, response speed, viewing angle, and so on to LCDs, and they are applicable to various transparent products and flexible goods.

However, OLEDs have limits in enlargement because they have a short life and low emission efficiency, and particularly, they have a demerit that it is hard to realize perfect black because of interference by external light.

In order to realize more perfect black, a method for minimizing the interference by external light by using two sheets of polarizing films for an OLED display was suggested. The method of using two sheets of polarizing films is relatively simple but there are some problems that clarity of display may be affected and the production cost increases.

According to this, various methods for minimizing the interference by external light such as a method of using a reverse wavelength dispersion film instead of said polarizing film and so on are being suggested, but the effects are insufficient thus far.

DETAILED DESCRIPTION OF THE INVENTION

Technical Problem

It is an aspect of the present invention to provide a reverse wavelength dispersion compound which can provide a stronger and more stable reverse wavelength dispersion property.

It is another aspect of the present invention to provide a reverse wavelength dispersion composition and an optically anisotropic body including the compound.

Technical Solution

According to the present invention, a reverse wavelength dispersion compound represented by the following Chemical Formula 1 is provided.

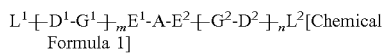

In Chemical Formula 1,

A is a $C_5$-$C_8$ non-aromatic carbocyclic or heterocyclic group or a $C_6$-$C_{20}$ aromatic or heteroaromatic group;

$E^1$, $E^2$, $D^1$, and $D^2$ are independently a single bond or a divalent connecting group, respectively;

$L^1$ and $L^2$ are independently —H, —F, —Cl, —Br, —I, —CN, —NC, —NCO, —OCN, —SCN, —C(=O)NR$^1$R$^2$, —C(=O)R$^1$, —O—C(=O)R$^1$, —NH$_2$, —SH, —SR$^1$, —SO$_3$H, —SO$_2$R$^1$, —OH, —NO$_2$, —CF$_3$, —SF$_3$, a substituted or non-substituted silyl, a $C_1$-$C_{40}$ substituted or non-substituted carbyl or hydrocarbyl, or —S$_p$—P, respectively, wherein at least one of said $L^1$ and $L^2$ is —S$_p$—P, said P is a polymerizable group, said $S_p$ is a spacer group or a single bond, and each of $R^1$ and $R^2$ is independently —H or a $C_1$-$C_{12}$ alkyl;

m and n are independently an integer of 1 to 5, wherein if said m or n is 2 or more, each repeating unit of -($D^1$-$G^1$)- or -($G^2$-$D^2$)- repeating twice or more may be the same as or different from each other; and $G^1$ and $G^2$ are independently a $C_5$-$C_8$ non-aromatic carbocyclic or heterocyclic group or a $C_6$-$C_{20}$ aromatic or heteroaromatic group, wherein at least one of said $G^1$ and $G^2$ is the carbocyclic or heterocyclic group and any one of hydrogens included in the carbocyclic or heterocyclic group is substituted by a group represented by the following Chemical Formula 2.

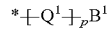 [Chemical Formula 2]

In Chemical Formula 2, p is an integer of 1 to 10, wherein if said p is 2 or more, each repeating unit of -($Q^1$)- repeating twice or more may be the same as or different from each other, $Q^1$ is independently a divalent group selected from the group consisting of —C≡C—, —CY$^1$=CY$^2$—, and a $C_6$-$C_{20}$ substituted or non-substituted aromatic or heteroaromatic group, and said $Y^1$ and $Y^2$ are independently —H, —F, —Cl, —CN, or —R$^1$, and $B^1$ is —H, —F, —Cl, —Br, —I, —CN, —NC, —NCO, —OCN, —SCN, —C(=O)NR$^1$R$^2$, —C(=O)R$^1$, —NH$_2$, —SH, —SR$^1$, —SO$_3$H, —SO$_2$R$^1$, —OH, —NO$_2$, —CF$_3$, —SF$_3$, a polymerizable group (said P defined in Chemical Formula 1), a $C_2$-$C_6$ alkenyl group, a $C_2$-$C_6$ alkynyl group, a $C_2$-$C_4$ acyl group, a $C_2$-$C_6$ alkynylene group of which the end is connected with a $C_2$-$C_4$ acyl group, a $C_1$-$C_5$ alcohol group, or a $C_1$-$C_{12}$ alkoxy group, wherein said $R^1$ and $R^2$ are independently —H or a $C_1$-$C_{12}$ alkyl.

Furthermore, according to the present invention, an optically anisotropic body that is obtained from the composition including said reverse wavelength dispersion compound and satisfies the following Equations I and II is provided.

$$\Delta n_{(450\ nm)}/\Delta n_{(550\ nm)} < 1.0 \quad \text{(Equation I)}$$

$$\Delta n_{(650\ nm)}/\Delta n_{(550\ nm)} > 1.0 \quad \text{(Equation II)}$$

In Equations I and II, Δn(λ) means specific birefringent index at wavelength λ.

Hereinafter, the reverse wavelength dispersion compound according to the embodiments of the present invention and the optically anisotropic body obtained from the composition including the same are explained.

Prior to this, technical terms in the present specification are only for mentioning specific embodiments, and they are not intended to restrict the present invention unless there is a particular mention to the contrary. Further, singular expressions used herein may include the plural expressions unless they are differently expressed contextually.

The meaning of the term "include" used in the specification embodies specific characteristics, areas, integers, steps, actions, elements, or components, and does not exclude other specific characteristics, areas, integers, steps, actions, elements, or components.

Meanwhile, "reverse wavelength dispersion compound" means a compound showing a liquid crystalline property and reverse wavelength dispersity by itself or by being polymerized or cross-linked with an arbitrary liquid crystalline compound and making the liquid crystalline compound show reverse wavelength dispersity even though it does not show the liquid crystalline property by itself. Specifically, it is possible to obtain a polymerized compound in which the oriented structure of liquid crystal molecules is fixed by aligning the reverse wavelength dispersion compound or the composition including the reverse wavelength dispersion compound and the liquid crystal compound (for example, a reactive mesogenic compound having a liquid crystalline property) to the liquid crystal state and exposing the same to active energy rays such as UV rays. The polymerized compound obtained in this way shows anisotropy in the physical properties such as birefringent index, permittivity, magnetic susceptibility, modulus, coefficient of thermal expansion, and so on, and thus it can be applied to optically anisotropic bodies such as retardation plates, polarization plates, polarization prisms, brightness enhancing films, covering materials of optical fibers, and so on, for example.

Further, "specific birefringent index" means a phase difference value at a wavelength ($\lambda$) of transmitted light that goes through the optical film, and it may be represented by $\Delta n(\lambda)$.

In addition, "mesogenic group" means a group having the ability to induce the liquid crystalline behavior.

Additionally, "spacer group" has been known to a person skilled in the art to which the present invention pertains, and for example, it is disclosed in the literature [C. Tschierske, G. Pelzl, S. Diele, Angew. Chem. 2004, 116, 6340-6368]. Said spacer group is designated as a flexible organic group that connects the mesogenic group and the polymerizable group.

Further, "carbyl group" means an arbitrary monovalent or polyvalent organic radical residue that includes one or more carbon atoms (for example, —C≡C—) without an arbitrary non-carbon atom, or one or more carbon atoms (for example, carbonyl) selectively combined with one or more non-carbon atoms (for example, N, O, S, P, and Si), and "hydrocarbyl group" means a carbyl group additionally including one or more H atoms and one or more selective heteroatoms (for example, N, O, S, P, and Si).

I. Reverse Wavelength Dispersion Compound

According to one embodiment of the present invention, the reverse wavelength dispersion compound represented by the following Chemical Formula 1 is provided.

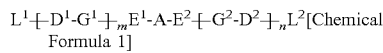   [Chemical Formula 1]

In Chemical Formula 1,

A is a $C_5$-$C_8$ non-aromatic carbocyclic or heterocyclic group or a $C_6$-$C_{20}$ aromatic or heteroaromatic group;

$E^1$, $E^2$, $D^1$, and $D^2$ are independently a single bond or a divalent connecting group;

$L^1$ and $L^2$ are independently —H, —F, —Cl, —Br, —I, —CN, —NC, —NCO, —OCN, —SCN, —C(=O)NR$^1$R$^2$, —C(=O)R$^1$, —O—C(=O)R$^1$, —NH$_2$, —SH, —SR$^1$, —SO$_3$H, —SO$_2$R$^1$, —OH, —NO$_2$, —CF$_3$, —SF$_3$, a substituted or non-substituted silyl, a $C_1$-$C_{40}$ substituted or non-substituted carbyl or hydrocarbyl, or —S$_p$—P, wherein at least one of said $L^1$ and $L^2$ is —S$_p$—P, said P is a polymerizable group, said S$_p$ is a spacer group or a single bond, and each of $R^1$ and $R^2$ is independently —H or a $C_1$-$C_{12}$ alkyl;

m and n are independently an integer of 1 to 5, wherein if said m or n is 2 or more, each repeating unit of -($D^1$-$G^1$)- or -($G^2$-$D^2$)- repeating twice or more may be the same as or different from each other;

$G^1$ and $G^2$ are independently a $C_5$-$C_8$ non-aromatic carbocyclic or heterocyclic group or a $C_6$-$C_{20}$ aromatic or heteroaromatic group, wherein at least one of said $G^1$ and $G^2$ is the carbocyclic or heterocyclic group and any one of hydrogens included in the carbocyclic or heterocyclic group is substituted by the group represented by the following Chemical Formula 2.

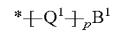   [Chemical Formula 2]

In Chemical Formula 2, p is an integer of 1 to 10, wherein if said p is 2 or more, each repeating unit of -($Q^1$)- repeating twice or more may be the same as or different from each other, $Q^1$ is independently a divalent group selected from the group consisting of —C≡C—, —CY$^1$=CY$^2$—, and a $C_6$-$C_{20}$ substituted or non-substituted aromatic or heteroaromatic group, and said $Y^1$ and $Y^2$ are independently —H, —F, —Cl, —CN, or —R$^1$, and $B^1$ is —H, —F, —Cl, —Br, —I, —CN, —NC, —NCO, —OCN, —SCN, —C(=O)NR$^1$R$^2$, —C(=O)R$^1$, —NH$_2$, —SH, —SR$^1$, —SO$_3$H, —SO$_2$R$^1$, —OH, —NO$_2$, —CF$_3$, —SF$_3$, a polymerizable group (said P defined in Chemical Formula 1), a $C_2$-$C_6$ alkenyl group, a $C_2$-$C_6$ alkynyl group, a $C_2$-$C_4$ acyl group, a $C_2$-$C_6$ alkynylene group of which the end is connected with a $C_2$-$C_4$ acyl group, a $C_1$-$C_5$ alcohol group, or a $C_1$-$C_{12}$ alkoxy group, wherein said $R^1$ and $R^2$ are independently —H or a $C_1$-$C_{12}$ alkyl.

As a result of continuing experiments of the present inventors, it is recognized that the compound having the structure like Chemical Formula 1 can show a liquid crystalline property and reverse wavelength dispersity surprisingly by itself, or by being polymerized or cross-linked with an arbitrary liquid crystalline compound and making the liquid crystalline compound show reverse wavelength dispersity even though it does not show a liquid crystalline property by itself, and thus it is possible to provide an optically anisotropic body that is thin and superior in optical properties.

Particularly, the compound represented by Chemical Formula 1 has the structure of a T form in which a bridging group of a conjugated structure having high polarizability is connected at any one part of the mesogenic group (particularly, the $L^1$-($D^1$-$G^1$)$_m$- group and -($G^2$-$D^2$)$_n$-$L^2$ group). Namely, the reverse wavelength dispersion compound according to the embodiment of the present invention has an asymmetric structure of the T form unlike a symmetric compound of an H form in which two rod-type mesogenic compounds are symmetrically connected by a bridging group. Therefore, the compound of Chemical Formula 1 can exhibit stable reverse wavelength dispersity due to the vertical bridging group having high polarizability and excellent orientation property due to the asymmetric mesogenic group of the T form at the same time.

A in Chemical Formula 1 is a $C_5$-$C_8$ non-aromatic carbocyclic or heterocyclic group or a $C_6$-$C_{20}$ aromatic or heteroaromatic group.

The carbocyclic or heterocyclic group in said A may be a 5-membered ring (for example, cyclopentane, tetrahydrofuran, tetrahydrothiofuran, pyrrolidine); a 6-membered ring (for example, cyclohexane, silinane, cyclohexene, tetrahydropyran, tetrahydrothiopyran, 1,3-dioxane, 1,3-dithiane, and piperidine); a 7-membered ring (for example, cycloheptane); or a fused group (for example, tetrahydronaphthalene, decahydronaphthalene, indane, bicycle[1.1.1]pentane-1,3-diyl, bicyclo[2.2.2]octane-1,4-diyl, spiro[3.3]heptane-2,6-diyl, and octahydro-4,7-methano-indane-2,5-diyl).

The aromatic group in said A may be benzene, biphenylene, triphenylene, naphthalene, anthracene, binaphthylene, phenanthrene, pyrene, dihydropyrene, chrysene, perylene, tetracene, pentacene, benzpyrene, fluorene, indene, indenofluorene, spirobifluorene, and so on. Further, the heteroaromatic group in said A, $G^1$, and $G^2$ may be a 5-membered ring (for example, pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, and 1,3,4-thiadiazole); a 6-membered ring (for example, pyridine, pyridazine, pyrimidine, pyrazine, 1,3,5-triazine, 1,2,4-triazine, 1,2,3-triazine, 1,2,4,5-tetrazine, 1,2,3,4-tetrazine, and 1,2,3,5-tetrazine); or a fused group (for example, carbazole, indole, isoindole, indolizine, indazole, benzimidazole, benzotriazole, purine, naphthimidazole, phenanthrimidazole, pyridimidazole, pyrazineimidazole, quinoxalineimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3-b]thiophene, thieno[3,2-b]thiophene, dithienothiophene, dithienopyridine, isobenzothiophene, dibenzothiophene, and benzothiadiazothiophene).

Preferably, said A may be a cyclohexane ring, a cyclohexene ring, a benzene ring, a naphthalene ring, or a phenanthrene ring. More preferably, said A may be selected from the group consisting of trans-1,4-cyclohexylene, 1,4-phenylene, 1,5-naphthylene, and 2,6-naphthylene.

According to the embodiment of the present invention, at least one of hydrogens included in said A may be selectively substituted by another functional group that enables an interaction between molecules with necessity. The functional group that enables an interaction between molecules makes it possible to exhibit more improved orientation stability through the interaction with other molecules. The kind of functional group that enables the interaction between molecules is not particularly limited, but it may preferably be —F, —Cl, —Br, —I, —CN, —NC, —NCO, —OCN, —SCN, —C(=O)NR$^1$R$^2$, —C(=O)R$^1$, —NH$_2$, —SH, —SR$^1$, —SO$_3$H, —SO$_2$R$^1$, —OH, —NO$_2$, —CF$_3$, —SF$_3$, a $C_2$-$C_6$ alkenyl group, a $C_2$-$C_6$ alkynyl group, a $C_2$-$C_4$ acyl group, a $C_2$-$C_6$ alkynylene group of which the end is connected with a $C_2$-$C_4$ acyl group, a $C_1$-$C_5$ alcohol group, or a $C_1$-$C_{12}$ alkoxy group. Here, said $R^1$ and $R^2$ are independently —H or a $C_1$-$C_{12}$ alkyl.

In addition, $E^1$, $E^2$, $D^1$, and $D^2$ in Chemical Formula 1 are independently a single bond or a divalent connecting group.

Concretely, $E^1$, $E^2$, $D^1$, and $D^2$ may independently be a single bond, —O—, —S—, —CO—, —COO—, —OCO—, —O—COO—, —CO—NR$^1$—, —NR$^1$—CO—, —NR$^1$—CO—NR$^1$—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —(CH$_2$)$_3$—, —(CH$_2$)$_4$—, —CF$_2$CH$_2$—, —CF$_2$CH$_2$—, —CH=CH—, —CY$^1$=CY$^2$—, —CH=N—, —N=CH—, —N=N—, —CH=CR$^1$—, —C≡C—, —CH=CH—COO—, —OCO—CH=CH—, or —CR$^1$R$^2$—. Here, said $Y^1$ and $Y^2$ are independently —H, —F, —Cl, —CN, or —R$^1$, and said $R^1$ and $R^2$ are independently —H or a $C_1$-$C_{12}$ alkyl.

$L^1$ and $L^2$ in Chemical Formula 1 are the ends of the mesogenic group, and they are independently —H, —F, —Cl, —Br, —I, —CN, —NC, —NCO, —OCN, —SCN, —C(=O)NR$^1$R$^2$, —C(=O)R$^1$, —O—C(=O)R$^1$, —NH$_2$, —SH, —SR$^1$, —SO$_3$H, —SO$_2$R$^1$, —OH, —NO$_2$, —CF$_3$, —SF$_3$, a substituted or non-substituted silyl, a $C_1$-$C_{40}$ substituted or non-substituted carbyl or hydrocarbyl, or —S$_p$—P, wherein at least one of said $L^1$ and $L^2$ is —S$_p$—P. Here, said P is a polymerizable group, said $S_p$ is a spacer group or a single bond, and $R^1$ and $R^2$ are independently —H or a $C_1$-$C_{12}$ alkyl.

For a non-restrictive example, said $L^1$ and $L^2$ may be a $C_1$-$C_{25}$ linear, branched, or cyclic alkyl group that is non-substituted, mono-substituted, or multi-substituted with F, Cl, Br, I, or CN, and at this time, one or more non-adjacent CH$_2$ groups may be independently substituted with —O—, —S—, —NH—, —NR$^1$—, SiR$^1$R$^2$—, —CO—, —COO—, —OCO—, —OCO—O—, —S—CO—, —CO—S—, —SO$_2$—, —CO—NR$^1$—, —NR$^1$—CO—, —NR$^1$—CO—NR$^1$—, —CY$^1$=CY$^2$—, or —C≡C—. Here, said $Y^1$ and $Y^2$ are independently —H, —F, —Cl, —CN, or —R$^1$, and said $R^1$ and $R^2$ are independently —H or a $C_1$-$C_{12}$ alkyl.

Furthermore, said $L^1$ and $L^2$ may be selected from a $C_1$-$C_{20}$ alkyl, a $C_1$-$C_{20}$ oxaalkyl, a $C_1$-$C_{20}$ alkoxy, a $C_2$-$C_{20}$ alkenyl, a $C_2$-$C_{20}$ alkynyl, a $C_1$-$C_{20}$ silyl, a $C_1$-$C_{20}$ ester, a $C_1$-$C_{20}$ amino, and a $C_1$-$C_{20}$ fluoroalkyl.

In —S$_p$—P that is an example of said $L^1$ and $L^2$, said P is an polymerizable group, and it may be CH$_2$=CZ$^1$—COO—, CH$_2$=CZ$^1$—CO—, CH$_2$=CZ$^2$—(O)$_a$—, CH$_3$—CH=CH—O—, (CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—, HO—CZ$^1$Z$^2$—, HS—CZ$^1$Z$^2$—, HZ$^1$N—, HO—CZ$^1$Z$^2$—NH—, CH$_2$=CZ$^1$—CO—NH—, CH$_2$=CH—(COO)$_a$-Phe-(O)$_b$—, CH$_2$=CH—(CO)$_a$-Phe-(O)$_b$—, Phe-CH=CH—, HOOC—, OCN—, Z$^1$Z$^2$Z$^3$Si—,

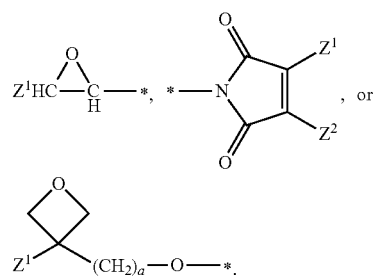

Here, said $Z^1$ to $Z^3$ are independently —H, —F, —Cl, —CN, —CF$_3$, a phenyl, or a $C_1$-$C_5$ alkyl, said Phe is 1,4-phenylene that is non-substituted or substituted with —F, —Cl, —Br, —I, —CN, —NC, —NCO, —OCN, —SCN, —C(=O) NR$^1$R$^2$, —C(=O)R$^1$, —NH$^2$, —SH, —SR$^1$, —SO$_3$H, —SO$_2$R$^1$, —OH, —NO$_2$, —CF$_3$, or —SF$_3$, and said a and b are independently 0 or 1.

In —S$_p$—P that is an example of said $L^1$ and $L^2$, said S$_p$ is selected from Chemical Formula —X'—S$_p$' that makes —S$_p$—P into —X'—S$_p$'—P. Said Sp' is a $C_1$-$C_{20}$ alkylene that is mono-substituted or multi-substituted with —F, —Cl, —Br, —I, or —CN, and one or more —CH$_2$— groups in said alkylene may be replaced by —O—, —S—, —NH—, —NR$^1$—, —SiR$^1$R$^2$—, —CO—, —COO—, —OCO—, —OCO—O—, —S—CO—, —CO—S—, —NR$^1$—CO—O—, —O—CO—NR$^1$—, —NR$^1$—CO—NR$^1$—, —CH═CH—, or —C≡C—. Further, said X' is —O—, —S—, —CO—, —COO—, —OCO—, —O—COO—, —CO—NR$^1$—, —NR$^1$—CO—, —NR$^1$—CO—NR$^1$—, —OCH$_2$—, —CH$_2$O—, —SCH$_2$—, —CH$_2$S—, —OCF$_2$—, —CF$_2$O—, —SCF$_2$—, —SF$_2$O—, —CF$_2$CH$_2$—, —CF$_2$CF$_2$—, —CH═N—, —N═CH—, —N═N—, —CH═CR$^1$—, —CY$^1$═CY$^2$—, —C≡C—, —CH═CH—COO—, —OCO—CH═CH—, or a single bond. Here, said Y$^1$ and Y$^2$ are independently —H, —F, —Cl, —CN, or —R$^1$, and said R$^1$ and R$^2$ are independently —H or a C$_1$-C$_{12}$ alkyl.

m and n in Chemical Formula 1 may be the same as or different from each other, and may independently be an integer of 1 to 5. Here, if said m or n is 2 or more, each repeating unit of -(D$^1$-G$^1$)- or -(G$^2$-D$^2$)- repeating twice or more may be the same as or different from each other. For example, when m is 2, D$^1$ or G$^1$ included in each repeating unit of -(D$^1$-G$^1$)-(D$^1$-G$^1$)- may be the same as or different from each other in the range disclosed above.

In addition, G$^1$ and G$^2$ in Chemical Formula 1 are independently a C$_5$-C$_8$ non-aromatic carbocyclic or heterocyclic group or a C$_6$-C$_{20}$ aromatic or heteroaromatic group, wherein at least one of said G$^1$ and G$^2$ is the carbocyclic or heterocyclic group.

The carbocyclic group, the heterocyclic group, the aromatic group, and the heteroaromatic group in said G$^1$ and G$^2$ are the same as defined in said A.

Particularly, according to the embodiment of the present invention, at least one of said G$^1$ and G$^2$ is the carbocyclic or heterocyclic group, and any one of hydrogens included in the carbocyclic or heterocyclic group is substituted by the group represented by the following Chemical Formula 2.

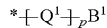 [Chemical Formula 2]

In Chemical Formula 2,
p is an integer of 1 to 10, wherein if said p is 2 or more, each repeating unit of -(Q$^1$)- repeating twice or more may be the same as or different from each other,
Q$^1$ is independently a divalent group selected from the group consisting of —C≡C—, —CY$^1$═CY$^2$—, and a C$_6$-C$_{20}$ substituted or non-substituted aromatic or heteroaromatic group, and said Y$^1$ and Y$^2$ are independently —H, —F, —Cl, —CN, or —R$^1$, and
B$^1$ is —H, —F, —Cl, —Br, —I, —CN, —NC, —NCO, —OCN, —SCN, —C(═O)NR$^1$R$^2$, —C(═O)R$^1$, —NH$_2$, —SH, —SO$_3$H, —SO$_2$R$^1$, —OH, —NO$_2$, —CF$_3$, —SF$_3$, a polymerizable group (said P defined in Chemical Formula 1), a C$_2$-C$_6$ alkenyl group, a C$_2$-C$_6$ alkynyl group, a C$_2$-C$_4$ acyl group, a C$_2$-C$_6$ alkynylene group of which the end is connected with a C$_2$-C$_4$ acyl group, a C$_1$-C$_5$ alcohol group, or a C$_1$-C$_{12}$ alkoxy group, wherein said R$^1$ and R$^2$ are independently —H or a C$_1$-C$_{12}$ alkyl.

In Chemical Formula 2, —[Q$^1$]$_3$- may be composed of one or more subgroups Q$^1$ selected from the group consisting of a pi-conjugated linear group, an aromatic group, and a heteroaromatic group. For example, said -[Q$^1$]$_p$- may be composed of one or more subgroups Q$^1$ selected from groups having a bond angle of 120° or more, preferably 180° or more. Here, p is an integer of 1 to 10, wherein if said p is 2 or more, each repeating unit of -(Q$^1$)- repeating twice or more may be the same as or different from each other.

For a non-restrictive example, such subgroup Q$^1$ may be a divalent aromatic group connected to an adjacent functional group of a para-position (for example, 1,4-phenylene, naphthalene-2,6-diyl, indane-2,6-diyl, thieno[3,2-b]thiophene-2,5-diyl) or a group including sp-hybridized carbons (for example, —C≡C—). Furthermore, said subgroup Q$^1$ may include —CH═CH—, —CY$^1$═CY$^2$—, and —CH═CR$^1$—. Here, said Y$^1$ and Y$^2$ are independently —H, —F, —Cl, —CN, or —R$^1$, and said R$^1$ and R$^2$ are independently —H or a C$_1$-C$_{12}$ alkyl.

Furthermore, said -[Q$^1$]$_p$- may include one or more groups selected from the group consisting of —C≡C—, substituted or non-substituted 1,4-phenylene, and substituted or non-substituted 9H-fluorene-2,7-diyl. At this time, an H atom at a 9-position in the fluorene group may be replaced by a carbyl or hydrocarbyl group.

Preferably, said -[Q$^1$]$_p$- may be selected from the group consisting of

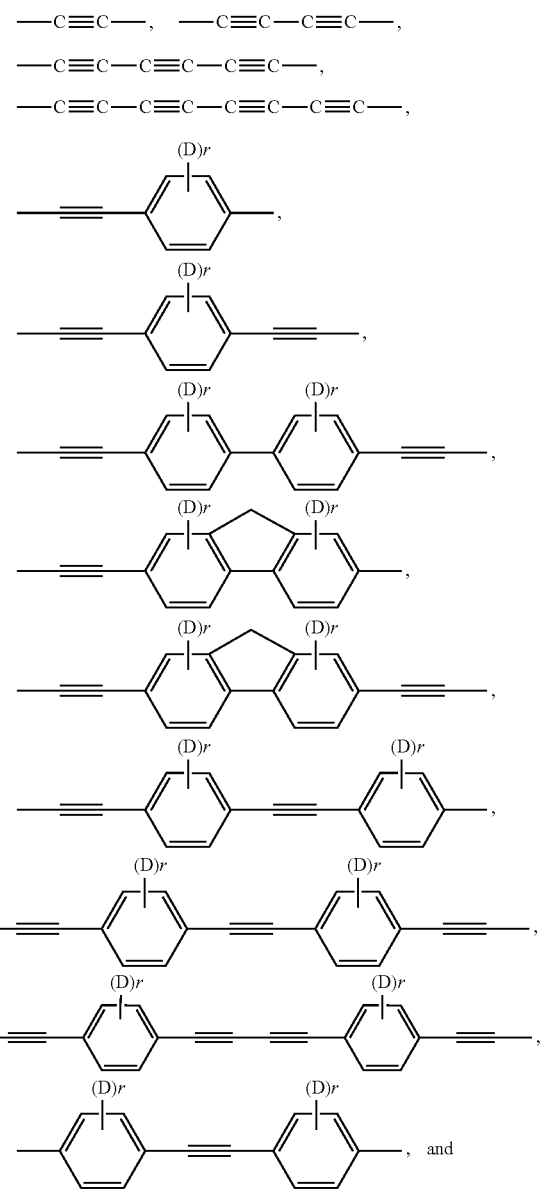

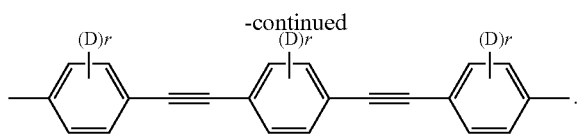

Here, said r is 0, 1, 2, 3, or 4, and said D may be —F, —Cl, —Br, —I, —CN, —NO$_2$, —NCO, —NCS, —OCN, —SCN, —C(=O)NR$^1$R$^2$, —C(=O)X, —C(=O)OR$^1$, —NR$^1$R$^2$, —OH, —SF$_5$, a substituted or non-substituted silyl, a C$_6$-C$_{12}$ aryl, a C$_1$-C$_{12}$ linear or branched alkyl, alkoxy, alkylcarbonyl, alkoxycarbonyl, alkylcarbonyloxy, or alkoxycarbonyloxy.

B$^1$ in Chemical Formula 2 is —H, —F, —Cl, —Br, —I, —CN, —NC, —NCO, —OCN, —SCN, —C(=O)NR$^1$R$^2$, —C(=O)R$^1$, —NH$_2$, —SH, —SR$^1$, —SO$_3$H, —SO$_2$R$^1$, —OH, —NO$_2$, —CF$_3$, —SF$_3$, a polymerizable group (said P defined in Chemical Formula 1), a C$_2$-C$_6$ alkenyl group, a C$_2$-C$_6$ alkynyl group, a C$_2$-C$_4$ acyl group, a C$_2$-C$_6$ alkynylene group of which the end is connected with a C$_2$-C$_4$ acyl group, a C$_1$-C$_5$ alcohol group, or a C$_1$-C$_{12}$ alkoxy group, wherein said R$^1$ and R$^2$ are independently —H or a C$_1$-C$_{12}$ alkyl.

Particularly, according to the embodiment of the present invention, said B$^1$ may preferably be one or more groups selected from the group consisting of a pi-conjugated linear group, an aromatic group, and a heteroaromatic group which make the bridging group of Chemical Formula 2 have a conjugate structure (for example, the group corresponding to said Q), among said exemplified groups.

For a non-restrictive example, the reverse wavelength dispersion compound of Chemical Formula 1 may be the compounds represented by RD-01 to RD-42 according to the after-mentioned examples. However, said reverse wavelength dispersion compound is not restricted to the compounds of RD-01 to RD-42, and it may be realized by various combinations in the above-mentioned range.

The reverse wavelength dispersion compound represented by Chemical Formula 1 may be synthesized by applying known reactions, and more detailed synthesis method will be explained through examples.

II. Reverse Wavelength Distribution Composition

According to another embodiment of the present invention, the reverse wavelength dispersion composition including the compound represented by Chemical Formula 1 is provided.

Said reverse wavelength dispersion composition may be a composition of which the compound represented by Chemical Formula 1 is dissolved in a solvent. The compound represented by Chemical Formula 1 may be included in said composition solely or in combination of 2 or more of the same kinds.

Here, radical polymerization initiators conventional in the art to which the present invention pertains may be used as the polymerization initiator. The content of the polymerization initiator may be determined in a conventional range which can effectively initiate the polymerization reaction of the reverse wavelength dispersion compound. According to the embodiment of the present invention, said polymerization initiator may be included in the content of 10 wt % or less, preferably 0.5 to 8 wt %, based on the total weight of the composition.

Said solvent may be benzene, toluene, xylene, mesitylene, n-butylbenzene, diethylbenzene, tetralin, methoxybenzene, 1,2-dimethoxybenzene, ethylene glycol dimethylether, diethylene glycol dimethylether, acetone, methylethylketone, methylisobutylketone, cyclopentanone, cyclohexanone, ethyl acetate, methyl lactate, ethyl lactate, ethylene glycol monomethyl ether acetate, propylene glycol monomethyl ether acetate, propylene glycol monoethyl ether acetate, γ-butyrolactone, 2-pyrrolidone, N-methyl-2-pyrrolidone, dimethylformamide, chloroform, dichloromethane, carbon tetrachloride, dichloroethane, trichloroethylene, tetrachloroethylene, chlorobenzene, t-butyl alcohol, diacetone alcohol, glycerin, monoacetin, ethylene glycol, triethylene glycol, hexylene glycol, ethylene glycol monomethylether, ethyl cellosolve, butyl cellosolve, or a mixture thereof. Among the solvents, the solvent of which the boiling point is 60 to 250° C. is favorable for forming a layer of uniform thickness and minimizing the residue of solvent or the fall in orientation when the composition is coated.

The reverse wavelength dispersion composition may further include a sensitizer such as xanthone, thioxanthone, chlorothioxanthone, phenothiazine, anthracene, diphenylanthracene, and so on, selectively with necessity.

Furthermore, the reverse wavelength dispersion composition may further include a surfactant such as a quaternary ammonium salt, an alkylamine oxide, a polyamine derivative, a polyoxyethylene-polyoxypropylene condensate, sodium lauryl sulfate, ammonium lauryl sulfate, an alkyl-substituted aromatic sulfonate, an alkyl phosphate, a perfluoroalkyl sulfonate, and so on; a shelf-life stabilizer such as hydroquinone, a hydroquinone monoalkylether-based compound, a pyrogallol-based compound, a thiophenol-based compound, a 2-naphthylamine-based compound, a 2-hydroxynaphthalene-based compound, and so on; an antioxidant such as 2,6-di-t-butyl-p-cresol, triphenylphosphite, and so on; or a UV-absorbent such as a salicylate-based compound, a benzophenyl-based compound, a benzotriazole-based compound, a cyanoacrylate-based compound, a nickel complex salt-based compound, and so on, selectively with necessity.

Said reverse wavelength dispersion composition may further include atomized materials for controlling the optical anisotropy or improving the strength of the polymerized layer, selectively with necessity. Said atomized materials may be atomized inorganic materials such as hectorite, montmorillonite, kaolinite, ZnO, TiO$_2$, CeO$_2$, Al$_2$O$_3$, Fe$_2$O$_3$, ZrO$_2$, MgF$_2$, SiO$_2$, SrCO$_3$, Ba(OH)$_2$, Ca(OH)$_2$, Ga(OH)$_3$, Al(OH)$_3$, Mg(OH)$_2$, Zr(OH)$_4$, and so on; or atomized organic materials such as carbon nanotubes, fullerene, a dendrimer, polyvinyl alcohol, polymethacrylate, polyimide, and so on.

Said reverse wavelength dispersion composition may further include an arbitrary liquid crystal compound in addition to the compound of Chemical Formula 1. Said arbitrary liquid crystal compound may or may not have a polymerization property. Here, for example, said arbitrary liquid crystal compound may be a liquid crystal compound having an ethylenic unsaturated bond, a compound having an optical active group, a rod-type liquid crystal compound, and so on. Said arbitrary liquid crystal compounds may be included in a proper amount according to their structure, and it may be favorable for the achievement of the goal disclosed above to include the arbitrary liquid crystal so that the content of the compound of Chemical Formula 1 is 20 wt % or more, or 50 wt % or more, based on the total weight of the compounds.

III. Optically Anisotropic Body

According to still another embodiment of the present invention, an optically anisotropic body formed by using the reverse wavelength dispersion composition is provided.

Particularly, said optically anisotropic body can show the reverse wavelength dispersity satisfying the following Equations I and II because it is formed by using the reverse wavelength dispersion composition.

$$\Delta n_{(450\,nm)}/\Delta n_{(550\,nm)} < 1.0 \quad \text{(Equation I)}$$

$$\Delta n_{(650\,nm)}/\Delta n_{(550\,nm)} > 1.0 \quad \text{(Equation II)}$$

($\Delta n(\lambda)$ in Equations I and II means a specific birefringent index at wavelength $\lambda$).

Said optically anisotropic body can be obtained by coating the reverse wavelength dispersion composition on a supporting substrate, aligning the liquid crystal compound in the reverse wavelength dispersion composition and then eliminating a solvent therefrom, and exposing the same to an energy ray for the polymerization.

Here, the supporting substrate is not particularly limited, but for a preferable example, a glass plate, a polyethylene terephthalate film, a polyimide film, a polyamide film, a polymethylmethacrylate film, a polystyrene film, a polyvinylchloride film, a polytetrafluoroethylene film, a cellulose-based film, a silicone film, and so on may be used. The supporting substrate on which a polyimide alignment layer or a polyvinyl alcohol alignment layer is formed may be preferably used.

Any known method can be used as the method of coating the composition on the supporting substrate, and for example, a roll coating method, a spin coating method, a bar coating method, a dip coating method, a spray coating method, and so on can be applied. The thickness of the layer formed by the composition may vary according to the use, and preferably it may be selected in the range of 0.01 to 100 μm.

Meanwhile, as the method of aligning the liquid crystal compound, for a non-restrictive example, a method of carrying out pre-alignment treatment on the supporting substrate may be used. Said alignment treatment may be carried out by forming a liquid crystal alignment layer including various polyimide alignment layers or polyvinyl alcohol-based alignment layers on the supporting substrate, and carrying out a treatment such as rubbing. Furthermore, a method of applying a magnetic field or an electric field to the composition on the supporting substrate may be used.

The method of polymerizing the reverse wavelength dispersion composition may be a known method using light, heat, or electromagnetic waves.

The optically anisotropic body may be used for retardation films, polarization devices, antireflection layers, selective radiation layers, view angle compensation layers, and so on of a liquid crystal display or an OLED type of display. Particularly, when the optically anisotropic body formed by using the composition is applied to an OLED type of display, the interference by external light can be minimized and it is possible to realize more perfect black.

Advantageous Effects

The reverse wavelength dispersion compound according to the present invention can provide a stronger and more stable reverse wavelength dispersion property, and makes it possible to provide an optically anisotropic body having excellent optical properties.

DETAILED DESCRIPTION OF THE EMBODIMENTS

Hereinafter, functions and effects of the invention are explained in more detail through concrete examples. However, these examples are only for the understanding of the present invention, and the scope of the present invention is not limited to or by them.

Example 1: Synthesis of Compound RD-01

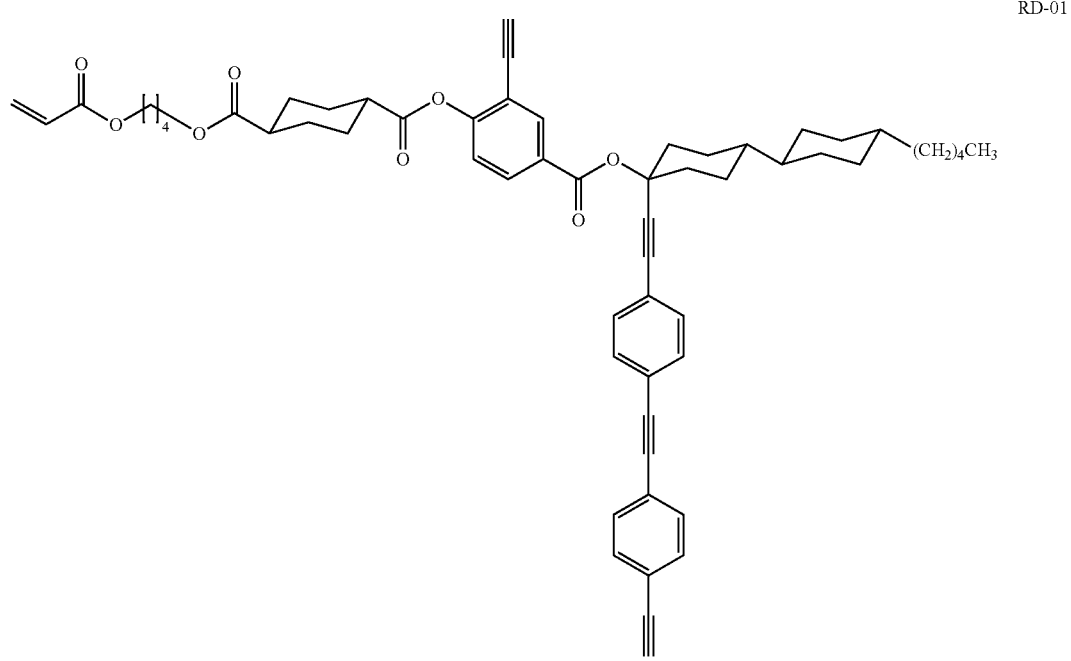

Figure 1A:
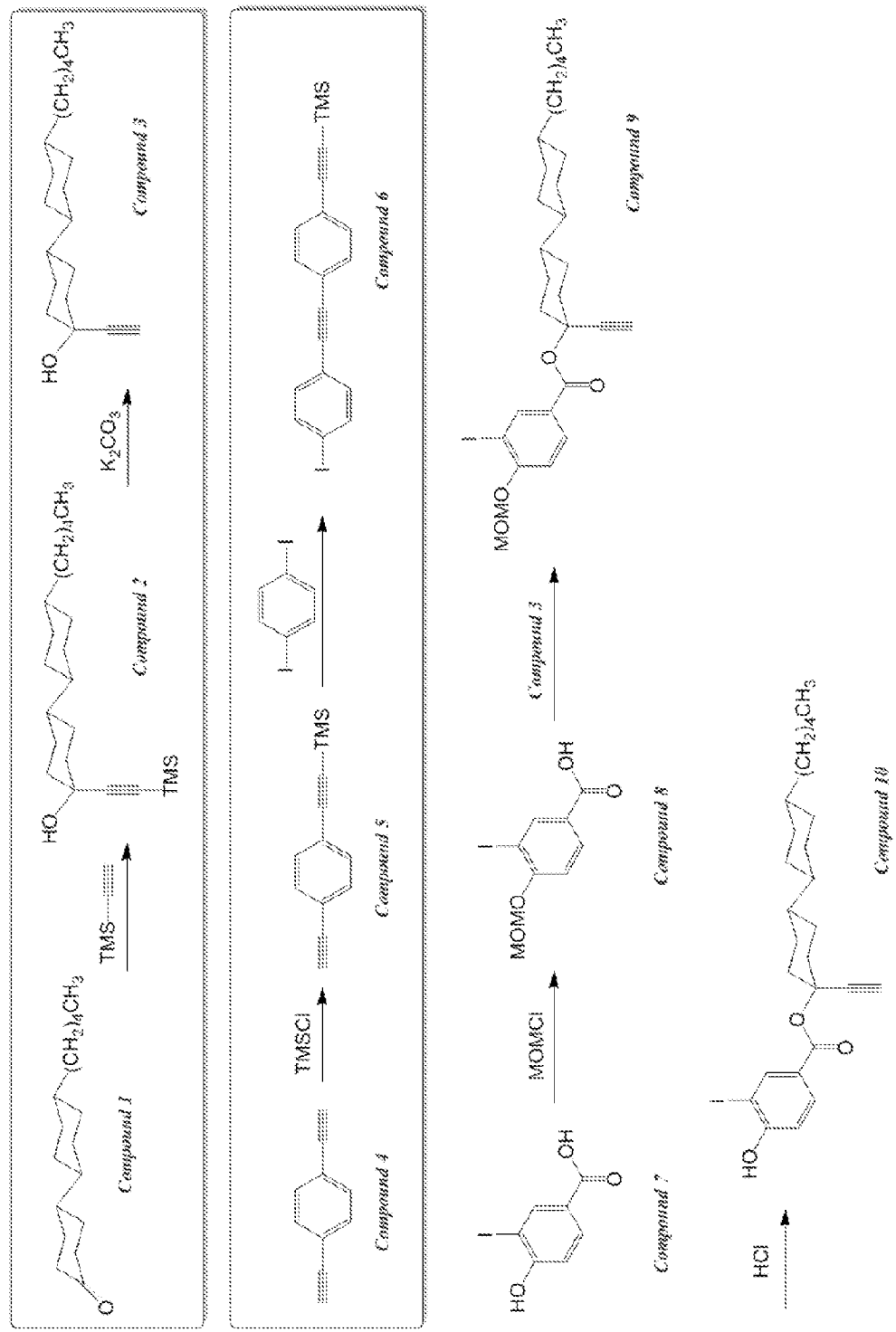
FIGS. 1a to 10 respectively illustrate the scheme of synthesis of the reverse wavelength dispersion compound according to the embodiments of the present invention.
Figure 1B:
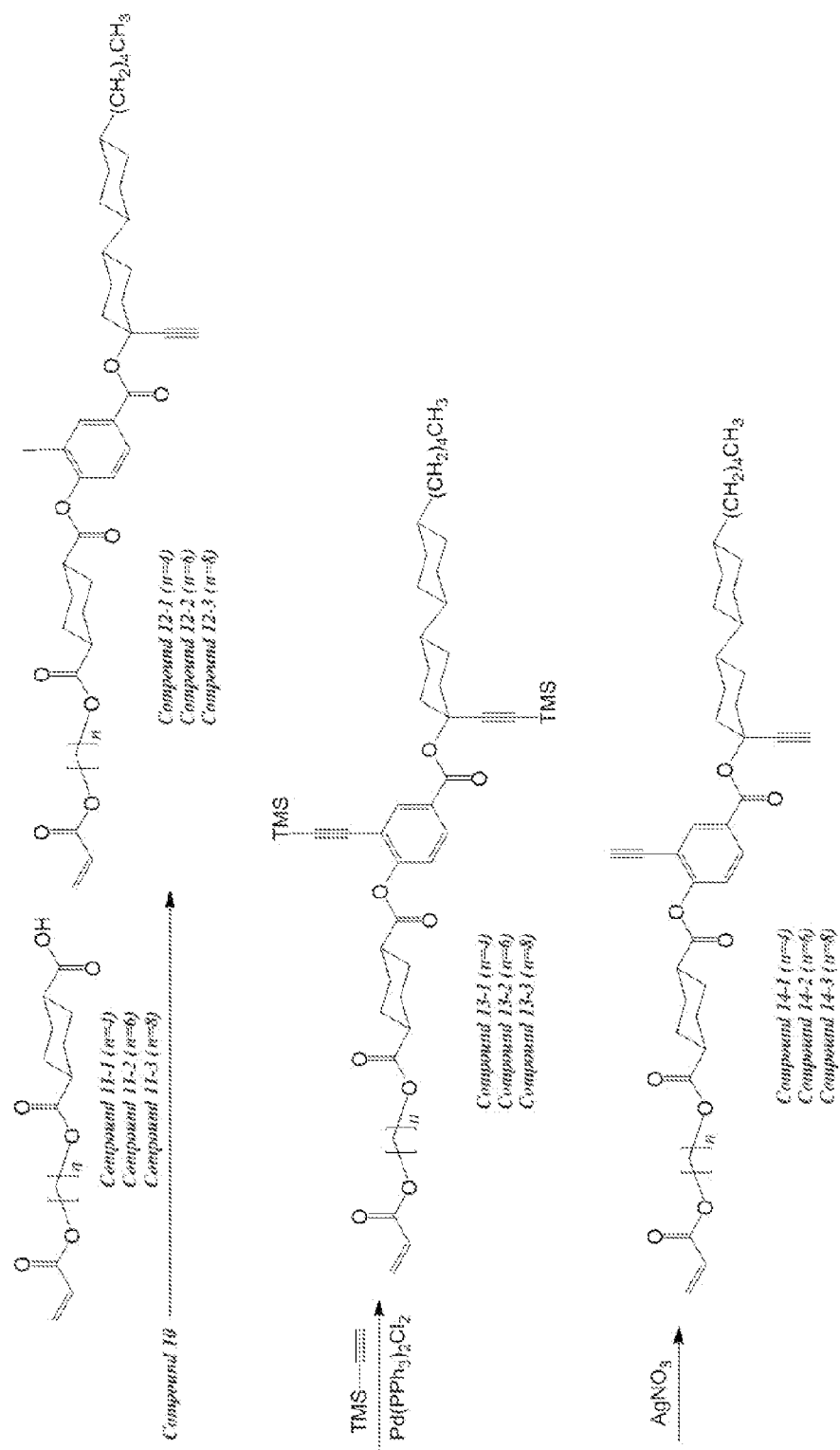
Figure 1C:
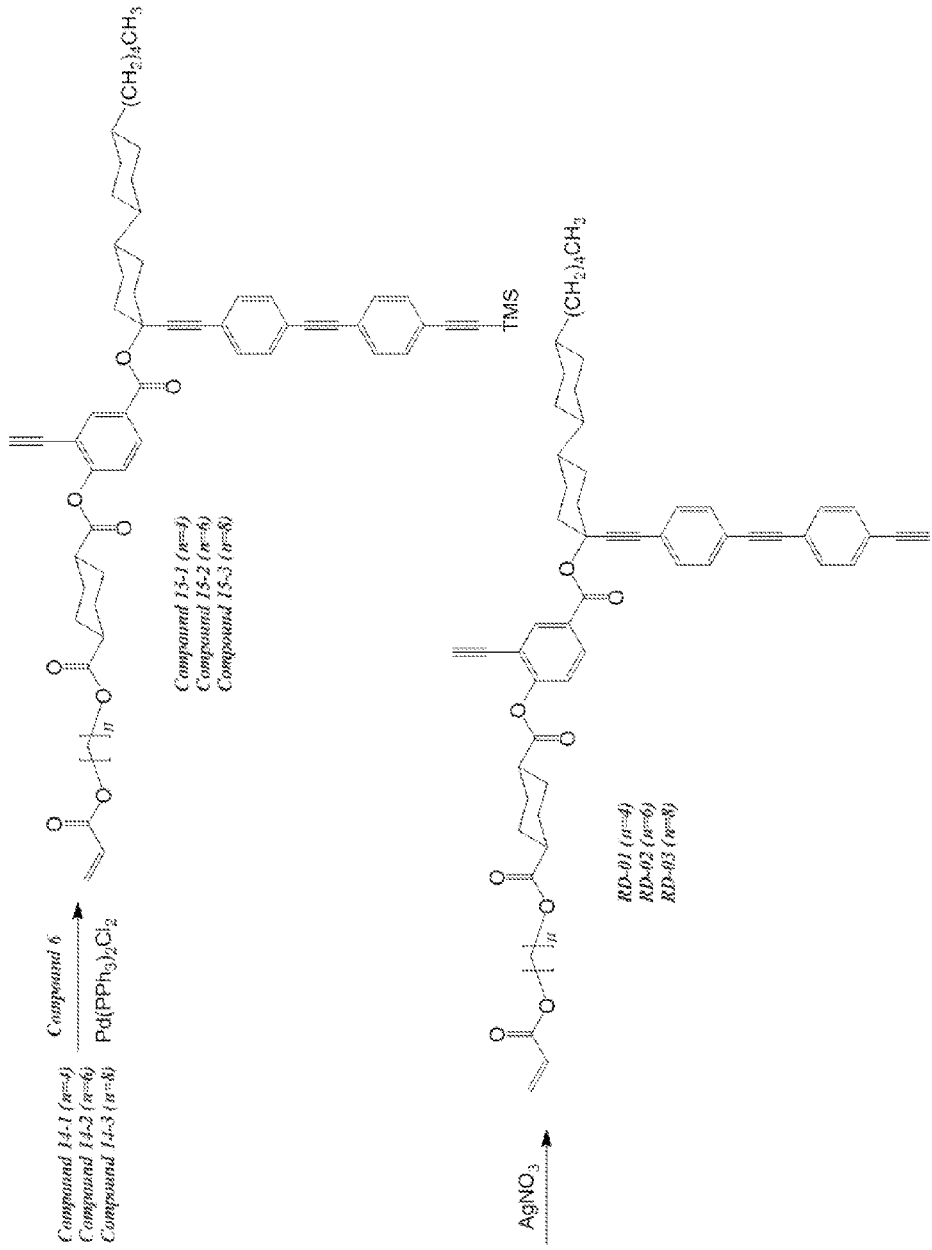

Compound RD-01 was synthesized according to the scheme illustrated in FIGS. 1a to 1c.

Synthesis of Compound 2

After dissolving about 100 g of Compound 1 ((1's,4'r)-4'-pentyl-[1,1'-bi(cyclohexan)]-4-one) and about 60 g of tetramethylenediamine in tetrahydrofuran, about 300 ml of n-butyl lithium was slowly added thereto dropwise at about −78° C. After stirring the mixture for about 2 h, ethynyltrimethylsilane was added thereto and the mixture was additionally stirred for about 1 h. Then, about 120 g of Compound 2 was obtained by extracting the reacted product with dichloromethane and water, chemically drying the obtained organic layer, and refining the same with column chromatography.

Synthesis of Compound 3

After dissolving about 120 g of Compound 2 and about 100 g of $K_2CO_3$ (potassium carbonate) in methanol, the mixture was stirred for about 24 h at room temperature. After eliminating extra $K_2CO_3$ therefrom by filtering the same, the obtained product was extracted with dichloromethane and water. Then, about 110 g of Compound 3 was obtained by chemically drying the extracted organic layer for eliminating the solvent therefrom, and refining the same with column chromatography.

Synthesis of Compound 5

After dissolving about 100 g of Compound 4 (1,4-diethynylbenzene) in tetrahydrofuran, the mixture was stirred for about 20 min at about −78° C. About 500 ml of n-butyl lithium in 2.5M hexane was added thereto dropwise for about 2 h. After stirring the same for about 4 h, about 100 ml of chlorotrimethylsilane was added thereto and the mixture was stirred for about 24 h. Then, about 60 g of Compound 5 was obtained by extracting the reacted product with ethyl acetate and water, chemically drying the obtained organic layer, and refining the same with column chromatography.

Synthesis of Compound 6

After dissolving about 200 g of 1,4-diiodobenzene, about 3 g of $Pd(PPh_3)_2Cl_2$ (bis(triphenylphosphine)palladium(II) dichloride), about 5 g of CuI (copper iodide), and about 200 ml of N,N-diisopropylethylamine in tetrahydrofuran, about 50 g of Compound 5 dissolved in tetrahydrofuran was slowly added thereto dropwise. After refluxing and stirring the mixture for about 24 h, the produced salt was filtered and eliminated therefrom and the obtained product was extracted with dichloromethane and water. About 70 g of Compound 6 was obtained by chemically drying the extracted organic layer and refining the same with column chromatography.

Synthesis of Compound 8

After dissolving 100 g of Compound 7 (4-hydroxy-3-iodobenzoic acid) and about 400 g of N,N-diisopropylethylamine in dichloromethane, about 200 g of methylchloromethylether was slowly added thereto dropwise at about 0° C. After stirring the mixture for about 24 h, the product was washed with about 500 ml of ammonium chloride and extracted with dichloromethane and water. The extracted organic layer was chemically dried and the solvent was eliminated therefrom. The product obtained in this way and a potassium hydroxide aqueous solution were put in methanol and the solution was refluxed and stirred for about 3 h. The product was extracted by adding 6N hydrochloric acid thereto and then the solvent was eliminated therefrom by filtering the same. Then, about 110 g of Compound 8 was obtained by eliminating extra foreign substances therefrom by using hexane, and drying the same for about 48 h.

Synthesis of Compound 9

After dissolving about 100 g of Compound 8, about 100 g of Compound 3, and about 70 g of 4-(dimethylamino)pyridine in dichloromethane, the mixture was stirred for about 30 min. After adding about 80 g of 1-ethyl-3-(3-dimethylaminopropyl)carbodiimide thereto and stirring the same for about 24 h, the obtained product was extracted with dichloromethane and water. Then, about 150 g of Compound 9 was obtained by chemically drying the extracted organic layer and refining the same with column chromatography.

Synthesis of Compound 10

After dissolving about 100 g of Compound 9 and about 300 ml of 6N hydrochloric acid in tetrahydrofuran, the mixture was stirred for about 24 h at about 40° C. The reacted product was extracted with dichloromethane and water. Then, about 80 g of Compound 10 was obtained by chemically drying the extracted organic layer and refining the same with column chromatography.

Synthesis of Compound 12-1

After dissolving about 80 g of Compound 10, about 50 g of Compound 11-1 ((1 r,4r)-4-((4-(acryloyloxy)butoxy)carbonyl)cyclohexanecarboxylic acid), about 5 g of 4-(dimethylamino)pyridine, and about 50 g of N,N-diisopropylethylamine in dichloromethane, the mixture was stirred for about 30 min. After adding about 80 g of 1-ethyl-3-(3-dimethylaminopropyl)carbodiimide and about 50 g of ethynyltrimethylsilane thereto and stirring the same for about 24 h, the obtained product was extracted with dichloromethane and water. Then, about 100 g of Compound 12-1 was obtained by chemically drying the extracted organic layer and refining the same with column chromatography.

Synthesis of Compound 13-1

After dissolving about 80 g of Compound 12-1, about 20 g of ethynyltrimethylsilane, about 3 g of $Pd(PPh_3)_2Cl_2$ (bis(triphenylphosphine)palladium(II) dichloride), and about 5 g of CuI (copper iodide) in tetrahydrofuran, the solution was refluxed and stirred for about 24 h. The produced salt was filtered and eliminated therefrom and the obtained product was extracted with dichloromethane and water. About 70 g of Compound 13-1 was obtained by chemically drying the extracted organic layer and refining the same with column chromatography.

Synthesis of Compound 14-1

After dissolving about 70 g of Compound 13-1 and about 6 g of $AgNO_3$ (silver nitrate) in the solvent mixture (water:dichloromethane:ethanol=1:6:3) and stirring the same for about 24 h, about 50 g of Compound 14-1 was obtained by chemically drying the extracted organic layer and refining the same with column chromatography.

Synthesis of Compound 15-1

After dissolving about 50 g of Compound 14-1, about 20 g of Compound 6, about 3 g of $Pd(PPh_3)_2Cl_2$ (bis(triphenylphosphine)palladium(II) dichloride), and about 5 g of CuI (copper iodide) in tetrahydrofuran, the solution was refluxed and stirred for about 24 h. The produced salt was filtered and eliminated therefrom and the obtained product was extracted with dichloromethane and water. About 30 g of Compound 15-1 was obtained by chemically drying the extracted organic layer and refining the same with column chromatography.

Synthesis of Compound RD-01

After dissolving about 30 g of Compound 15-1 and about 6 g of $AgNO_3$ (silver nitrate) in the solvent mixture (water: dichloromethane:ethanol=1:6:3) and stirring the same for about 24 h, about 20 g of Compound RD-01 was obtained by chemically drying the extracted organic layer and refining the same with column chromatography.

The NMR spectrum of the obtained Compound RD-01 is as follows.

$^1$H NMR (CDCl$_3$, standard material TMS) δ(ppm): 8.04 (2H, d), 7.56 (4H, d), 7.51 (4H, d), 7.40 (2H, d), 6.27 (1H, d), 6.05 (1H, dd), 5.59 (1H, d), 4.13 (2H, t), 4.05 (1H, s), 3.97 (2H, t), 3.52 (1H, s), 1.60-1.12 (48H, m)

Example 2: Synthesis of Compound RD-02

Compound RD-02 was synthesized according to the scheme shown in FIGS. 1a to 1c.

Synthesis of Compound 12-2

About 100 g of Compound 12-2 was obtained by the same method as the synthesis of Compound 12-1 of Example 1, except that about 55 g of Compound 11-2 ((1 r,4r)-4-(((6-(acryloyloxy)hexyl)oxy)carbonyl)cyclohexanecarboxylic acid) was used instead of Compound 11-1.

Synthesis of Compound 13-2

About 70 g of Compound 13-2 was obtained by the same method as the synthesis of Compound 13-1 of Example 1, except that Compound 12-2 was used instead of Compound 12-1.

Synthesis of Compound 14-2

About 70 g of Compound 14-2 was obtained by the same method as the synthesis of Compound 14-1 of Example 1, except that Compound 13-2 was used instead of Compound 13-1.

Synthesis of Compound 15-2

About 70 g of Compound 15-2 was obtained by the same method as the synthesis of Compound 15-1 of Example 1, except that Compound 14-2 was used instead of Compound 14-1.

Synthesis of Compound RD-02

About 50 g of Compound RD-02 was obtained by the same method as the synthesis of Compound RD-01 of Example 1, except that Compound 15-2 was used instead of Compound 15-1.

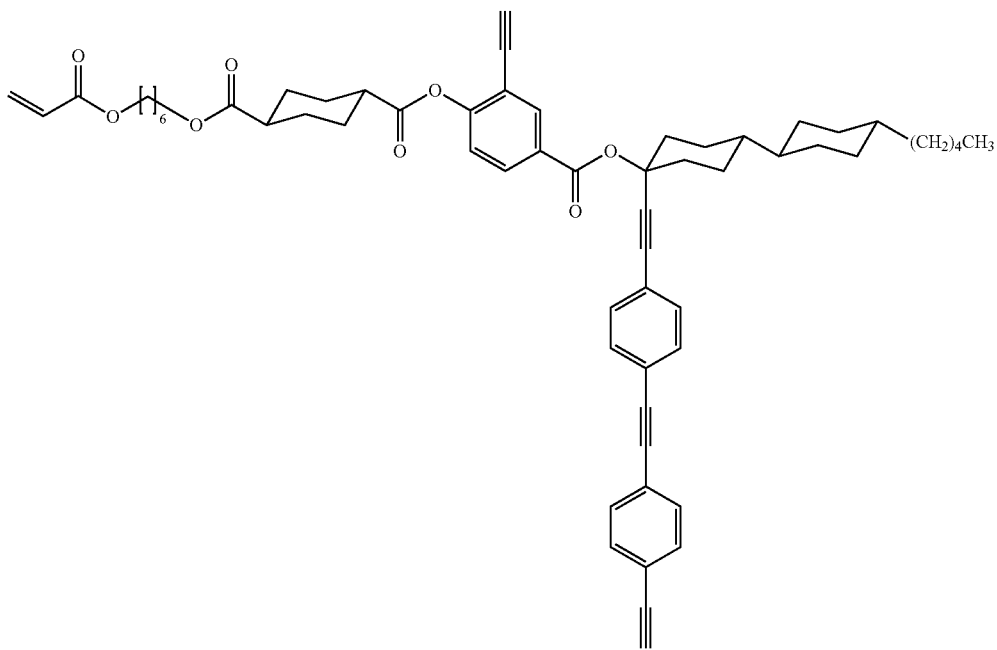

RD-02

The NMR spectrum of the obtained Compound RD-02 is as follows.

$^1$H NMR (CDCl$_3$, standard material TMS) δ(ppm): 8.04 (2H, d), 7.56 (4H, d), 7.51 (4H, d), 7.40 (2H, d), 6.27 (1H, d), 6.05 (1H, dd), 5.59 (1H, d), 4.13 (2H, t), 4.05 (1H, s), 3.97 (2H, t), 3.52 (1H, s), 1.60-1.12 (52H, m)

Example 3: Synthesis of Compound RD-03

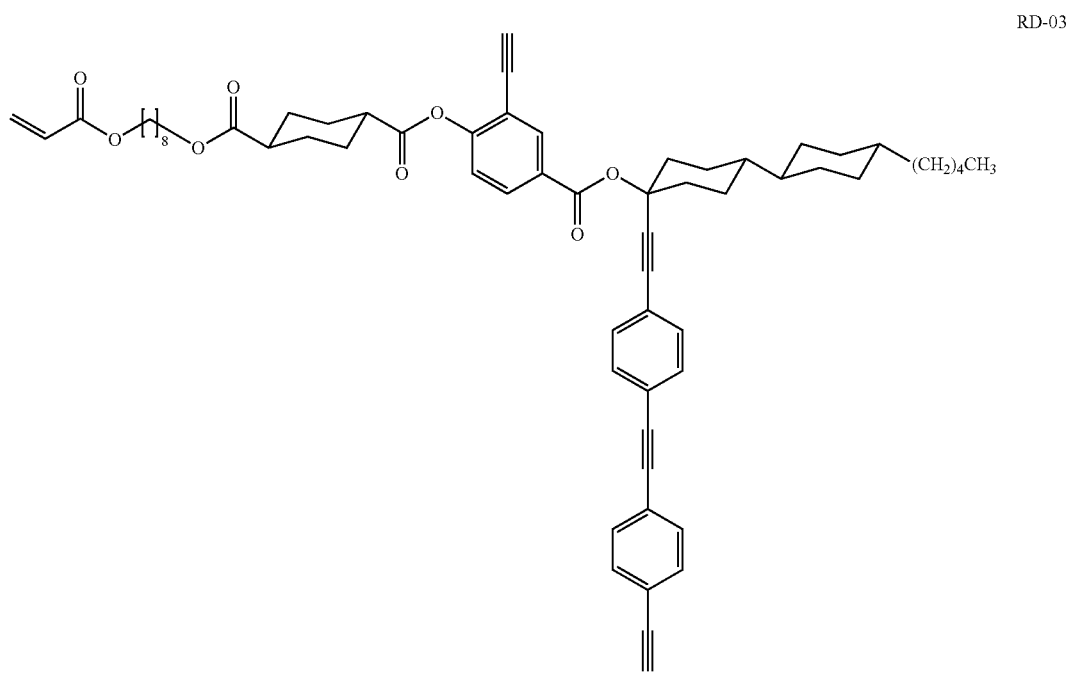

Compound RD-03 was synthesized according to the scheme shown in FIGS. 1a to 1c.

Synthesis of Compound 12-3

About 100 g of Compound 12-3 was obtained by the same method as the synthesis of Compound 12-1 of Example 1, except that about 60 g of Compound 11-3 ((1r,4r)-4-(((8-(acryloyloxy)octyl)oxy)carbonyl)cyclohexanecarboxylic acid) was used instead of Compound 11-1.

Synthesis of Compound 13-3

About 70 g of Compound 13-3 was obtained by the same method as the synthesis of Compound 13-1 of Example 1, except that Compound 12-3 was used instead of Compound 12-1.

Synthesis of Compound 14-3

About 70 g of Compound 14-3 was obtained by the same method as the synthesis of Compound 14-1 of Example 1, except that Compound 13-3 was used instead of Compound 13-1.

Synthesis of Compound 15-3

About 70 g of Compound 15-3 was obtained by the same method as the synthesis of Compound 15-1 of Example 1, except that Compound 14-3 was used instead of Compound 14-1.

Synthesis of Compound RD-03

About 50 g of Compound RD-03 was obtained by the same method as the synthesis of Compound RD-01 of Example 1, except that Compound 15-3 was used instead of Compound 15-1.

The NMR spectrum of the obtained Compound RD-03 is as follows.

$^1$H NMR (CDCl$_3$, standard material TMS) δ(ppm): 8.04 (2H, d), 7.56 (4H, d), 7.51 (4H, d), 7.40 (2H, d), 6.27 (1H, d), 6.05 (1H, dd), 5.59 (1H, d), 4.13 (2H, t), 4.05 (1H, s), 3.97 (2H, t), 3.52 (1H, s), 1.60-1.12 (56H, m)

Example 4: Synthesis of Compound RD-04

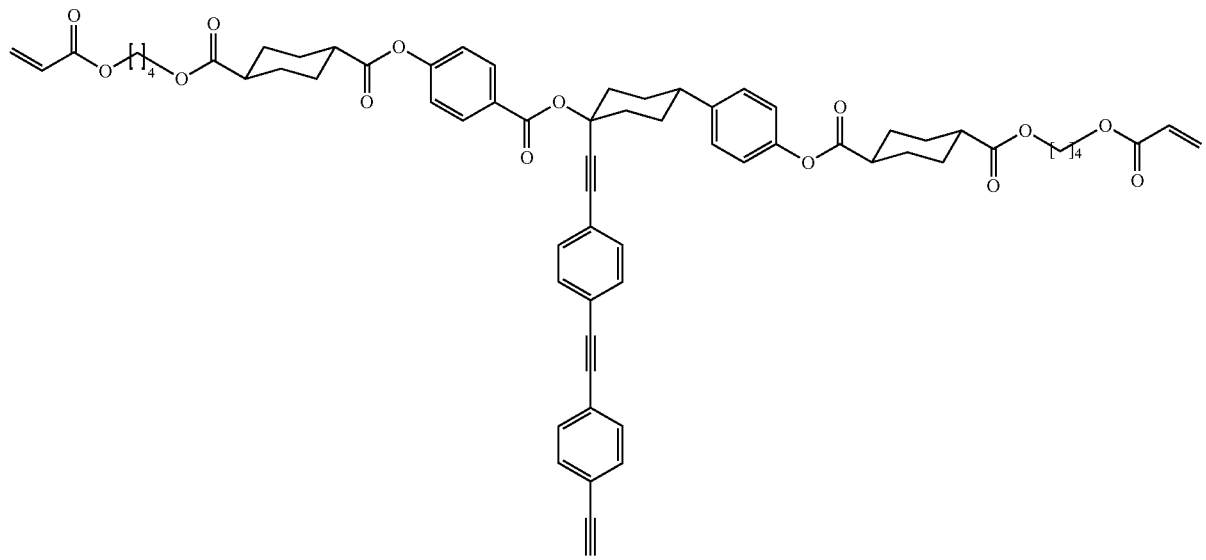

RD-04

Figure 2B:
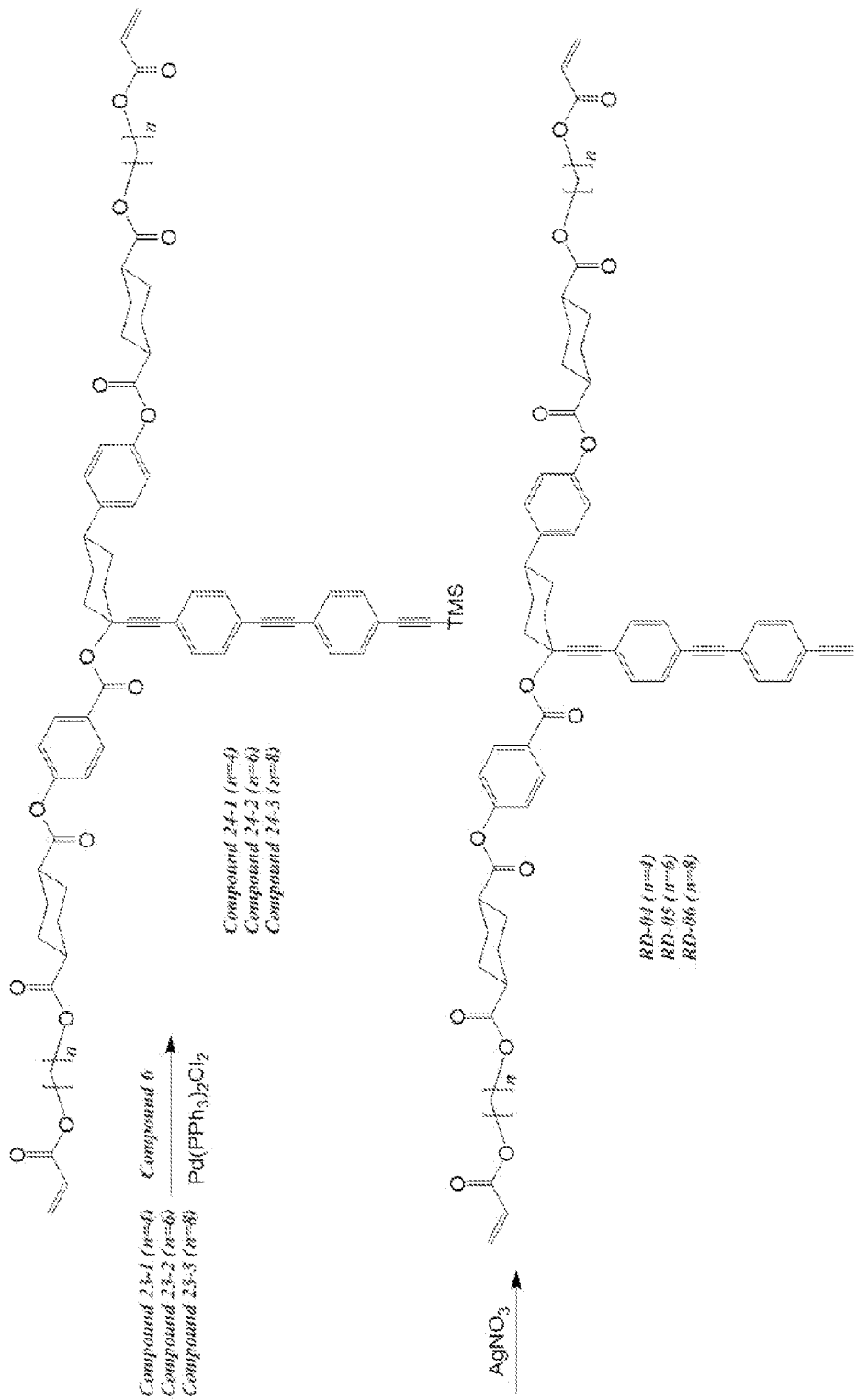

Compound RD-04 was synthesized according to the scheme shown in FIGS. 2a and 2b.

Synthesis of Compound 17

After dissolving about 100 g of Compound 16 (4-(4-hydroxyphenyl)cyclohexanone) and about 120 g of N,N-diisopropylethylamine in dichloromethane, about 50 g of methylchloromethylether was slowly added thereto dropwise. After stirring the mixture for about 2 h, the product was extracted with dichloromethane and water. Then, about 120 g of Compound 17 was obtained by chemically drying the extracted organic layer for eliminating the solvent therefrom, and refining the same with column chromatography.

Synthesis of Compound 18

After dissolving about 120 g of Compound 17 and about 100 g of N,N,N',N'-tetramethylethylenediamine in tetrahydrofuran, the mixture was stirred for about 20 min at about −78° C. About 500 ml of n-butyl lithium in 2.5M hexane was added thereto dropwise for about 2 h. After stirring the same for about 4 h, ethynyltrimethylsilane was added thereto and the mixture was additionally stirred for about 24 h. Then, the reacted product was extracted with ethyl acetate and water, and about 100 g of Compound 18 was obtained by chemically drying the obtained organic layer, and refining the same with column chromatography.

Synthesis of Compound 19

After dissolving about 100 g of Compound 18 and about 10 g of tetrabutylammonium fluoride hydrate in tetrahydrofuran, the mixture was stirred for about 2 h. The reacted product was extracted with dichloromethane and water, and about 80 g of Compound 19 was obtained by chemically drying the extracted organic layer and refining the same with column chromatography.

Synthesis of Compound 21

After dissolving about 70 g of Compound 19, about 70 g of Compound [4-(methoxymethoxy)benzoic acid], and about 50 g of 4-(dimethylamino)pyridine in dichloromethane, the mixture was stirred for about min. After adding about 80 g of 1-ethyl-3-(3-dimethylaminopropyl)carbodiimide thereto and stirring the same for about 24 h, the obtained product was extracted with dichloromethane and water. Then, about 80 g of Compound 21 was obtained by chemically drying the extracted organic layer and refining the same with column chromatography.

Synthesis of Compound 22

After dissolving about 80 g of Compound 21 and about 300 ml of 6N hydrochloric acid in tetrahydrofuran, the mixture was stirred for about 24 h at about 40° C. Then, the reacted product was extracted with dichloromethane and water, and about 60 g of Compound 22 was obtained by chemically drying the extracted organic layer and refining the same with column chromatography.

Synthesis of Compound 23-1

After dissolving about 60 g of Compound 22, about 50 g of Compound 11-1 ((1 r,4r)-4-((4-(acryloyloxy)butoxy)carbonyl)cyclohexanecarboxylic acid), about 5 g of 4-(dimethylamino)pyridine, and about 50 g of N,N-diisopropylethylamine in dichloromethane, the mixture was stirred for about 30 min. After adding about 80 g of 1-ethyl-3-(3-dimethylaminopropyl)carbodiimide and about 50 g of ethynyltrimethylsilane thereto and stirring the same for about 24 h, the obtained product was extracted with dichloromethane and water. Then, about 80 g of Compound 23-1 was obtained by chemically drying the extracted organic layer and refining the same with column chromatography.

Synthesis of Compound 24-1

After dissolving about 80 g of Compound 23-1, about 30 g of Compound 6 of Example 1, about 3 g of Pd(PPh$_3$)$_2$Cl$_2$ (bis(triphenylphosphine)palladium(II) dichloride), and about 5 g of CuI (copper iodide) in tetrahydrofuran, the solution was refluxed and stirred for about 24 h. The produced salt was filtered and eliminated therefrom and the obtained product was extracted with dichloromethane and water. About 70 g of Compound 24-1 was obtained by chemically drying the extracted organic layer and refining the same with column chromatography.

Synthesis of Compound RD-04

After dissolving about 50 g of Compound 24-1 and about 10 g of AgNO$_3$ (silver nitrate) in the solvent mixture (water:dichloromethane:ethanol=1:6:3) and stirring the same for about 24 h. About 30 g of Compound RD-04 was obtained by chemically drying the extracted organic layer and refining the same with column chromatography.

The NMR spectrum of the obtained Compound RD-04 is as follows.

$^1$H NMR (CDCl$_3$, standard material TMS) δ(ppm): 8.04 (2H, d), 7.56 (4H, d), 7.51 (4H, d), 7.47 (2H, d), 7.40 (2H, d), 7.21 (2H, d), 6.27 (2H, dd), 6.05 (2H, dd), 5.59 (2H, dd), 4.13 (4H, t), 4.05 (1H, s), 3.97 (4H, t), 2.50 (1H, s), 1.60-1.12 (23H, m)

Example 5: Synthesis of Compound RD-05

Synthesis of Compound 23-2

About 100 g of Compound 23-2 was obtained by the same method as the synthesis of Compound 23-1 of Example 4, except that Compound 11-2 ((1 r,4r)-4-(((6-(acryloyloxy)hexyl)oxy)carbonyl)cyclohexanecarboxylic acid) was used instead of Compound 11-1.

Synthesis of Compound 24-2

About 70 g of Compound 24-2 was obtained by the same method as the synthesis of Compound 24-1 of Example 4, except that Compound 23-2 was used instead of Compound 23-1.

Synthesis of Compound RD-05

About 50 g of Compound RD-05 was obtained by the same method as the synthesis of Compound RD-04 of Example 4, except that Compound 24-2 was used instead of Compound 24-1.

The NMR spectrum of the obtained Compound RD-05 is as follows.

$^1$H NMR (CDCl$_3$, standard material TMS) δ(ppm): 8.04 (2H, d), 7.56 (4H, d), 7.51 (4H, d), 7.47 (2H, d), 7.40 (2H, d), 7.21 (2H, d), 6.27 (2H, dd), 6.05 (2H, dd), 5.59 (2H, dd), 4.13 (4H, t), 4.05 (1H, s), 3.97 (4H, t), 2.50 (1H, s), 1.60-1.12 (31H, m)

Compound RD-05 was synthesized according to the scheme shown in FIGS. 2a and 2b.

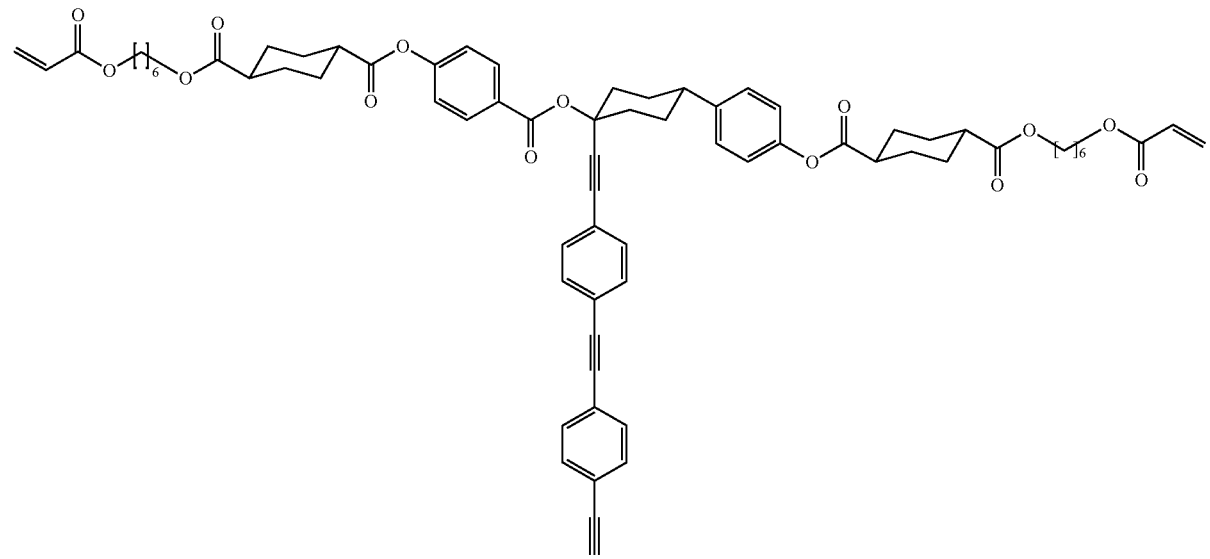

RD-05

Example 6: Synthesis of Compound RD-06

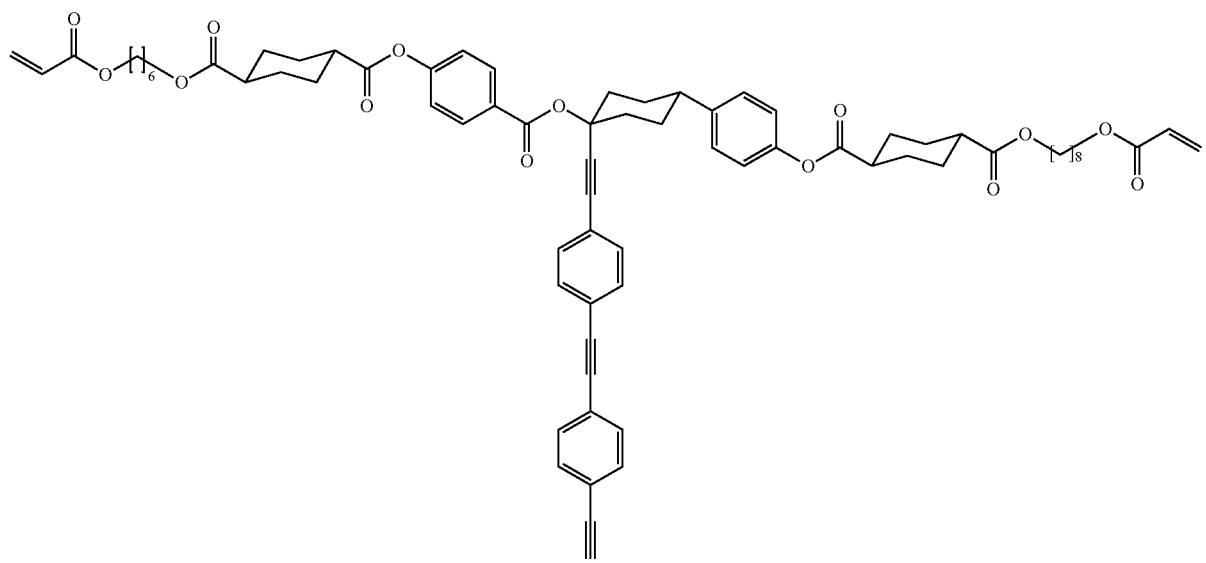

Compound RD-06 was synthesized according to the scheme shown in FIGS. 2a and 2b.

Synthesis of Compound 23-3

About 100 g of Compound 23-3 was obtained by the same method as the synthesis of Compound 23-1 of Example 4, except that Compound 11-3 (((1 r,4r)-4-(((8-(acryloyloxy)octyl)oxy)carbonyl)cyclohexanecarboxylic acid) was used instead of Compound 11-1.

Synthesis of Compound 24-3

About 70 g of Compound 24-3 was obtained by the same method as the synthesis of Compound 24-1 of Example 4, except that Compound 23-3 was used instead of Compound 23-1.

Synthesis of Compound RD-06

About 50 g of Compound RD-06 was obtained by the same method as the synthesis of Compound RD-04 of Example 4, except that Compound 24-3 was used instead of Compound 24-1.

The NMR spectrum of the obtained Compound RD-06 is as follows.

$^1$H NMR (CDCl$_3$, standard material TMS) δ(ppm): 8.04 (2H, d), 7.56 (4H, d), 7.51 (4H, d), 7.47 (2H, d), 7.40 (2H, d), 7.21 (2H, d), 6.27 (2H, dd), 6.05 (2H, dd), 5.59 (2H, dd), 4.13 (4H, t), 4.05 (1H, s), 3.97 (4H, t), 2.50 (1H, s), 1.60-1.12 (39H, m)

Example 7: Synthesis of Compound RD-07

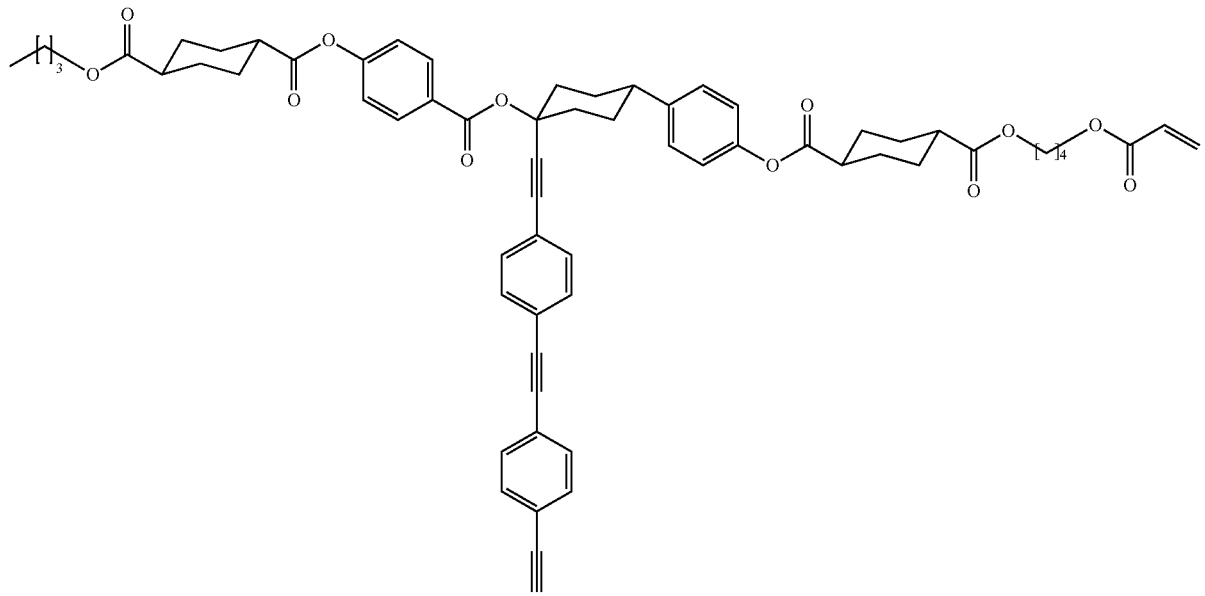

RD-07

Figure 3A:
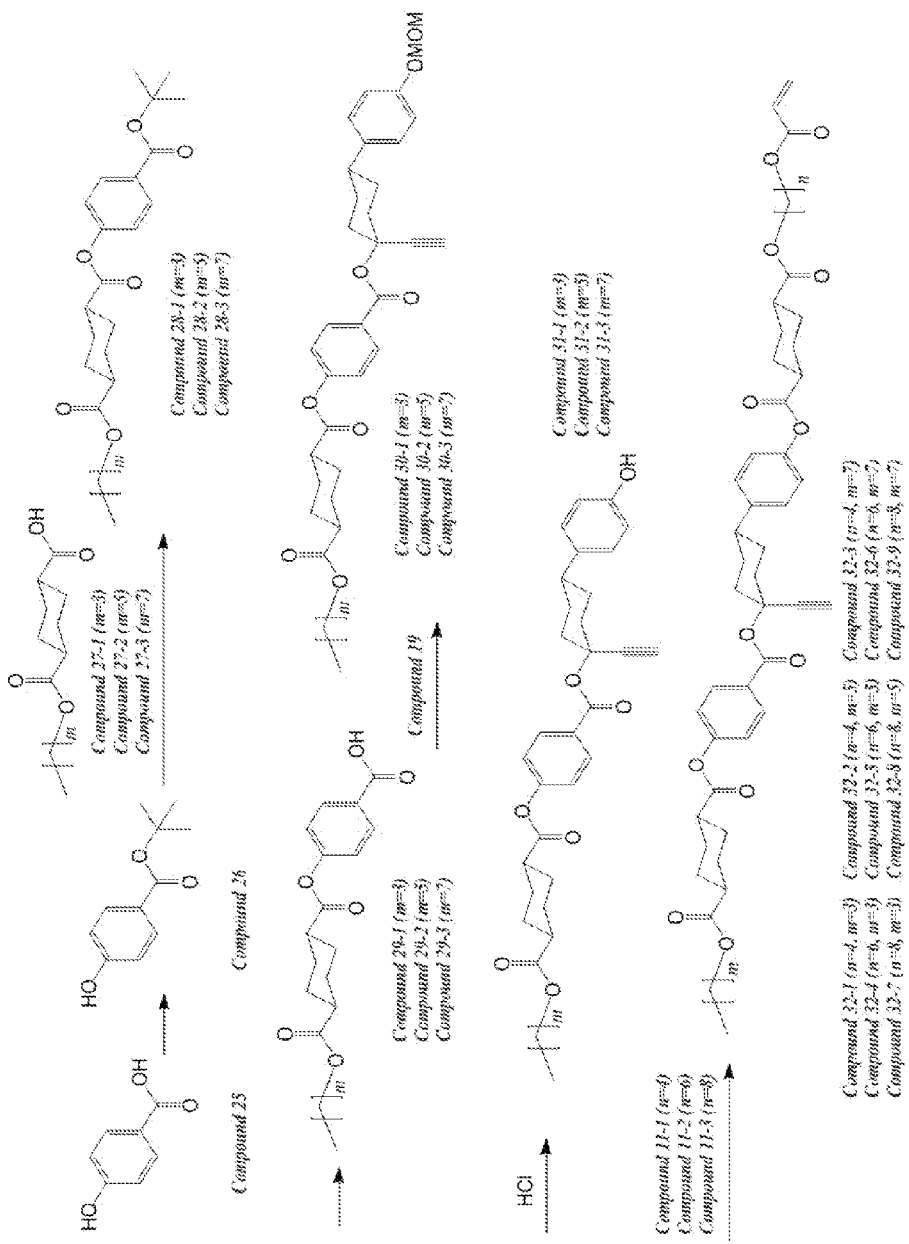
Figure 3B:
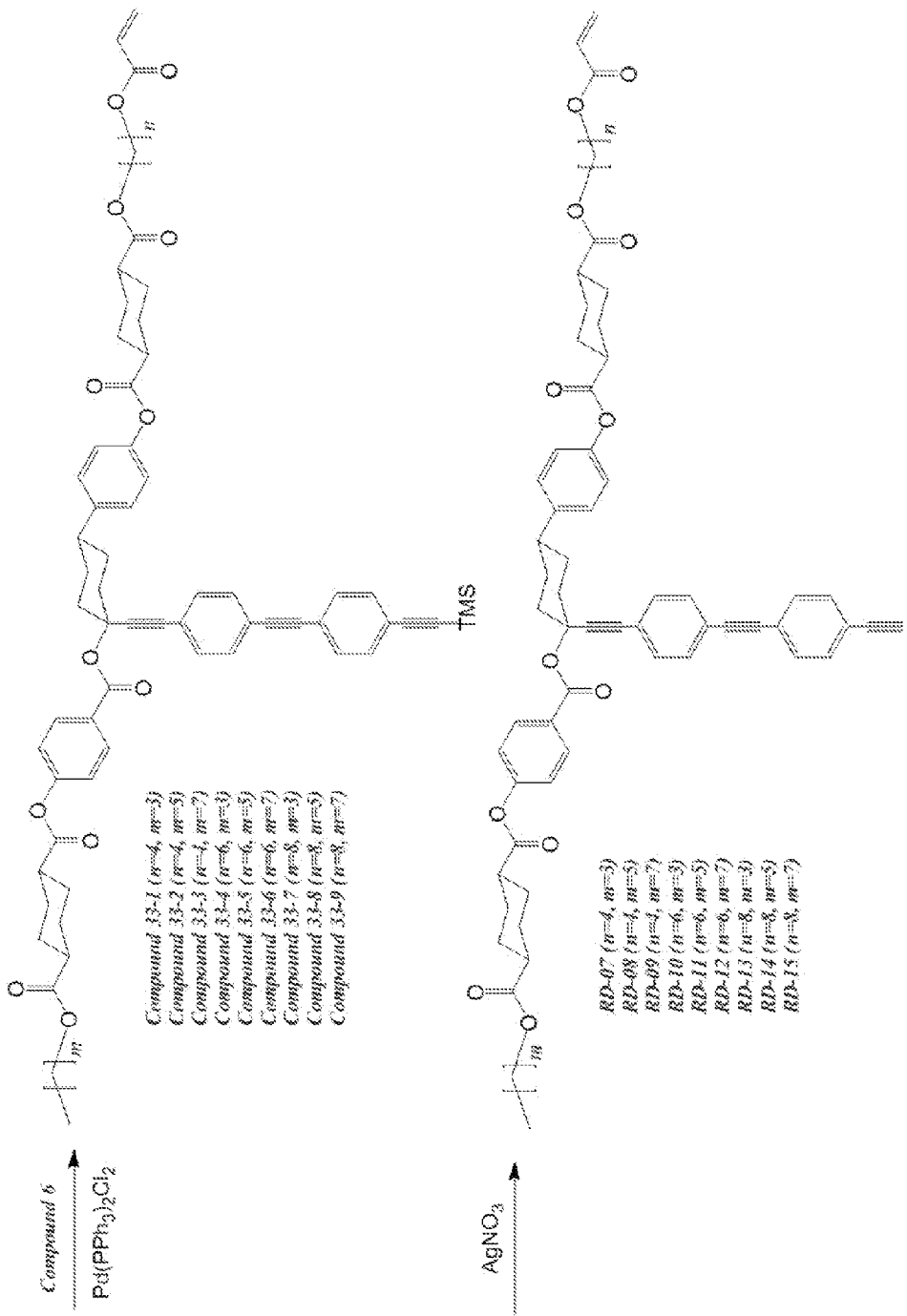

Compound RD-07 was synthesized according to the scheme shown in FIGS. 3a and 3b.

Synthesis of Compound 26

After dissolving about 100 g of Compound 25 (4-hydroxybenzoic acid), about 100 g of N,N'-dicyclohexylcarbodiimide, about 10 g of 4-(dimethylamino)pyridine, and about 20 g of tert-butanol in tetrahydrofuran, the mixture was stirred for about 24 h. Then, the reacted product was extracted with dichloromethane and water, and about 80 g of Compound 26 was obtained by chemically drying the extracted organic layer and refining the same with column chromatography.

Synthesis of Compound 28-1

After dissolving about 60 g of Compound 26, about 50 g of Compound 27-1 [(1 r,4r)-4-(butoxycarbonyl)cyclohexanecarboxylic acid], about 5 g of 4-(dimethylamino)pyridine, and about 50 g of N,N-diisopropylethylamine in dichloromethane, the mixture was stirred for about 30 min. After adding about 80 g of 1-ethyl-3-(3-dimethylaminopropyl) carbodiimide and about 50 g of ethynyltrimethylsilane thereto and stirring the same for about 24 h, the obtained product was extracted with dichloromethane and water. Then, about 80 g of Compound 28-1 was obtained by chemically drying the extracted organic layer and refining the same with column chromatography.

Synthesis of Compound 29-1

After dissolving about 80 g of Compound 28-1 and about 50 g of tetrafluoroacetic acid in dichloromethane, the mixture was stirred for about 24 h. Then, the reacted product was extracted with dichloromethane and water, and about 60 g of Compound 29-1 was obtained by chemically drying the extracted organic layer and refining the same with column chromatography.

Synthesis of Compound 30-1

After dissolving about 60 g of Compound 29-1, about 50 g of Compound of Example 4, and about 50 g of 4-(dimethylamino)pyridine in dichloromethane, the mixture was stirred for about 30 min. After adding about 80 g of 1-ethyl-3-(3-dimethylaminopropyl)carbodiimide thereto and stirring the same for about 24 h, the obtained product was extracted with dichloromethane and water. Then, about 80 g of Compound 30-1 was obtained by chemically drying the extracted organic layer and refining the same with column chromatography.

Synthesis of Compound 31-1

After dissolving about 80 g of Compound 30-1 and about 300 ml of 6N hydrochloric acid in tetrahydrofuran, the mixture was stirred for about 24 h at about 40° C. Then, the reacted product was extracted with dichloromethane and water, and about 60 g of Compound 31-1 (m=3) was obtained by chemically drying the extracted organic layer and refining the same with column chromatography.

Synthesis of Compound 32-1

About 80 g of Compound 32-1 was obtained by the same method as the synthesis of Compound 12-1 of Example 1, except that Compound 31-1 (m=3) was used instead of Compound 10.

Synthesis of Compound 33-1

About 70 g of Compound 33-1 was obtained by the same method as the synthesis of Compound 15-1 of Example 1, except that Compound 32-1 was used instead of Compound 14-1.

Synthesis of Compound RD-07

About 30 g of Compound RD-07 was obtained by the same method as the synthesis of Compound RD-01 of Example 1, except that Compound 33-1 was used instead of Compound 15-1.

The NMR spectrum of the obtained Compound RD-07 is as follows.

$^1$H NMR (CDCl$_3$, standard material TMS) δ(ppm): 8.04 (2H, s), 7.56 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (25H, m)

Example 8: Synthesis of Compound RD-08

Synthesis of Compound 30-2

About 90 g of Compound 30-2 was obtained by the same method as the synthesis of Compound 30-1 of Example 7, except that Compound 29-2 was used instead of Compound 29-1.

Synthesis of Compound 31-2

About 70 g of Compound 31-2 (m=5) was obtained by the same method as the synthesis of Compound 31-1 of Example 7, except that Compound 30-2 was used instead of Compound 30-1.

Synthesis of Compound 32-2

About 80 g of Compound 32-2 was obtained by the same method as the synthesis of Compound 12-1 of Example 1, except that Compound 31-2 (m=5) was used instead of Compound 10.

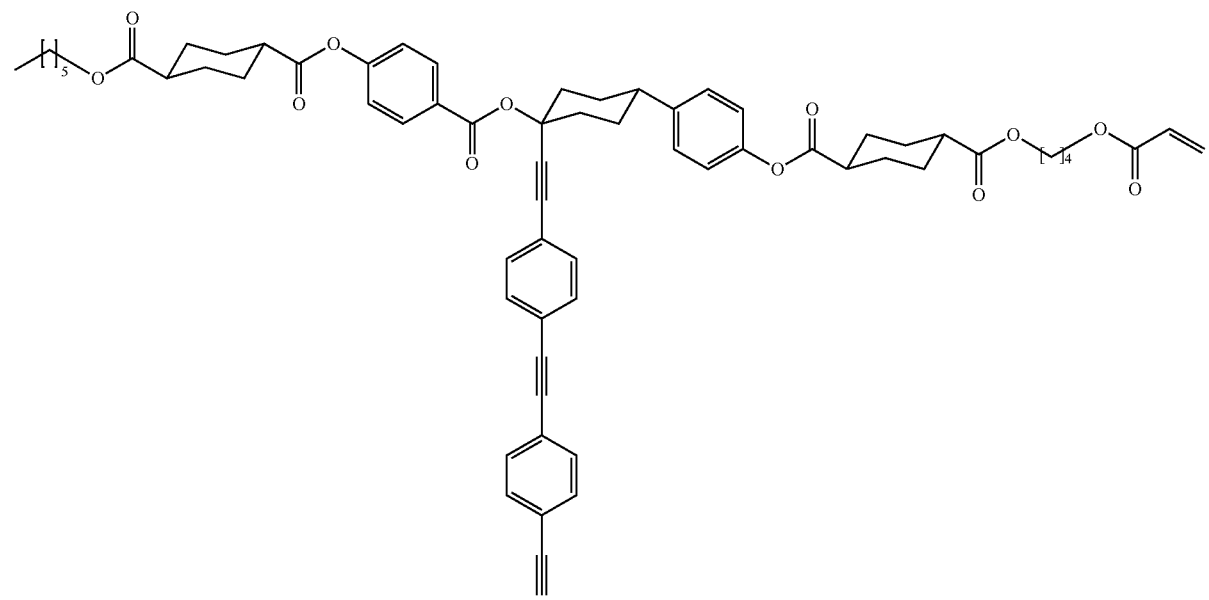

RD-08

Compound RD-08 was synthesized according to the scheme shown in FIGS. 3a and 3b.

Synthesis of Compound 28-2

About 100 g of Compound 28-2 was obtained by the same method as the synthesis of Compound 28-1 of Example 7, except that Compound 27-2 [(1 r,4r)-4-((hexyloxy)carbonyl)cyclohexanecarboxylic acid] was used instead of Compound 27-1.

Synthesis of Compound 29-2

About 70 g of Compound 29-2 was obtained by the same method as the synthesis of Compound 29-1 of Example 7, except that Compound 28-2 was used instead of Compound 28-1.

Synthesis of Compound 33-2

About 70 g of Compound 33-2 was obtained by the same method as the synthesis of Compound 15-1 of Example 1, except that Compound 32-2 was used instead of Compound 14-1.

Synthesis of Compound RD-08

About 30 g of Compound RD-08 was obtained by the same method as the synthesis of Compound RD-01 of Example 1, except that Compound 33-2 was used instead of Compound 15-1.

The NMR spectrum of the obtained Compound RD-08 is as follows.

$^1$H NMR (CDCl$_3$, standard material TMS) δ(ppm): 8.04 (2H, s), 7.56 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (29H, m)

Example 9: Synthesis of Compound RD-09

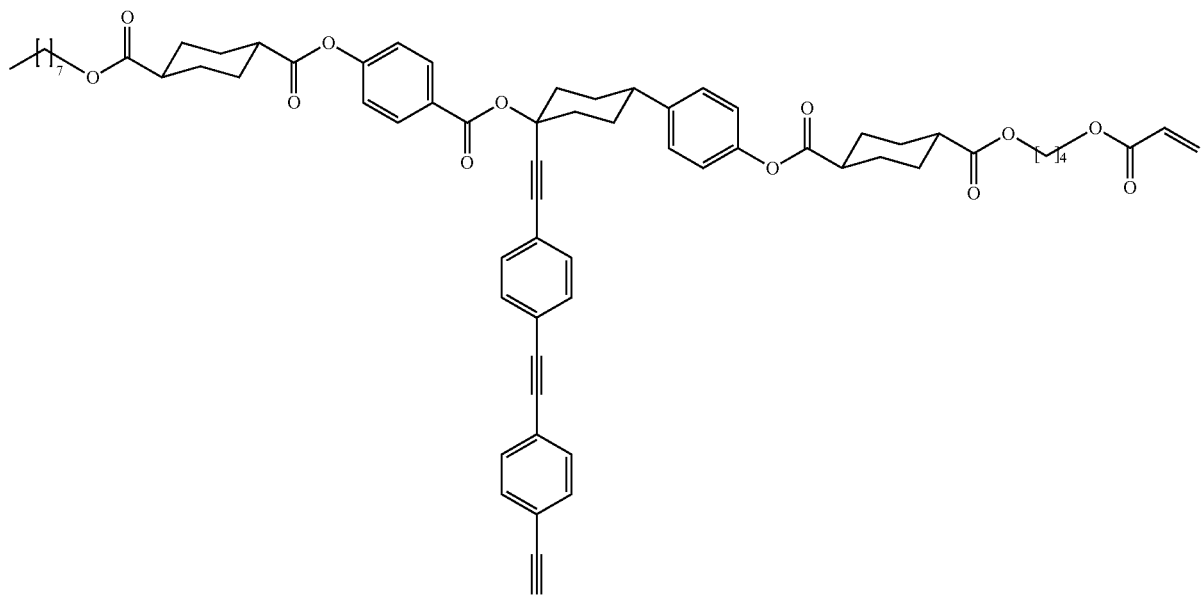

RD-09

Compound RD-09 was synthesized according to the scheme shown in FIGS. 3a and 3b.

Synthesis of Compound 28-3

About 100 g of Compound 28-3 was obtained by the same method as the synthesis of Compound 28-1 of Example 7, except that Compound 27-3 [(1 r,4r)-4-((octyloxy)carbonyl)cyclohexanecarboxylic acid] was used instead of Compound 27-1.

Synthesis of Compound 29-3

About 70 g of Compound 29-3 was obtained by the same method as the synthesis of Compound 29-1 of Example 7, except that Compound 28-3 was used instead of Compound 28-1.

Synthesis of Compound 30-3

About 90 g of Compound 30-3 was obtained by the same method as the synthesis of Compound 30-1 of Example 7, except that Compound 29-3 was used instead of Compound 29-1.

Synthesis of Compound 31-3

About 70 g of Compound 31-3 (m=7) was obtained by the same method as the synthesis of Compound 31-1 of Example 7, except that Compound 30-3 was used instead of Compound 30-1.

Synthesis of Compound 32-3

About 80 g of Compound 32-3 was obtained by the same method as the synthesis of Compound 12-1 of Example 1, except that Compound 31-3 (m=7) was used instead of Compound 10.

Synthesis of Compound 33-3

About 70 g of Compound 33-3 was obtained by the same method as the synthesis of Compound 15-1 of Example 1, except that Compound 32-3 was used instead of Compound 14-1.

Synthesis of Compound RD-09

About 30 g of Compound RD-09 was obtained by the same method as the synthesis of Compound RD-01 of Example 1, except that Compound 33-3 was used instead of Compound 15-1.

The NMR spectrum of the obtained Compound RD-09 is as follows.

$^1$H NMR (CDCl$_3$, standard material TMS) δ(ppm): 8.04 (2H, s), 7.56 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (33H, m)

Example 10: Synthesis of Compound RD-10

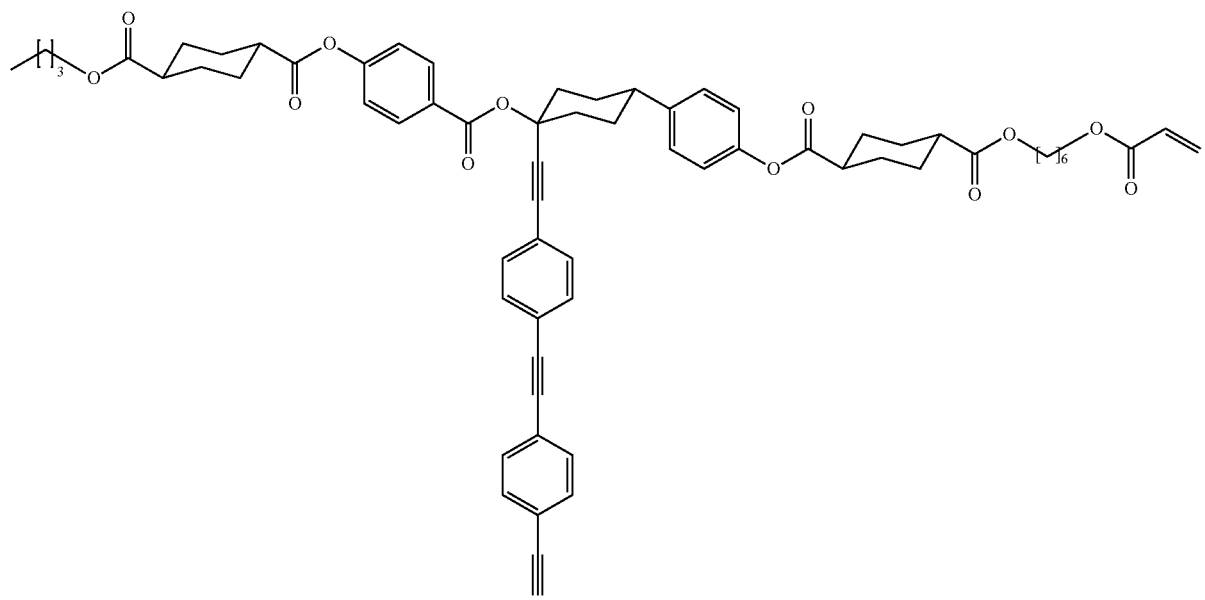

RD-10

Compound RD-10 was synthesized according to the scheme shown in FIGS. 3a and 3b.

Synthesis of Compound 32-4

About 80 g of Compound 32-4 was obtained by the same method as the synthesis of Compound 12-1 of Example 1, except that Compound 31-1 (m=3) was used instead of Compound 10 and Compound 11-2 (n=6) [(1r,4r)-4-(((6-(acryloyloxy)hexyl)oxy)carbonyl)cyclohexanecarboxylic acid] was used instead of Compound 11-1.

Synthesis of Compound 33-4

About 60 g of Compound 33-4 was obtained by the same method as the synthesis of Compound 15-1 of Example 1, except that Compound 32-4 was used instead of Compound 14-1.

Synthesis of Compound RD-10

About 50 g of Compound RD-10 was obtained by the same method as the synthesis of Compound RD-01 of Example 1, except that Compound 33-4 was used instead of Compound 15-1.

The NMR spectrum of the obtained Compound RD-10 is as follows.

$^1$H NMR (CDCl$_3$, standard material TMS) δ(ppm): 8.04 (2H, s), 7.56 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (29H, m)

Example 11: Synthesis of Compound RD-11

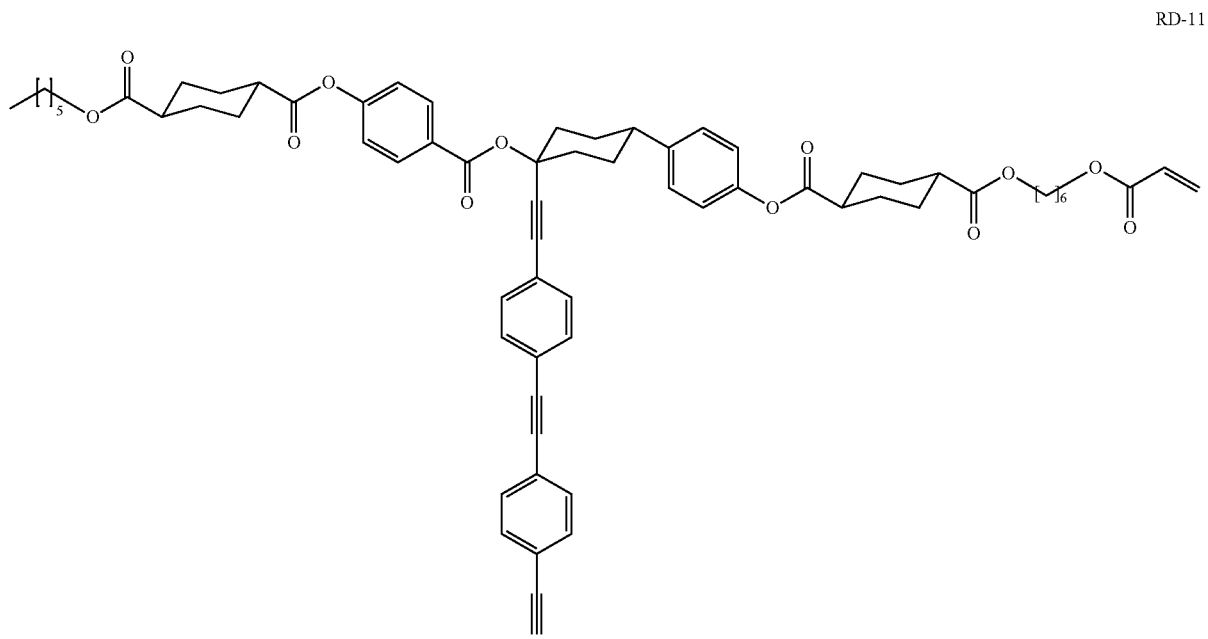

RD-11

Compound RD-11 was synthesized according to the scheme shown in FIGS. 3a and 3b.

Synthesis of Compound 32-5

About 80 g of Compound 32-5 was obtained by the same method as the synthesis of Compound 12-1 of Example 1, except that Compound 31-2 (m=5) was used instead of Compound 10 and Compound 11-2 (n=6) [(1r,4r)-4-(((6-(acryloyloxy)hexyl)oxy)carbonyl)cyclohexanecarboxylic acid] was used instead of Compound 11-1.

Synthesis of Compound 33-5

About 60 g of Compound 33-5 was obtained by the same method as the synthesis of Compound 15-1 of Example 1, except that Compound 32-5 was used instead of Compound 14-1.

Synthesis of Compound RD-11

About 50 g of Compound RD-11 was obtained by the same method as the synthesis of Compound RD-01 of Example 1, except that Compound 33-5 was used instead of Compound 15-1.

The NMR spectrum of the obtained Compound RD-11 is as follows.

$^1$H NMR (CDCl$_3$, standard material TMS) δ(ppm): 8.04 (2H, s), 7.56 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (33H, m)

Example 12: Synthesis of Compound RD-12

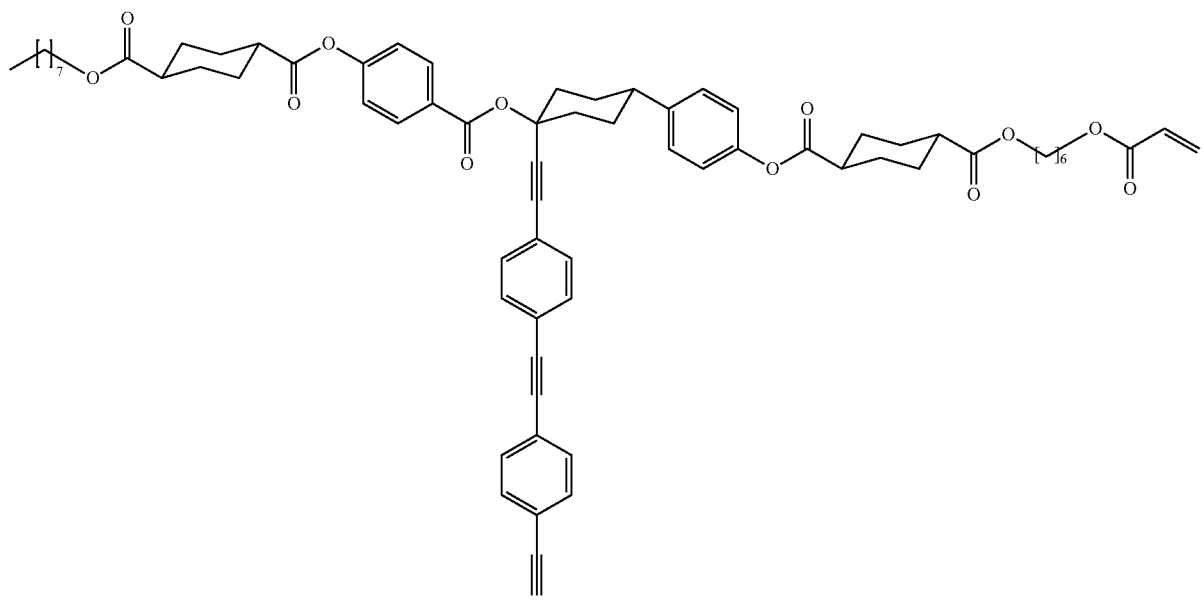

RD-12

Compound RD-12 was synthesized according to the scheme shown in FIGS. 3a and 3b.

Synthesis of Compound 32-6

About 80 g of Compound 32-6 was obtained by the same method as the synthesis of Compound 12-1 of Example 1, except that Compound 31-3 (m=7) was used instead of Compound 10 and Compound 11-2 (n=6) [(1r,4r)-4-(((6-(acryloyloxy)hexyl)oxy)carbonyl)cyclohexanecarboxylic acid] was used instead of Compound 11-1.

Synthesis of Compound 33-6

About 60 g of Compound 33-6 was obtained by the same method as the synthesis of Compound 15-1 of Example 1, except that Compound 32-6 was used instead of Compound 14-1.

Synthesis of Compound RD-12

About 50 g of Compound RD-12 was obtained by the same method as the synthesis of Compound RD-01 of Example 1, except that Compound 33-6 was used instead of Compound 15-1.

The NMR spectrum of the obtained Compound RD-12 is as follows.

$^1$H NMR (CDCl$_3$, standard material TMS) δ(ppm): 8.04 (2H, s), 7.56 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (37H, m)

Example 13: Synthesis of Compound RD-13

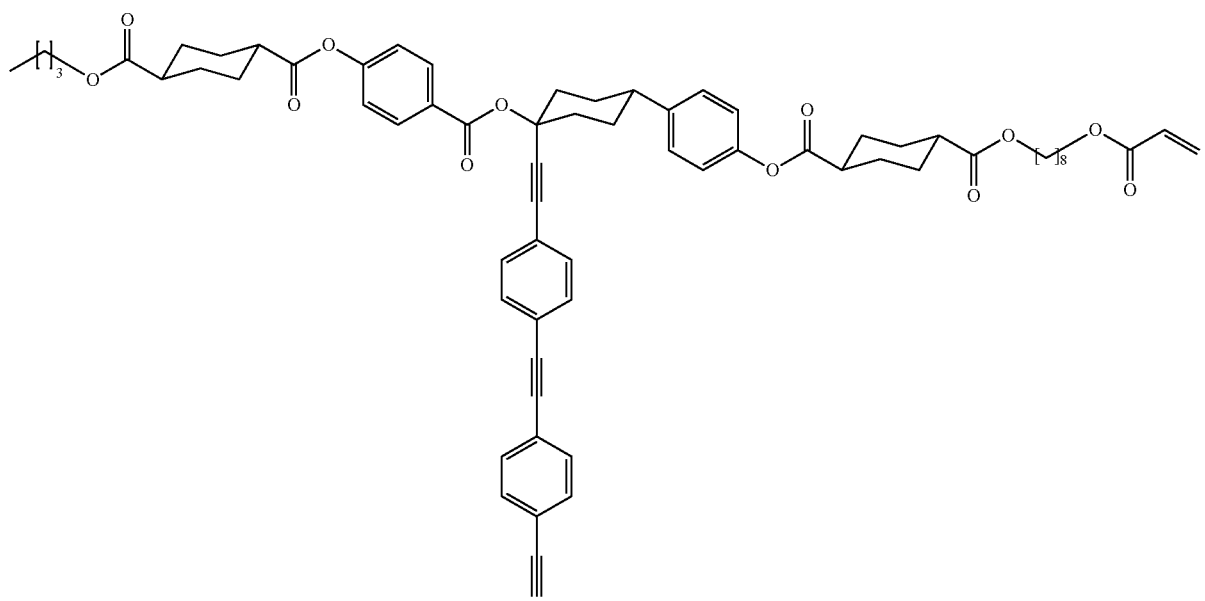

Compound RD-13 was synthesized according to the scheme shown in FIGS. 3a and 3b.

Synthesis of Compound 32-7

About 80 g of Compound 32-7 was obtained by the same method as the synthesis of Compound 12-1 of Example 1, except that Compound 31-1 (m=3) was used instead of Compound 10 and Compound 11-3 (n=8) [(1r,4r)-4-(((8-(acryloyloxy)octyl)oxy)carbonyl)cyclohexanecarboxylic acid] was used instead of Compound 11-1.

Synthesis of Compound 33-7

About 60 g of Compound 33-7 was obtained by the same method as the synthesis of Compound 15-1 of Example 1, except that Compound 32-7 was used instead of Compound 14-1.

Synthesis of Compound RD-13

About 50 g of Compound RD-13 was obtained by the same method as the synthesis of Compound RD-01 of Example 1, except that Compound 33-7 was used instead of Compound 15-1.

The NMR spectrum of the obtained Compound RD-13 is as follows.

$^1$H NMR (CDCl$_3$, standard material TMS) δ(ppm): 8.04 (2H, s), 7.56 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (33H, m)

Example 14: Synthesis of Compound RD-14

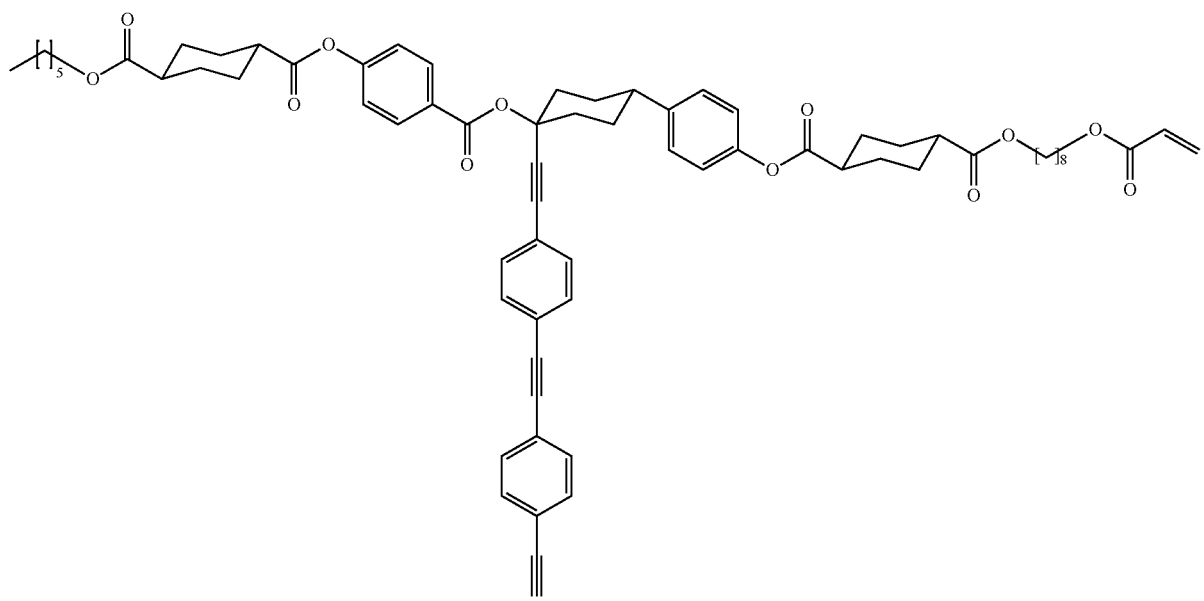

Compound RD-14 was synthesized according to the scheme shown in FIGS. 3a and 3b.

Synthesis of Compound 32-8

About 80 g of Compound 32-8 was obtained by the same method as the synthesis of Compound 12-1 of Example 1, except that Compound 31-2 (m=5) was used instead of Compound 10 and Compound 11-3 (n=8) [(1r,4r)-4-(((8-(acryloyloxy)octyl)oxy)carbonyl)cyclohexanecarboxylic acid] was used instead of Compound 11-1.

Synthesis of Compound 33-8

About 60 g of Compound 33-8 was obtained by the same method as the synthesis of Compound 15-1 of Example 1, except that Compound 32-8 was used instead of Compound 14-1.

Synthesis of Compound RD-14

About 50 g of Compound RD-14 was obtained by the same method as the synthesis of Compound RD-01 of Example 1, except that Compound 33-8 was used instead of Compound 15-1.

The NMR spectrum of the obtained Compound RD-14 is as follows.

$^1$H NMR (CDCl$_3$, standard material TMS) δ(ppm): 8.04 (2H, s), 7.56 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (37H, m)

Example 15: Synthesis of Compound RD-15

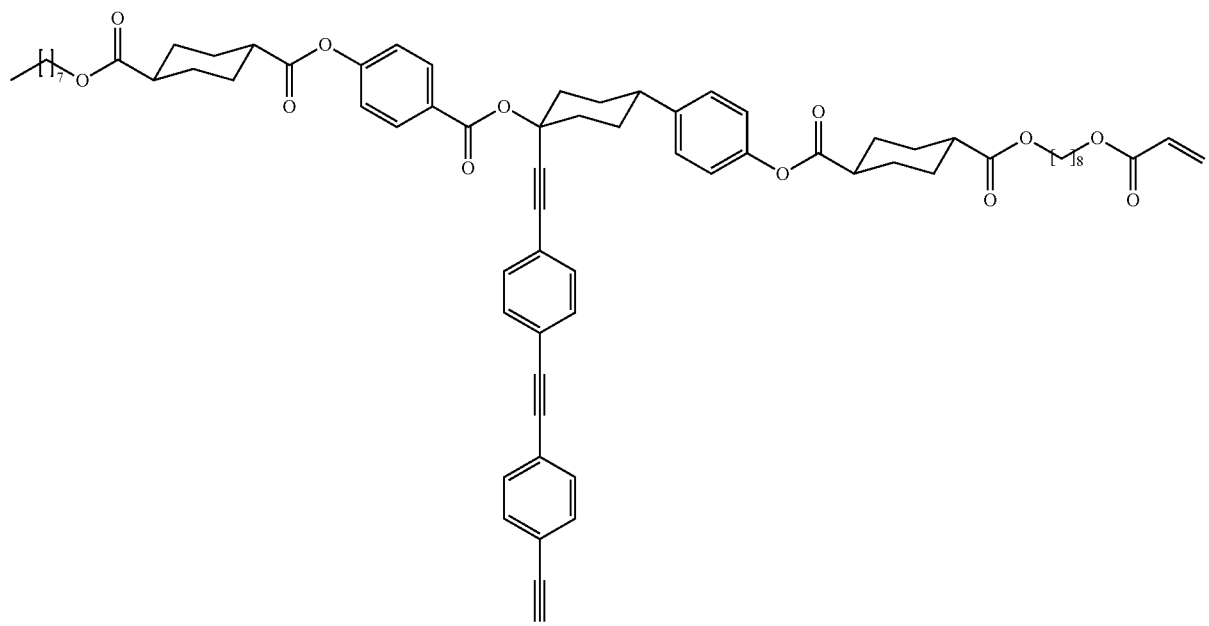

Compound RD-15 was synthesized according to the scheme shown in FIGS. 3a and 3b.

Synthesis of Compound 32-9

About 80 g of Compound 32-9 was obtained by the same method as the synthesis of Compound 12-1 of Example 1, except that Compound 31-3 (m=7) was used instead of Compound 10 and Compound 11-3 (n=8) [(1r,4r)-4-(((8-(acryloyloxy)octyl)oxy)carbonyl)cyclohexanecarboxylic acid] was used instead of Compound 11-1.

Synthesis of Compound 33-9

About 60 g of Compound 33-9 was obtained by the same method as the synthesis of Compound 15-1 of Example 1, except that Compound 32-9 was used instead of Compound 14-1.

Synthesis of Compound RD-15

About 50 g of Compound RD-15 was obtained by the same method as the synthesis of Compound RD-01 of Example 1, except that Compound 33-9 was used instead of Compound 15-1.

The NMR spectrum of the obtained Compound RD-15 is as follows.

$^1$H NMR (CDCl$_3$, standard material TMS) δ(ppm): 8.04 (2H, s), 7.56 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (41H, m)

Example 16: Synthesis of Compound RD-16

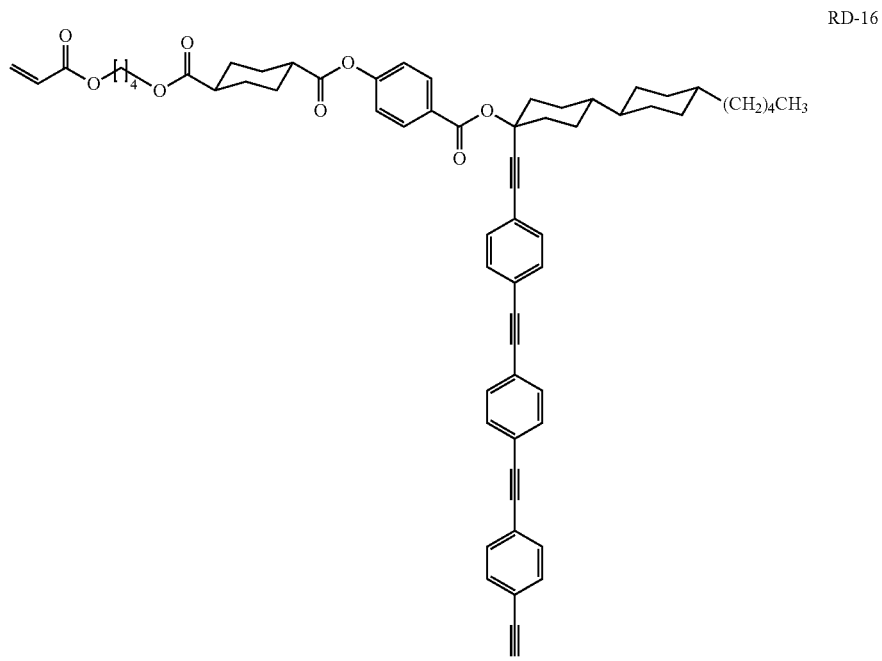

Figure 4A:
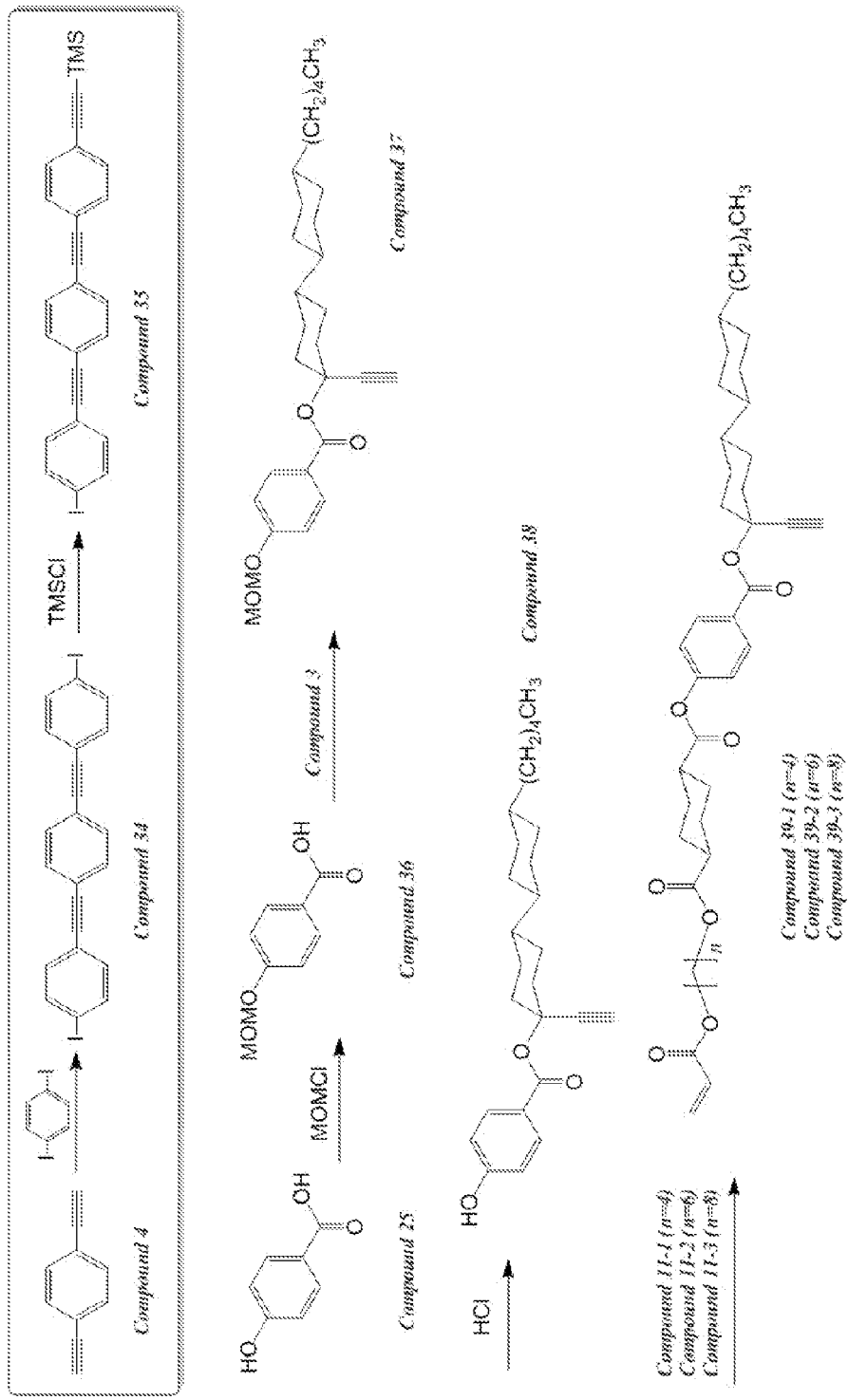
Figure 4B:
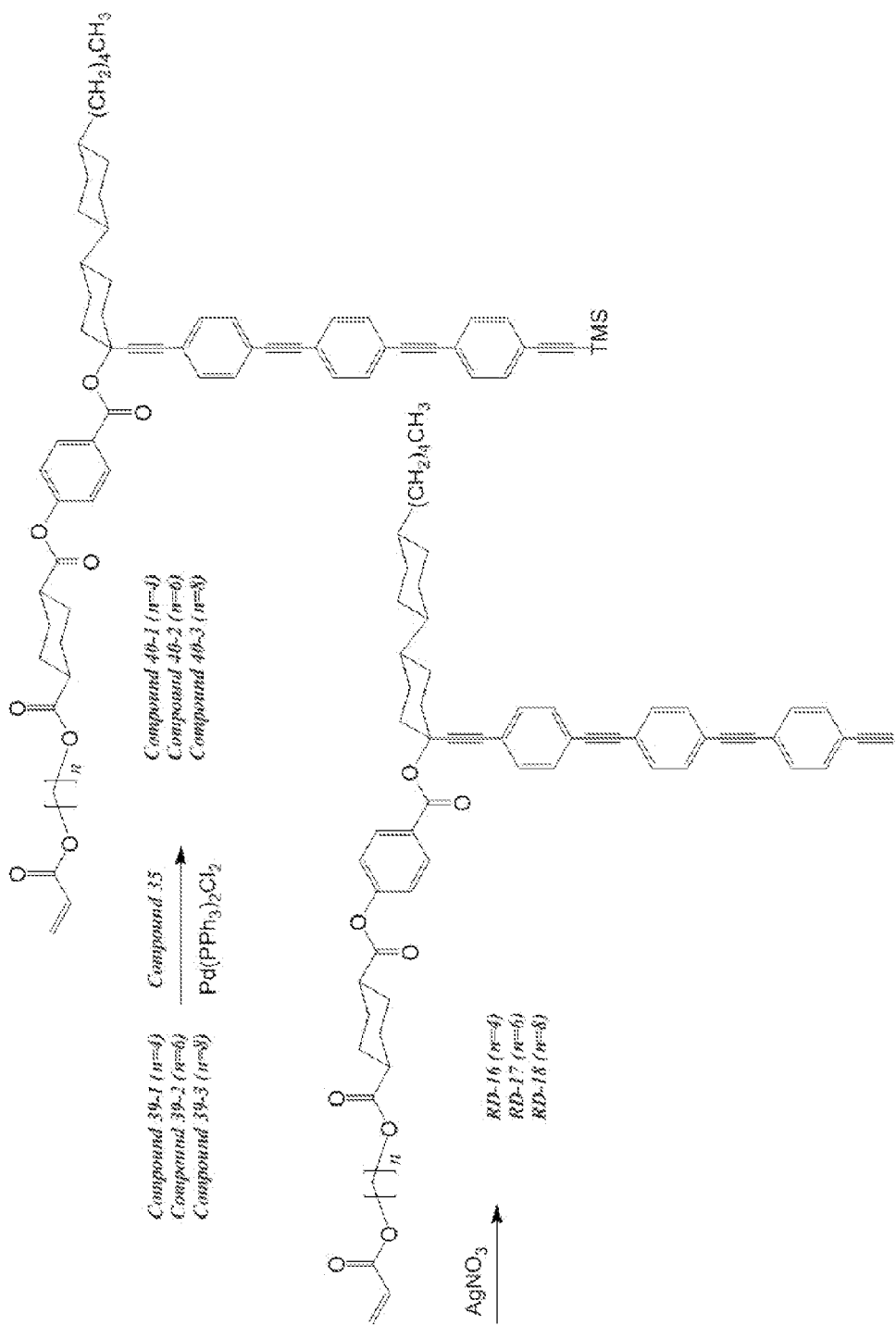

Compound RD-16 was synthesized according to the scheme shown in FIGS. 4a and 4b.

Synthesis of Compound 34

After dissolving about 200 g of 1,4-diiodobenzene, about 3 g of Pd(PPh$_3$)$_2$Cl$_2$ (bis(triphenylphosphine)palladium(II) dichloride), about 5 g of CuI (copper iodide), and about 200 ml of N,N-diisopropylethylamine in tetrahydrofuran, about 50 g of Compound 4 (1,4-diethynylbenzene) dissolved in tetrahydrofuran was slowly added thereto dropwise. After refluxing and stirring the mixture for about 24 h, the produced salt was filtered and eliminated therefrom and the obtained product was extracted with dichloromethane and water. About 100 g of Compound 34 was obtained by chemically drying the extracted organic layer and refining the same with column chromatography.

Synthesis of Compound 35

After dissolving about 100 g of Compound 34 in tetrahydrofuran, the mixture was stirred for about 20 min at about −78° C. About 500 ml of n-butyl lithium in 2.5M hexane was added thereto dropwise for about 2 h. After stirring the same for about 4 h, about 100 ml of chlorotrimethylsilane was added thereto and the mixture was stirred for about 24 h. Then, the reacted product was extracted with ethyl acetate and water, and about 60 g of Compound 35 was obtained by chemically drying the obtained organic layer, and refining the same with column chromatography.

Synthesis of Compound 36

After dissolving 100 g of Compound 25 (4-hydroxybenzoic acid) and about 400 g of N,N-diisopropylethylamine in dichloromethane, about 200 g of methylchloromethylether was slowly added thereto dropwise at about 0° C. After stirring the mixture for about 24 h, the product was washed with about 500 ml of ammonium chloride and extracted with dichloromethane and water. The extracted organic layer was chemically dried and the solvent was eliminated therefrom. The product obtained in this way and a potassium hydroxide aqueous solution were put in methanol and the solution was refluxed and stirred for about 3 h. The product was extracted by adding 6N hydrochloric acid thereto and then the solvent was eliminated therefrom by filtering the same. Then, about 110 g of Compound 36 was obtained by eliminating extra foreign substances therefrom by using hexane, and drying the same for about 48 h.

Synthesis of Compound 37

After dissolving about 100 g of Compound 36, about 100 g of Compound 3 of Example 1, and about 70 g of 4-(dimethylamino)pyridine in dichloromethane, the mixture was stirred for about 30 min. After adding about 80 g of 1-ethyl-3-(3-dimethylaminopropyl)carbodiimide thereto and stirring the same for about 24 h, the obtained product was extracted with dichloromethane and water. Then, about 150 g of Compound 37 was obtained by chemically drying the extracted organic layer and refining the same with column chromatography.

Synthesis of Compound 38

After dissolving about 100 g of Compound 37 and about 300 ml of 6N hydrochloric acid in tetrahydrofuran, the mixture was stirred for about 24 h at about 40° C. Then, the reacted product was extracted with dichloromethane and water, and about 80 g of Compound 38 was obtained by chemically drying the extracted organic layer and refining the same with column chromatography.

Synthesis of Compound 39-1

About 100 g of Compound 39-1 was obtained by the same method as the synthesis of Compound 12-1 of Example 1, except that Compound 38 was used instead of Compound 10.

Synthesis of Compound 40-1

About 30 g of Compound 40-1 was obtained by the same method as the synthesis of Compound 15-1 of Example 1, except that Compound 39-1 was used instead of Compound 14-1 and Compound 35 was used instead of Compound 6.

Synthesis of Compound RD-16

About 20 g of Compound RD-16 was obtained by the same method as the synthesis of Compound RD-01 of Example 1, except that Compound 40-1 was used instead of Compound 15-1.

The NMR spectrum of the obtained Compound RD-16 is as follows.

$^1$H NMR (CDCl$_3$, standard material TMS) δ(ppm): 8.04 (2H, d), 7.56 (4H, d), 7.55 (4H, d), 7.51 (4H, d), 7.40 (2H, d), 6.27 (1H, d), 6.05 (1H, dd), 5.59 (1H, d), 4.13 (2H, t), 4.05 (1H, s), 3.97 (2H, t), 3.52 (1H, s), 1.60-1.12 (48H, m)

Example 17: Synthesis of Compound RD-17

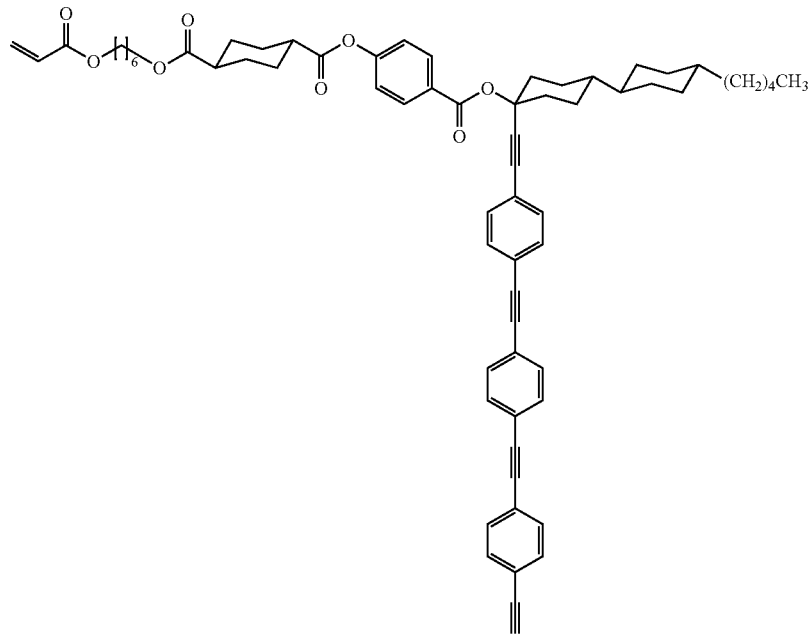

RD-17

Compound RD-17 was synthesized according to the scheme shown in FIGS. 4a and 4b.

Synthesis of Compound 39-2

About 100 g of Compound 39-2 was obtained by the same method as the synthesis of Compound 12-1 of Example 1, except that Compound 38 was used instead of Compound 10 and Compound 11-2 (n=6) [(1r,4r)-4-(((6-(acryloyloxy)hexyl)oxy)carbonyl)cyclohexanecarboxylic acid] was used instead of Compound 11-1.

Synthesis of Compound 40-2

About 70 g of Compound 40-2 was obtained by the same method as the synthesis of Compound 15-1 of Example 1, except that Compound 39-2 was used instead of Compound 14-1 and Compound 35 was used instead of Compound 6.

Synthesis of Compound RD-17

About 50 g of Compound RD-17 was obtained by the same method as the synthesis of Compound RD-01 of Example 1, except that Compound 40-2 was used instead of Compound 15-1.

The NMR spectrum of the obtained Compound RD-17 is as follows.

$^1$H NMR (CDCl$_3$, standard material TMS) δ(ppm): 8.04 (2H, d), 7.56 (4H, d), 7.55 (4H, d), 7.51 (4H, d), 7.40 (2H, d), 6.27 (1H, d), 6.05 (1H, dd), 5.59 (1H, d), 4.13 (2H, t), 4.05 (1H, s), 3.97 (2H, t), 3.52 (1H, s), 1.60-1.12 (52H, m)

Example 18: Synthesis of Compound RD-18

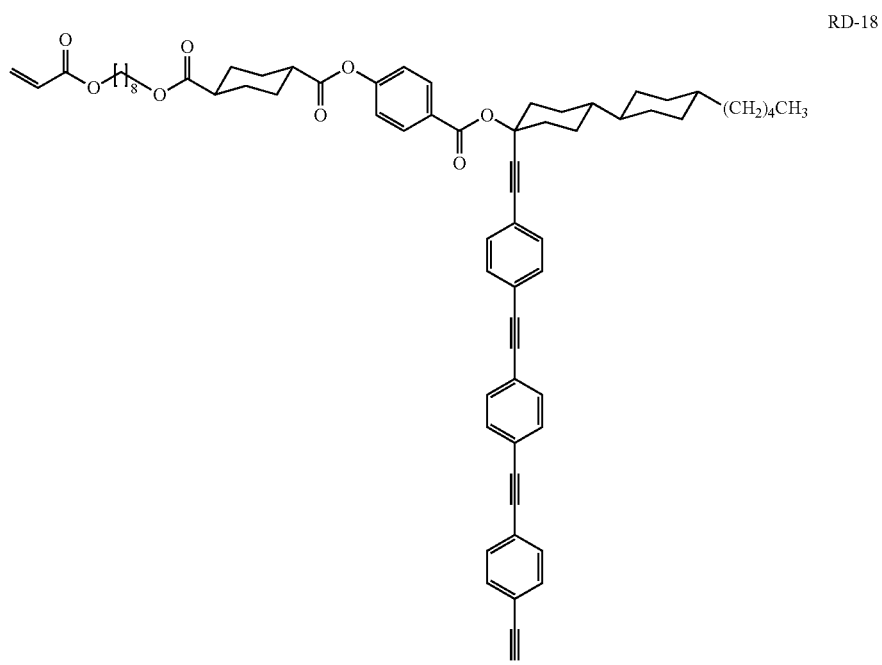

Compound RD-18 was synthesized according to the scheme shown in FIGS. 4a and 4b.

Synthesis of Compound 39-3

About 100 g of Compound 39-3 was obtained by the same method as the synthesis of Compound 12-1 of Example 1, except that Compound 38 was used instead of Compound 10 and Compound 11-3 (n=8) [(1r,4r)-4-(((8-(acryloyloxy)octyl)oxy)carbonyl)cyclohexanecarboxylic acid] was used instead of Compound 11-1.

Synthesis of Compound 40-3

About 70 g of Compound 40-3 was obtained by the same method as the synthesis of Compound 15-1 of Example 1, except that Compound 39-3 was used instead of Compound 14-1 and Compound 35 was used instead of Compound 6.

Synthesis of Compound RD-18

About 50 g of Compound RD-18 was obtained by the same method as the synthesis of Compound RD-01 of Example 1, except that Compound 40-3 was used instead of Compound 15-1.

The NMR spectrum of the obtained Compound RD-18 is as follows.

$^1$H NMR (CDCl$_3$, standard material TMS) δ(ppm): 8.04 (2H, d), 7.56 (4H, d), 7.55 (4H, d), 7.51 (4H, d), 7.40 (2H, d), 6.27 (1H, d), 6.05 (1H, dd), 5.59 (1H, d), 4.13 (2H, t), 4.05 (1H, s), 3.97 (2H, t), 3.52 (1H, s), 1.60-1.12 (56H, m)

Example 19: Synthesis of Compound RD-19

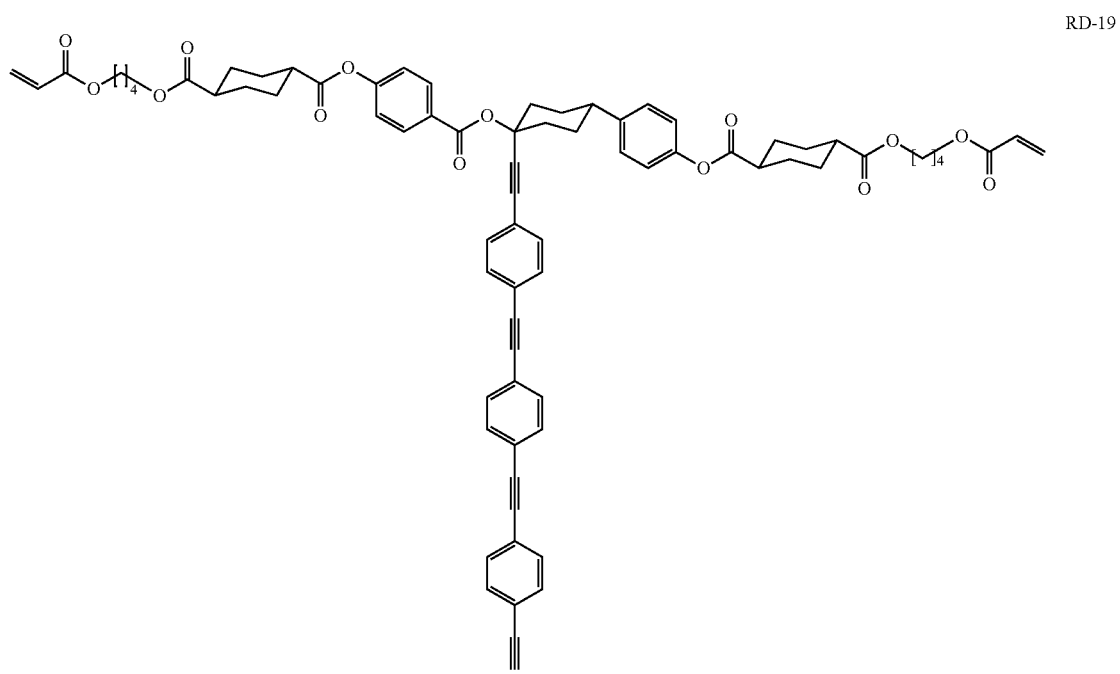

Figure 5A:
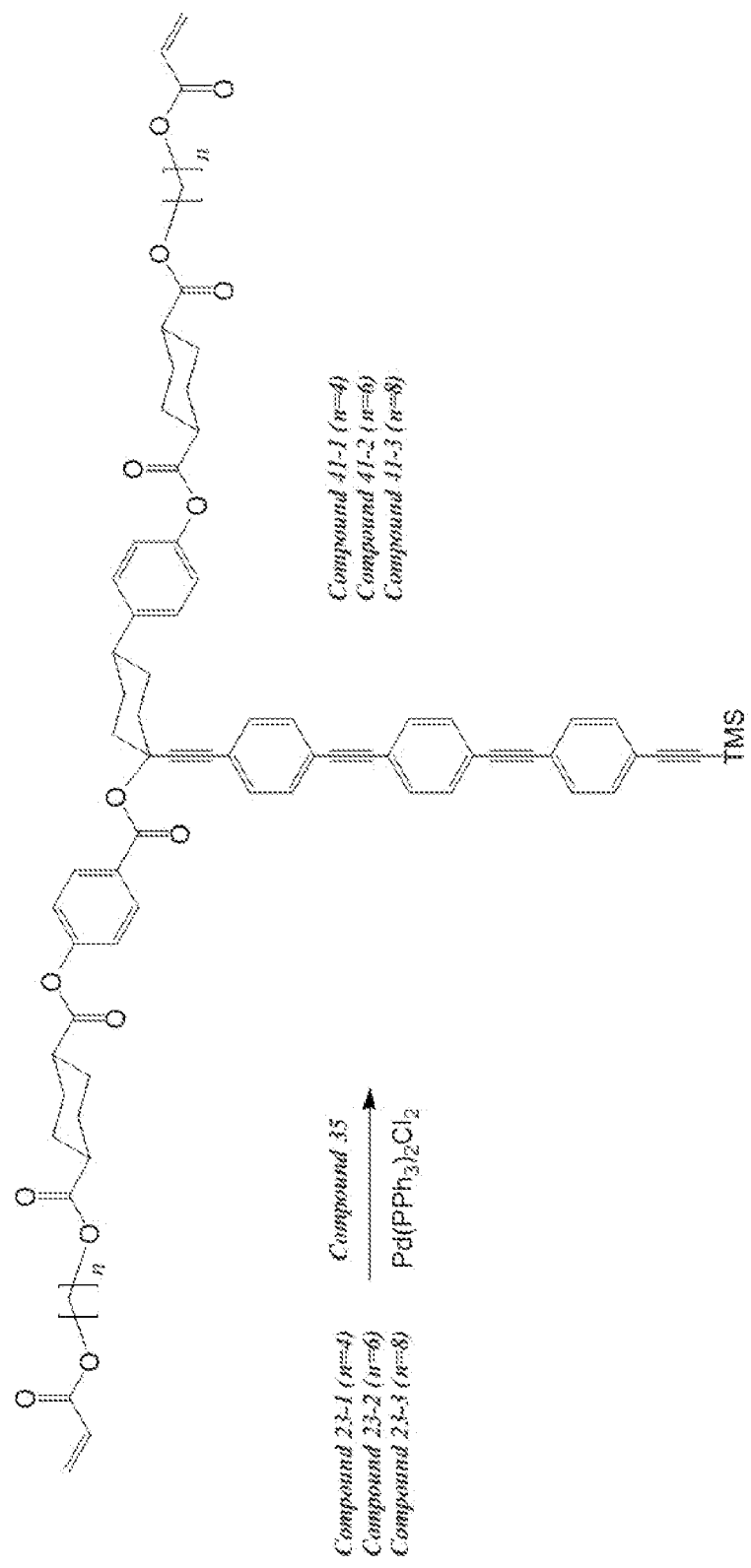
Figure 5B:
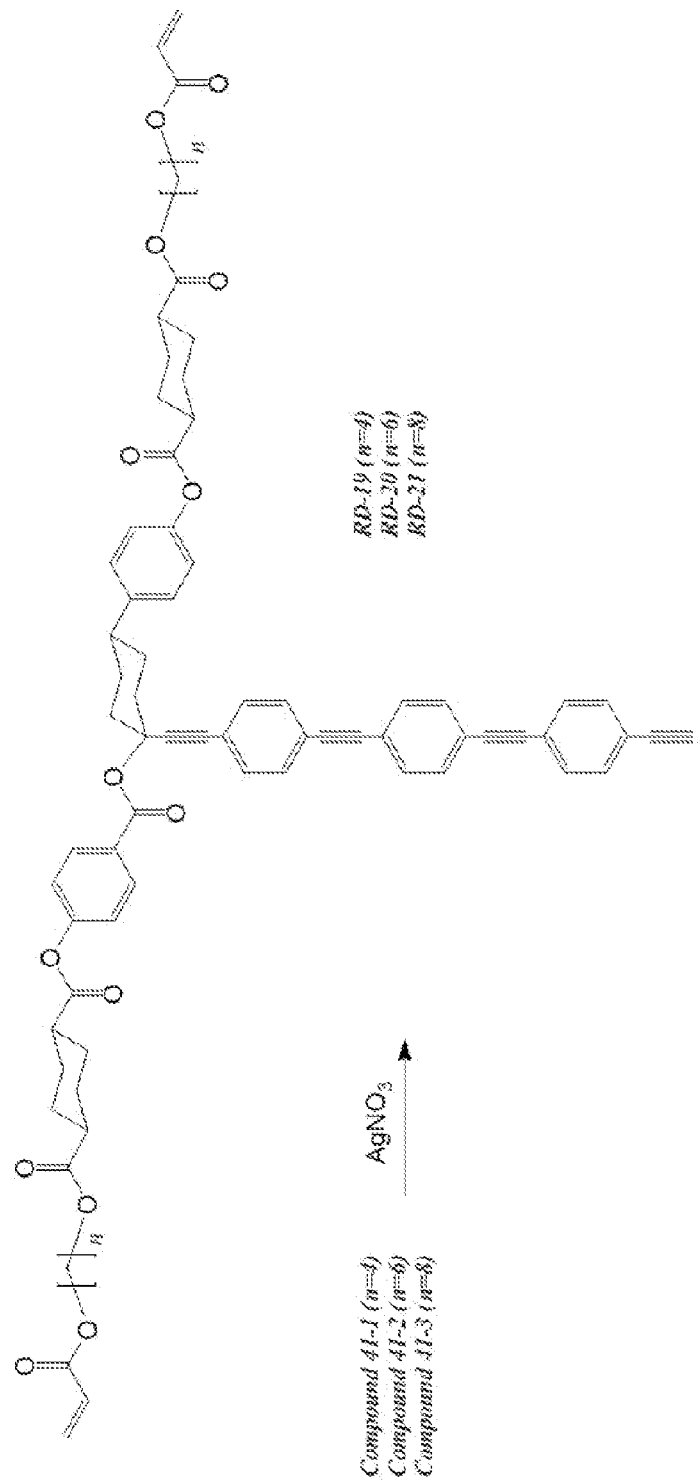

Compound RD-19 was synthesized according to the scheme shown in FIGS. 5a and 5b.

Synthesis of Compound 41-1

About 70 g of Compound 41-1 was obtained by the same method as the synthesis of Compound 24-1 of Example 4, except that Compound 35 of Example 16 was used instead of Compound 6.

Synthesis of Compound RD-19

About 30 g of Compound RD-19 was obtained by the same method as the synthesis of Compound RD-04 of Example 4, except that Compound 41-1 was used instead of Compound 24-1.

The NMR spectrum of the obtained Compound RD-19 is as follows.

$^1$H NMR (CDCl$_3$, standard material TMS) δ(ppm): 8.04 (2H, d), 7.56 (4H, d), 7.55 (4H, d), 7.51 (4H, d), 7.47 (2H, d), 7.40 (2H, d), 7.21 (2H, d), 6.27 (2H, dd), 6.05 (2H, dd), 5.59 (2H, dd), 4.13 (4H, t), 4.05 (1H, s), 3.97 (4H, t), 2.50 (1H, t), 1.60-1.12 (23H, m)

Example 20: Synthesis of Compound RD-20

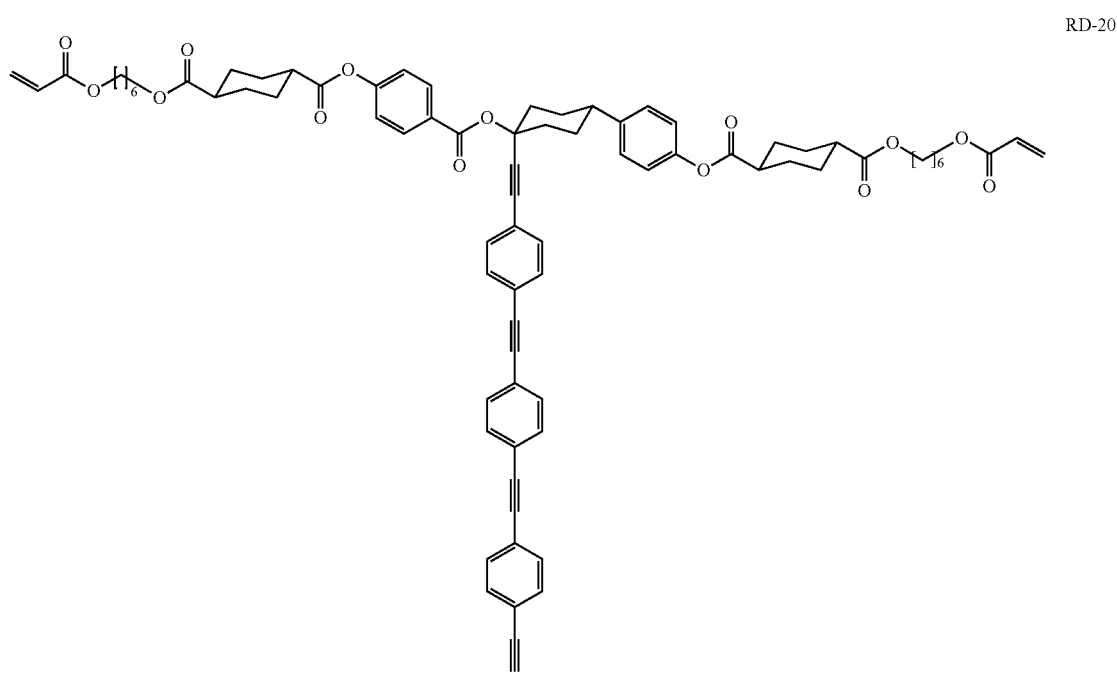

RD-20

Compound RD-20 was synthesized according to the scheme shown in FIGS. 5a and 5b.

Synthesis of Compound 41-2

About 70 g of Compound 41-2 was obtained by the same method as the synthesis of Compound 24-1 of Example 4, except that Compound 23-2 of Example 5 was used instead of Compound 23-1 and Compound 35 of Example 16 was used instead of Compound 6.

Synthesis of Compound RD-20

About 50 g of Compound RD-20 was obtained by the same method as the synthesis of Compound RD-04 of Example 4, except that Compound 41-2 was used instead of Compound 24-1.

The NMR spectrum of the obtained Compound RD-20 is as follows.

$^1$H NMR (CDCl$_3$, standard material TMS) δ(ppm): 8.04 (2H, d), 7.56 (4H, d), 7.55 (4H, d), 7.51 (4H, d), 7.47 (2H, d), 7.40 (2H, d), 7.21 (2H, d), 6.27 (2H, dd), 6.05 (2H, dd), 5.59 (2H, dd), 4.13 (4H, t), 4.05 (1H, s), 3.97 (4H, t), 2.50 (1H, t), 1.60-1.12 (31H, m)

Example 21: Synthesis of Compound RD-21

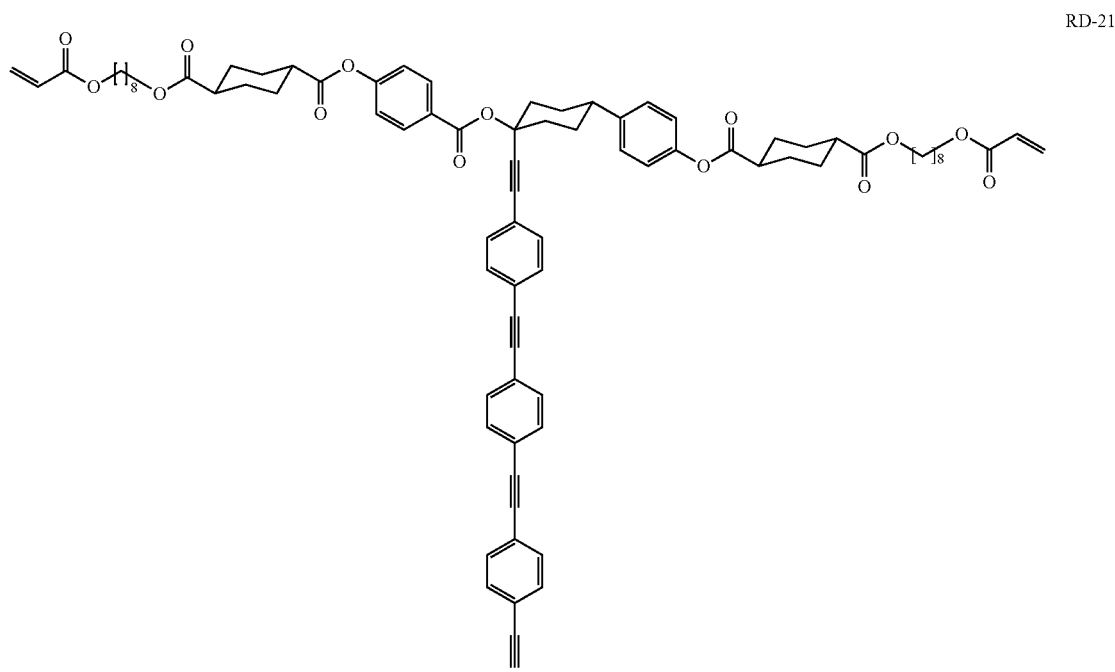

Compound RD-21 was synthesized according to the scheme shown in FIGS. 5a and 5b.

Synthesis of Compound 41-3

About 70 g of Compound 41-3 was obtained by the same method as the synthesis of Compound 24-1 of Example 4, except that Compound 23-3 of Example 6 was used instead of Compound 23-1 and Compound 35 of Example 16 was used instead of Compound 6.

Synthesis of Compound RD-21

About 50 g of Compound RD-21 was obtained by the same method as the synthesis of Compound RD-04 of Example 4, except that Compound 41-3 was used instead of Compound 24-1.

The NMR spectrum of the obtained Compound RD-21 is as follows.

$^1$H NMR (CDCl$_3$, standard material TMS) δ(ppm): 8.04 (2H, d), 7.56 (4H, d), 7.55 (4H, d), 7.51 (4H, d), 7.47 (2H, d), 7.40 (2H, d), 7.21 (2H, d), 6.27 (2H, dd), 6.05 (2H, dd), 5.59 (2H, dd), 4.13 (4H, t), 4.05 (1H, s), 3.97 (4H, t), 2.50 (1H, t), 1.60-1.12 (39H, m)

Example 22: Synthesis of Compound RD-22

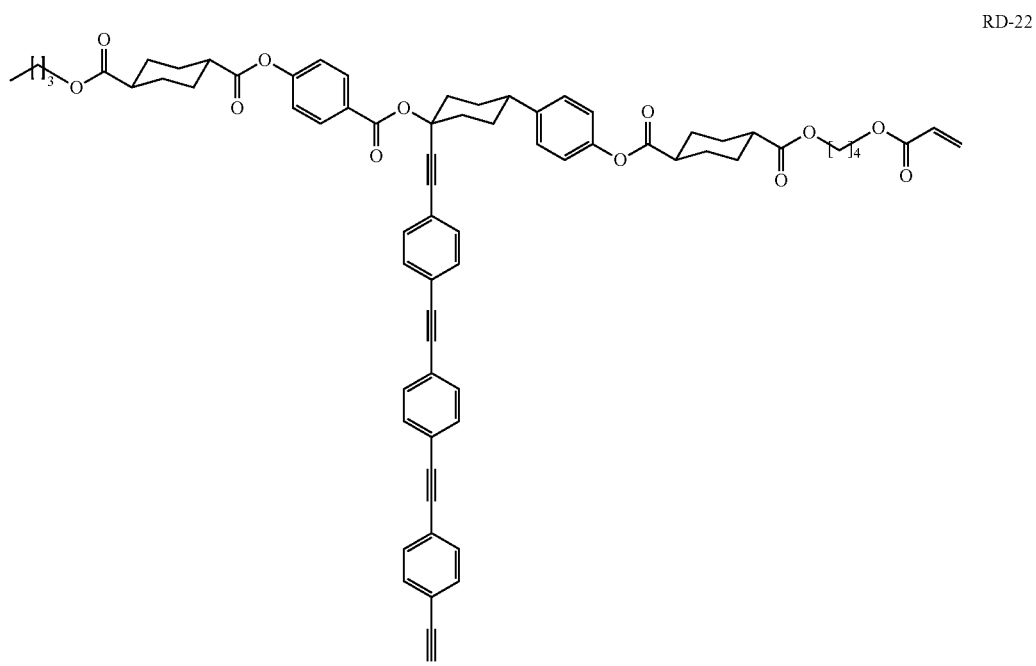

RD-22

Figure 6A:
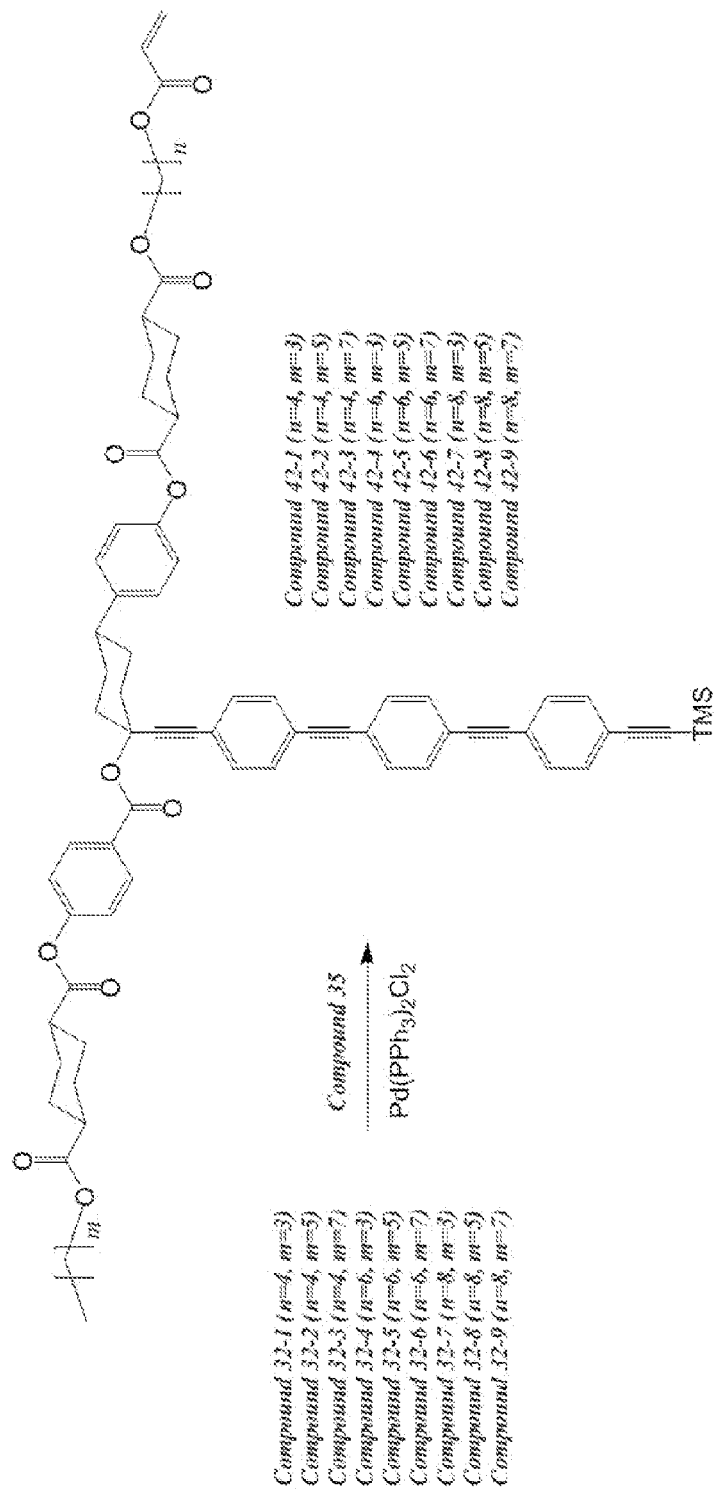
Figure 6B:
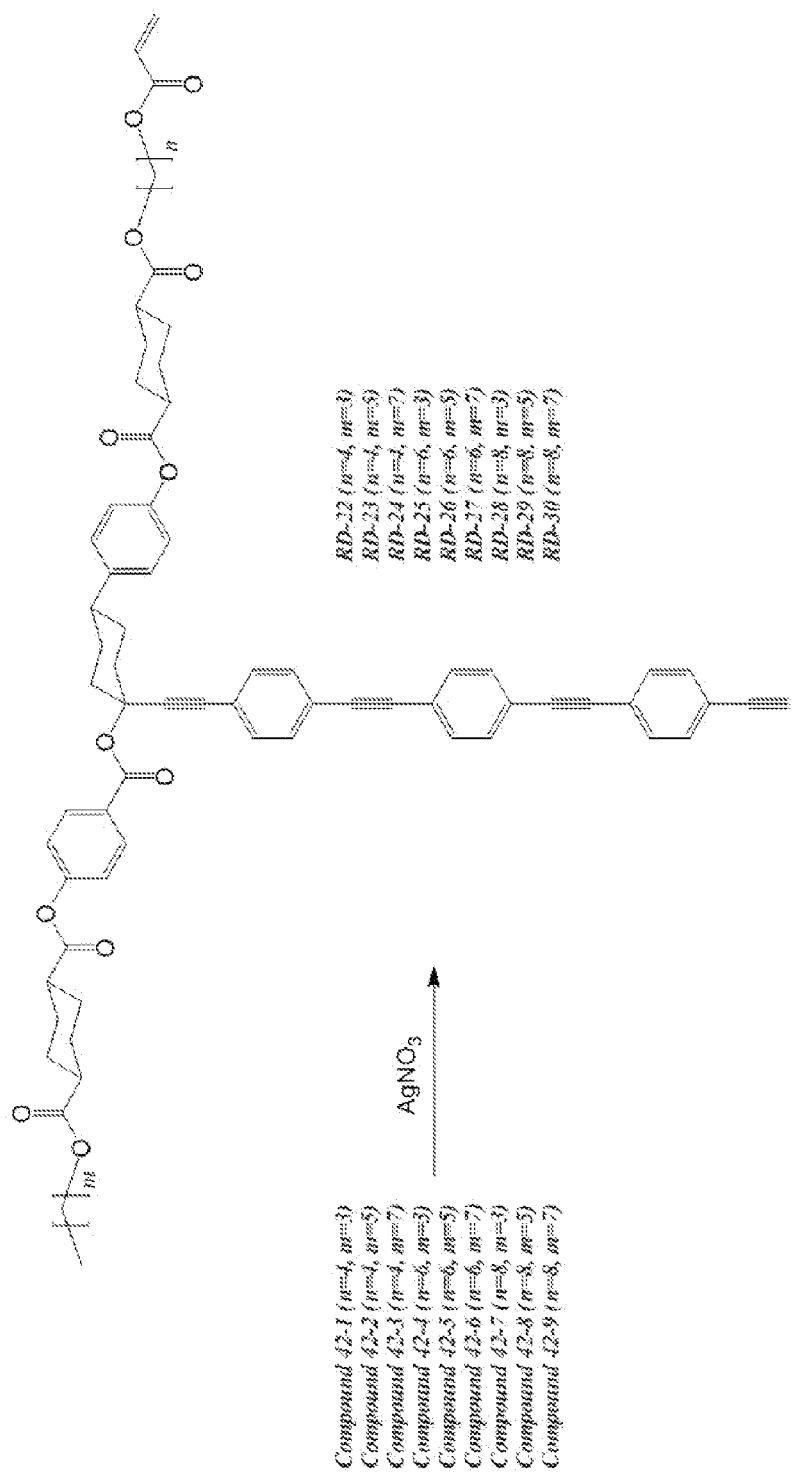

Compound RD-22 was synthesized according to the scheme shown in FIGS. 6a and 6b.

Synthesis of Compound 42-1

About 70 g of Compound 42-1 was obtained by the same method as the synthesis of Compound 15-1 of Example 1, except that Compound 32-1 (n=4, m=3) of Example 7 was used instead of Compound 14-1 and Compound 35 of Example 16 was used instead of Compound 6.

Synthesis of Compound RD-22

About 30 g of Compound RD-22 was obtained by the same method as the synthesis of Compound RD-01 of Example 1, except that Compound 42-1 was used instead of Compound 15-1.

The NMR spectrum of the obtained Compound RD-22 is as follows.

$^1$H NMR (CDCl$_3$, standard material TMS) δ(ppm): 8.04 (2H, d), 7.56 (4H, d), 7.55 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (25H, m)

Example 23: Synthesis of Compound RD-23

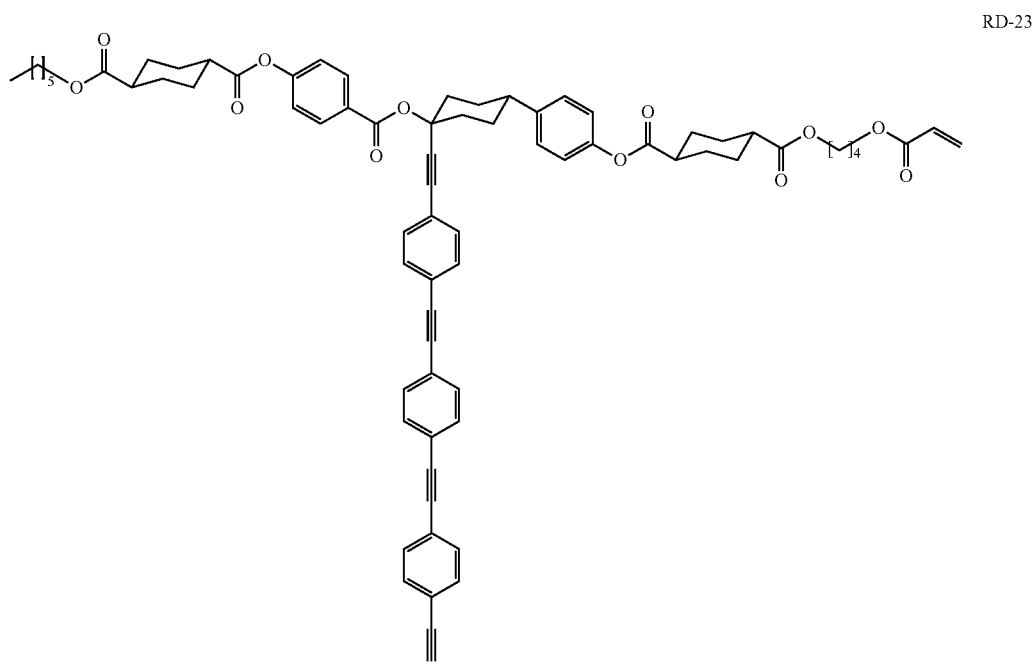

Compound RD-23 was synthesized according to the scheme shown in FIGS. 6a and 6b.

Synthesis of Compound 42-2

About 60 g of Compound 42-2 was obtained by the same method as the synthesis of Compound 15-1 of Example 1, except that Compound 32-2 (n=4, m=5) of Example 8 was used instead of Compound 14-1 and Compound 35 of Example 16 was used instead of Compound 6.

Synthesis of Compound RD-23

About 50 g of Compound RD-23 was obtained by the same method as the synthesis of Compound RD-01 of Example 1, except that Compound 42-2 was used instead of Compound 15-1.

The NMR spectrum of the obtained Compound RD-23 is as follows.

$^1$H NMR (CDCl$_3$, standard material TMS) δ(ppm): 8.04 (2H, d), 7.56 (4H, d), 7.55 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (29H, m)

Example 24: Synthesis of Compound RD-24

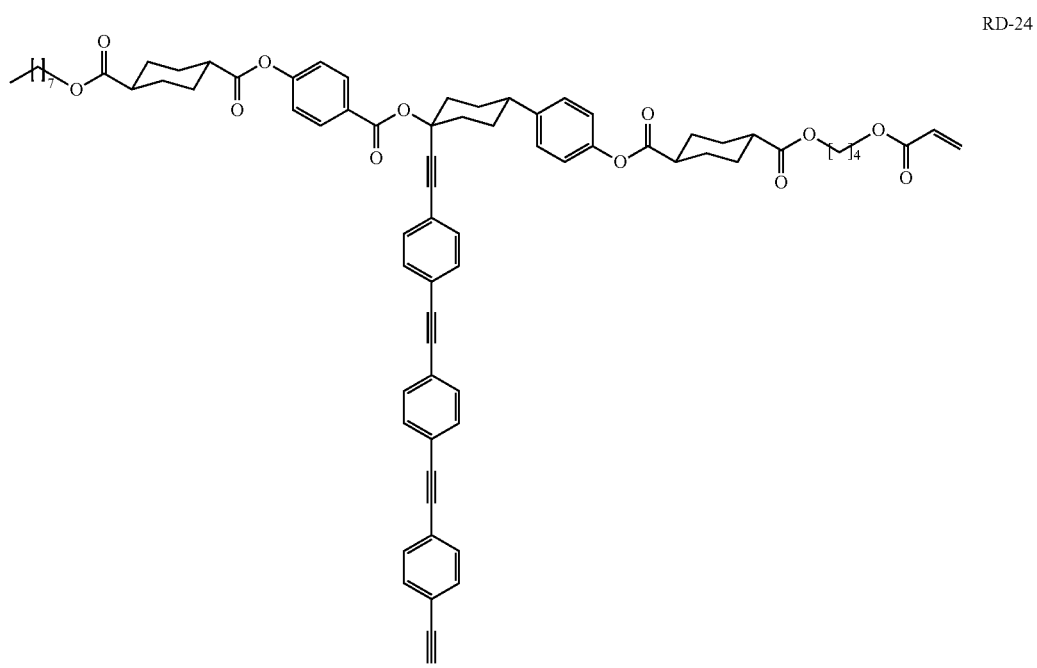

Compound RD-24 was synthesized according to the scheme shown in FIGS. 6a and 6b.

Synthesis of Compound 42-3

About 60 g of Compound 42-3 was obtained by the same method as the synthesis of Compound 15-1 of Example 1, except that Compound 32-3 (n=4, m=7) of Example 9 was used instead of Compound 14-1 and Compound 35 of Example 16 was used instead of Compound 6.

Synthesis of Compound RD-24

About 50 g of Compound RD-24 was obtained by the same method as the synthesis of Compound RD-01 of Example 1, except that Compound 42-3 was used instead of Compound 15-1.

The NMR spectrum of the obtained Compound RD-24 is as follows.

$^1$H NMR (CDCl$_3$, standard material TMS) δ(ppm): 8.04 (2H, d), 7.56 (4H, d), 7.55 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (33H, m)

Example 25: Synthesis of Compound RD-25

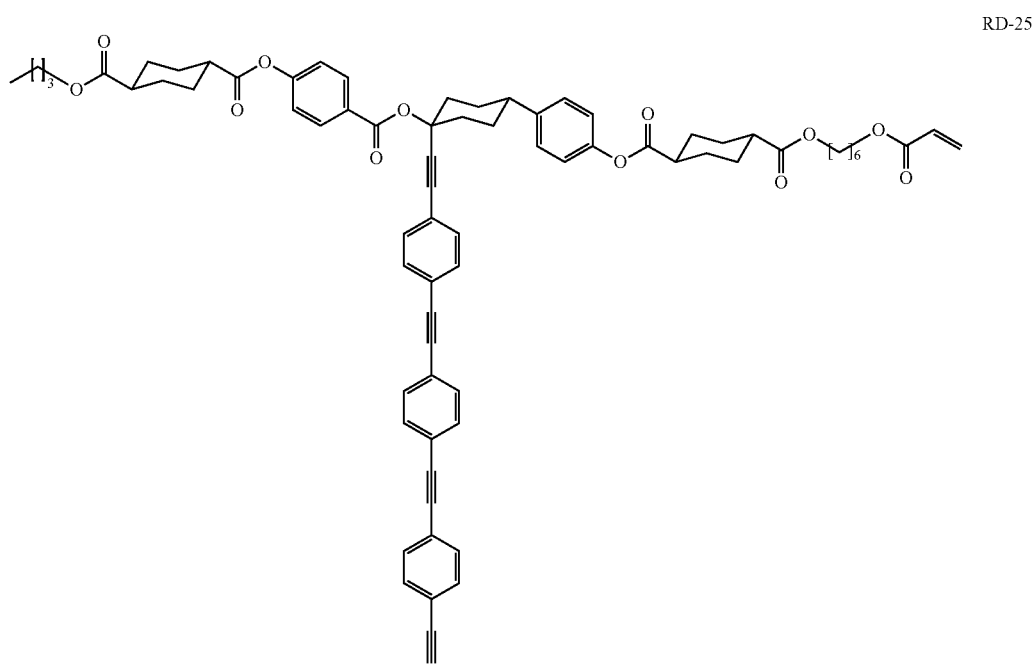

RD-25

Compound RD-25 was synthesized according to the scheme shown in FIGS. 6a and 6b.

Synthesis of Compound 42-4

About 60 g of Compound 42-4 was obtained by the same method as the synthesis of Compound 15-1 of Example 1, except that Compound 32-4 (n=6, m=3) of Example 10 was used instead of Compound 14-1 and Compound 35 of Example 16 was used instead of Compound 6.

Synthesis of Compound RD-25

About 50 g of Compound RD-25 was obtained by the same method as the synthesis of Compound RD-01 of Example 1, except that Compound 42-4 was used instead of Compound 15-1.

The NMR spectrum of the obtained Compound RD-25 is as follows.

$^1$H NMR (CDCl$_3$, standard material TMS) δ(ppm): 8.04 (2H, d), 7.56 (4H, d), 7.55 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (29H, m)

Example 26: Synthesis of Compound RD-26

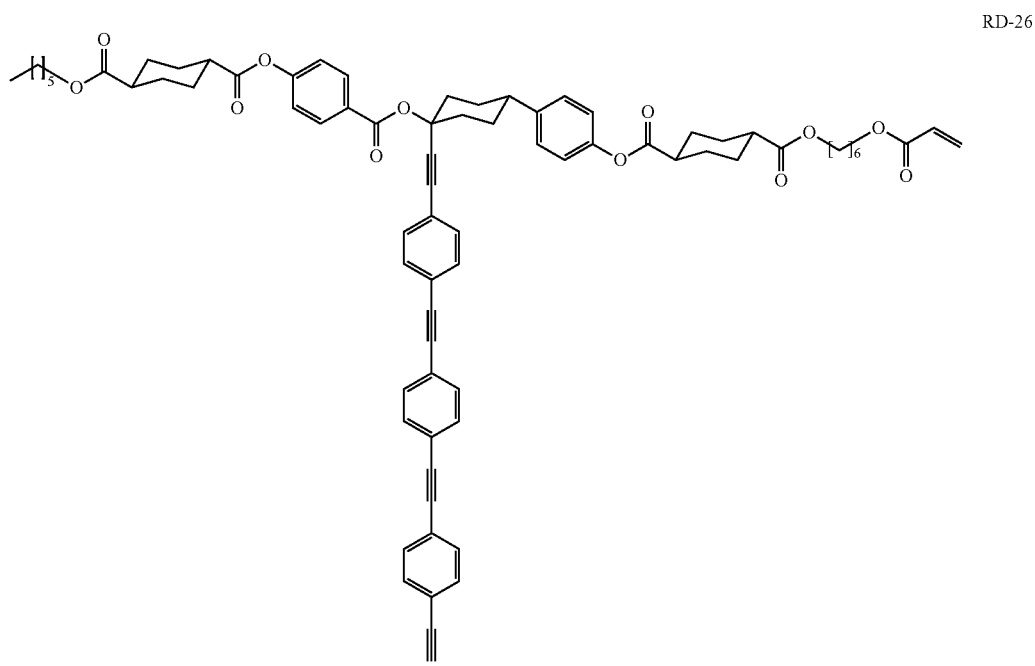

Compound RD-26 was synthesized according to the scheme shown in FIGS. 6a and 6b.

Synthesis of Compound 42-5

About 60 g of Compound 42-5 was obtained by the same method as the synthesis of Compound 15-1 of Example 1, except that Compound 32-5 (n=6, m=5) of Example 11 was used instead of Compound 14-1 and Compound 35 of Example 16 was used instead of Compound 6.

Synthesis of Compound RD-26

About 50 g of Compound RD-26 was obtained by the same method as the synthesis of Compound RD-01 of Example 1, except that Compound 42-5 was used instead of Compound 15-1.

The NMR spectrum of the obtained Compound RD-26 is as follows.

$^1$H NMR (CDCl$_3$, standard material TMS) δ(ppm): 8.04 (2H, d), 7.56 (4H, d), 7.55 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (33H, m)

Example 27: Synthesis of Compound RD-27

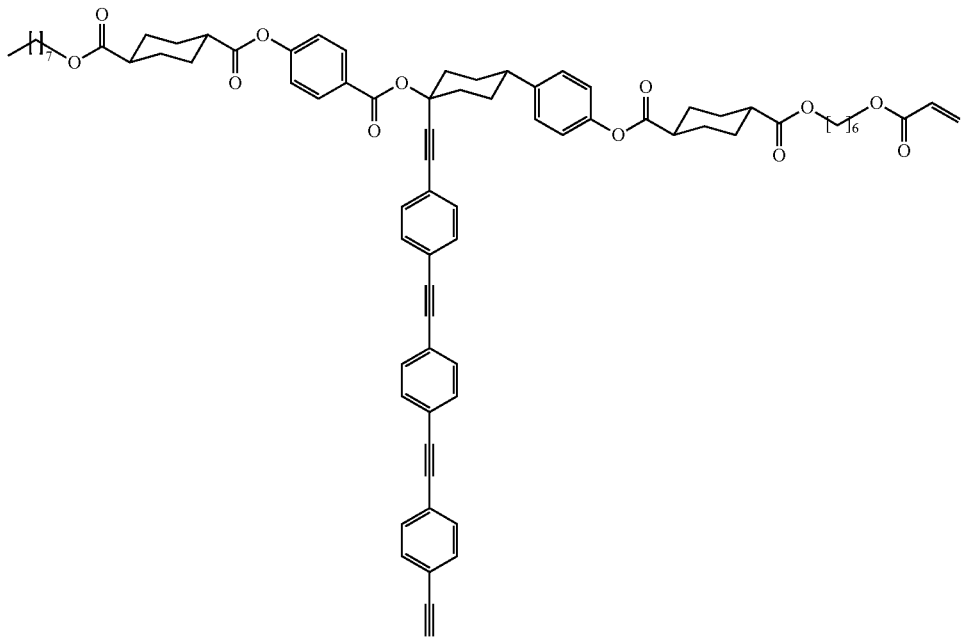

Compound RD-27 was synthesized according to the scheme shown in FIGS. 6a and 6b.

Synthesis of Compound 42-6

About 60 g of Compound 42-6 was obtained by the same method as the synthesis of Compound 15-1 of Example 1, except that Compound 32-6 (n=6, m=7) of Example 12 was used instead of Compound 14-1 and Compound 35 of Example 16 was used instead of Compound 6.

Synthesis of Compound RD-27

About 50 g of Compound RD-27 was obtained by the same method as the synthesis of Compound RD-01 of Example 1, except that Compound 42-6 was used instead of Compound 15-1.

The NMR spectrum of the obtained Compound RD-27 is as follows.

$^1$H NMR (CDCl$_3$, standard material TMS) δ(ppm): 8.04 (2H, d), 7.56 (4H, d), 7.55 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (37H, m)

Example 28: Synthesis of Compound RD-28

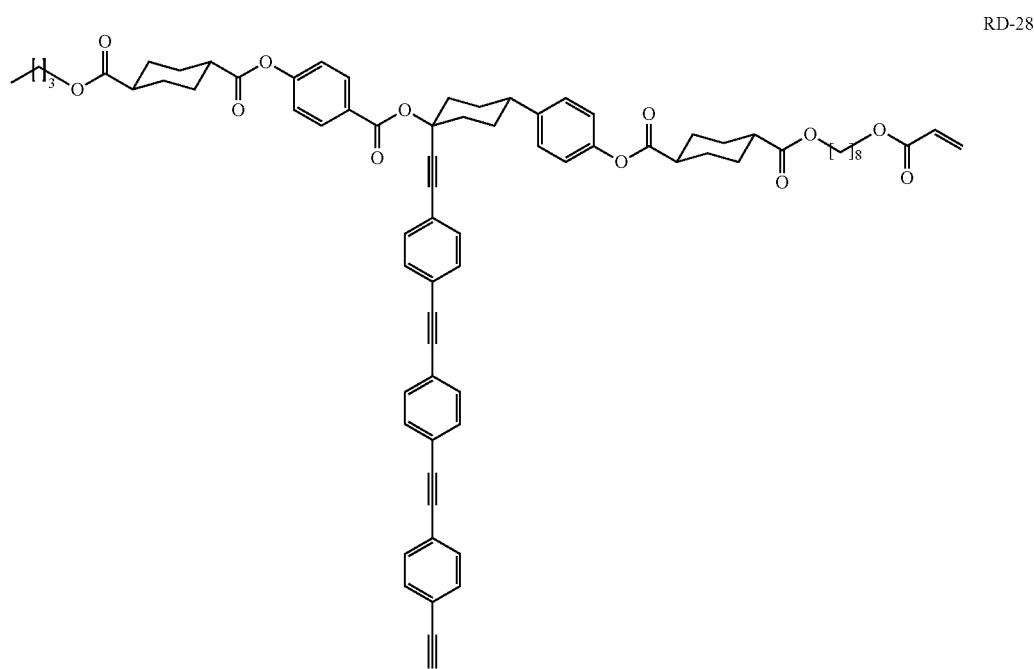

Compound RD-28 was synthesized according to the scheme shown in FIGS. 6a and 6b.

Synthesis of Compound 42-7

About 60 g of Compound 42-7 was obtained by the same method as the synthesis of Compound 15-1 of Example 1, except that Compound 32-7 (n=8, m=3) of Example 13 was used instead of Compound 14-1 and Compound 35 of Example 16 was used instead of Compound 6.

Synthesis of Compound RD-28

About 50 g of Compound RD-28 was obtained by the same method as the synthesis of Compound RD-01 of Example 1, except that Compound 42-7 was used instead of Compound 15-1.

The NMR spectrum of the obtained Compound RD-28 is as follows.

$^1$H NMR (CDCl$_3$, standard material TMS) δ(ppm): 8.04 (2H, d), 7.56 (4H, d), 7.55 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (33H, m)

Example 29: Synthesis of Compound RD-29

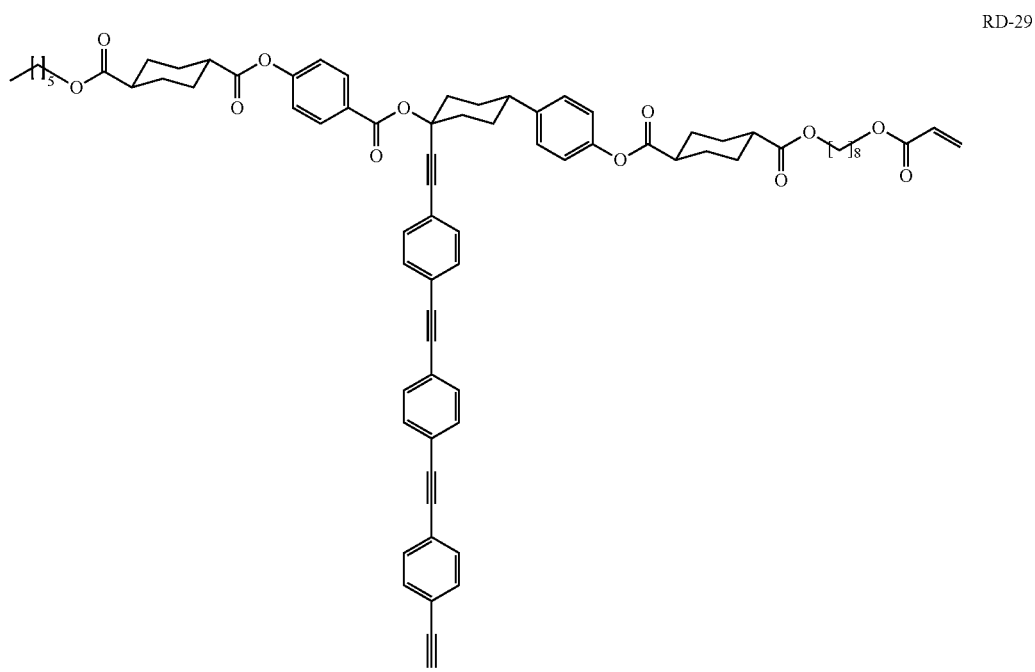

Compound RD-29 was synthesized according to the scheme shown in FIGS. 6a and 6b.

Synthesis of Compound 42-8

About 60 g of Compound 42-8 was obtained by the same method as the synthesis of Compound 15-1 of Example 1, except that Compound 32-8 (n=8, m=5) of Example 14 was used instead of Compound 14-1 and Compound 35 of Example 16 was used instead of Compound 6.

Synthesis of Compound RD-29

About 50 g of Compound RD-29 was obtained by the same method as the synthesis of Compound RD-01 of Example 1, except that Compound 42-8 was used instead of Compound 15-1.

The NMR spectrum of the obtained Compound RD-29 is as follows.

$^1$H NMR (CDCl$_3$, standard material TMS) δ(ppm): 8.04 (2H, d), 7.56 (4H, d), 7.55 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (37H, m)

Example 30: Synthesis of Compound RD-30

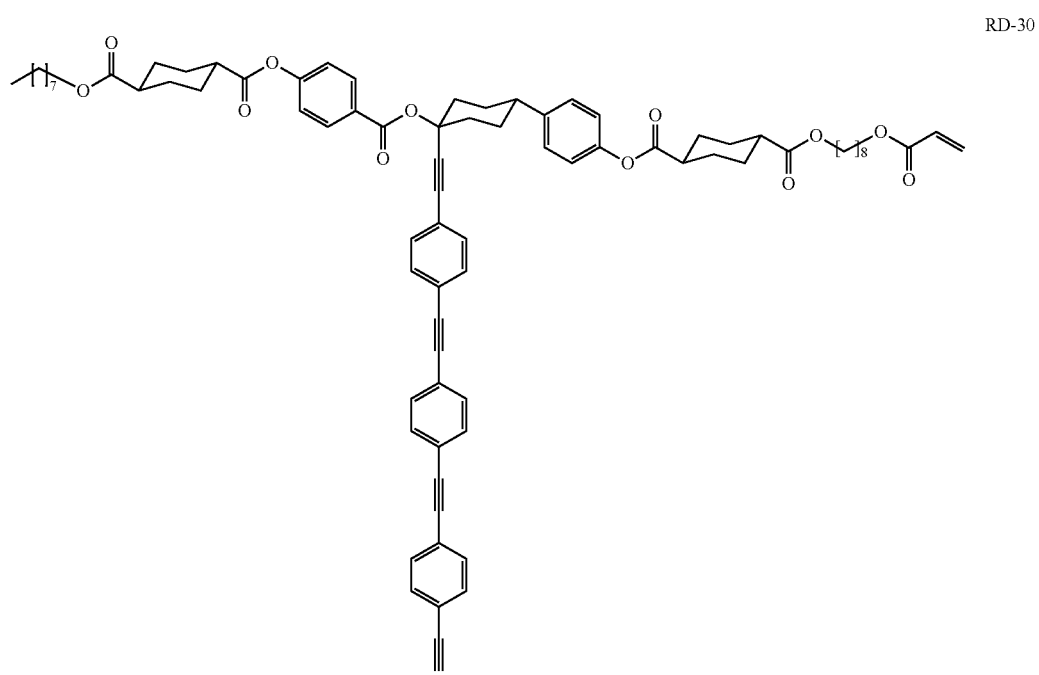

Compound RD-30 was synthesized according to the scheme shown in FIGS. 6a and 6b.

Synthesis of Compound 42-9

About 60 g of Compound 42-9 was obtained by the same method as the synthesis of Compound 15-1 of Example 1, except that Compound 32-9 (n=8, m=7) of Example 15 was used instead of Compound 14-1 and Compound 35 of Example 16 was used instead of Compound 6.

Synthesis of Compound RD-30

About 50 g of Compound RD-30 was obtained by the same method as the synthesis of Compound RD-01 of Example 1, except that Compound 42-9 was used instead of Compound 15-1.

The NMR spectrum of the obtained Compound RD-30 is as follows.

$^1$H NMR (CDCl$_3$, standard material TMS) δ(ppm): 8.04 (2H, d), 7.56 (4H, d), 7.55 (4H, d), 7.51 (4H, d), 7.47 (2H, d), 7.40 (2H, d), 7.21 (2H, d), 6.27 (1H, dd), 6.05 (1H, dd), 5.59 (1H, dd), 4.13 (4H, t), 4.05 (1H, s), 3.97 (2H, t), 2.50 (1H, t), 1.60-0.90 (41H, m)

Example 31: Synthesis of Compound RD-31

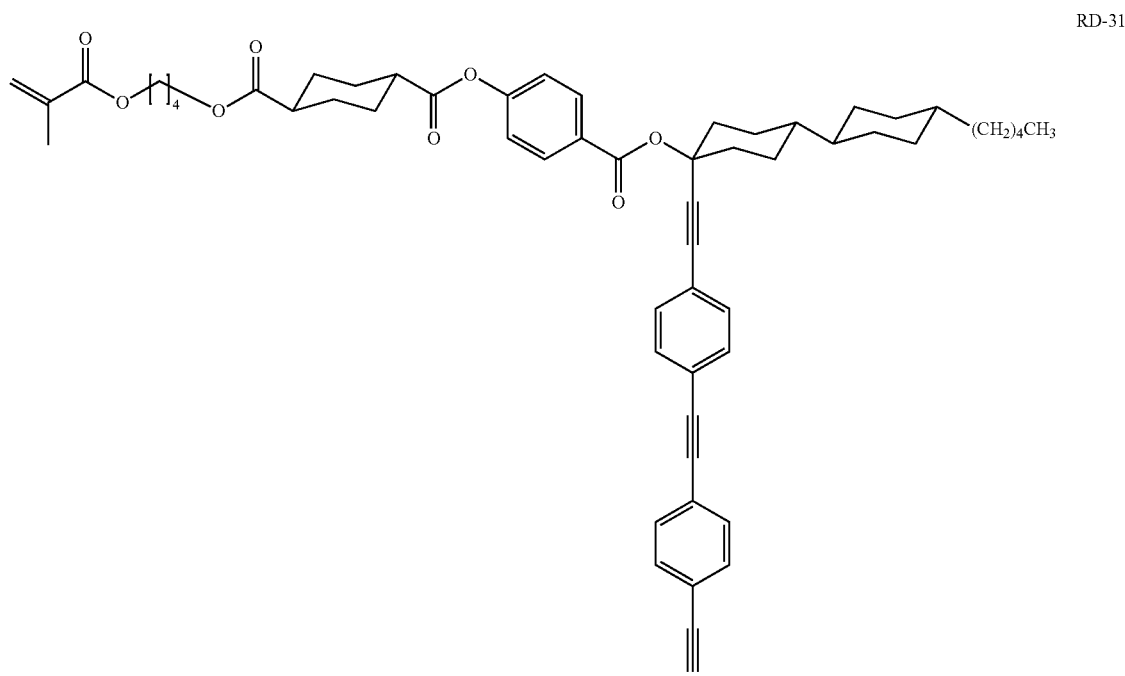

Figure 7A:
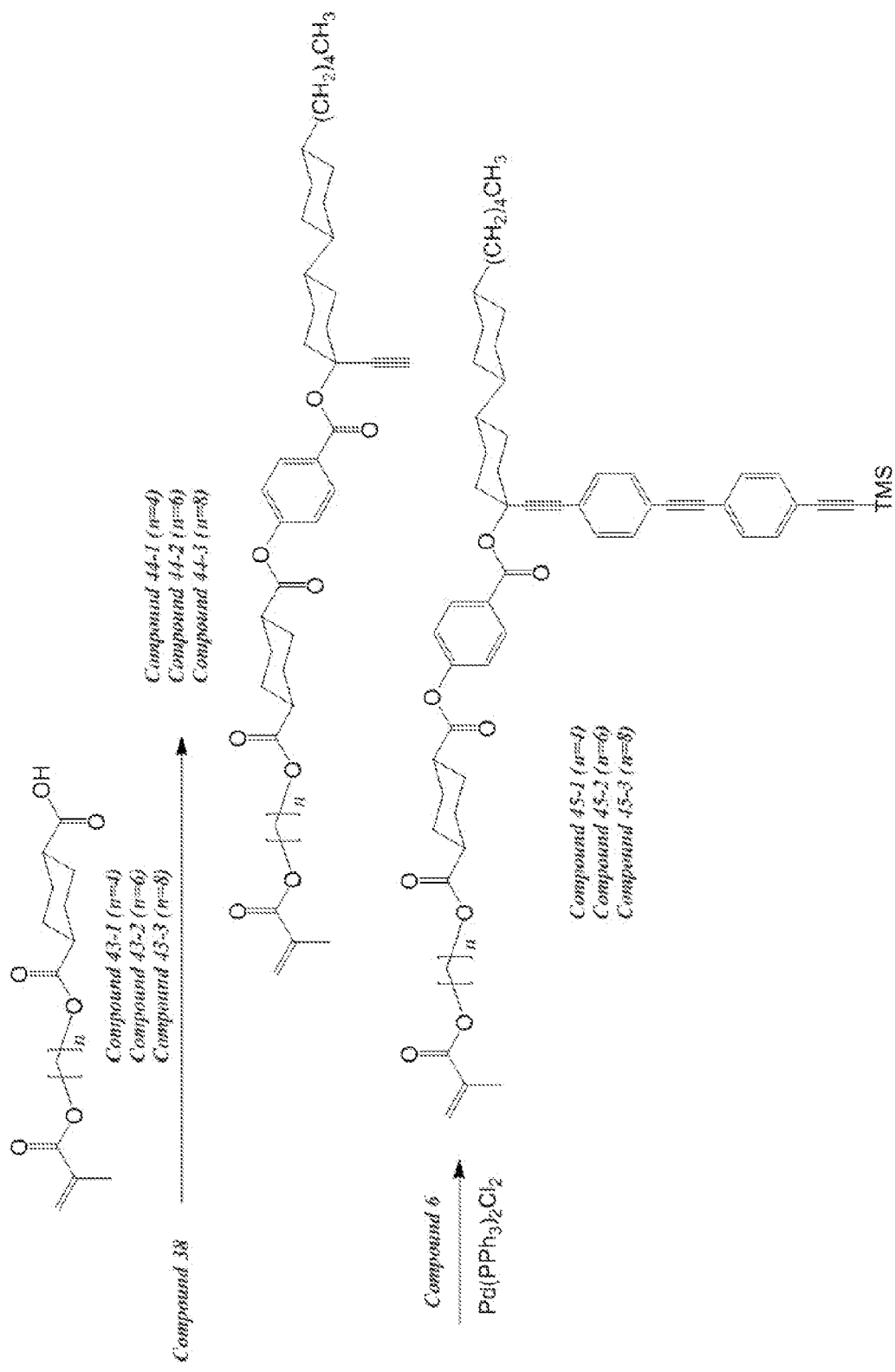
Figure 7B:
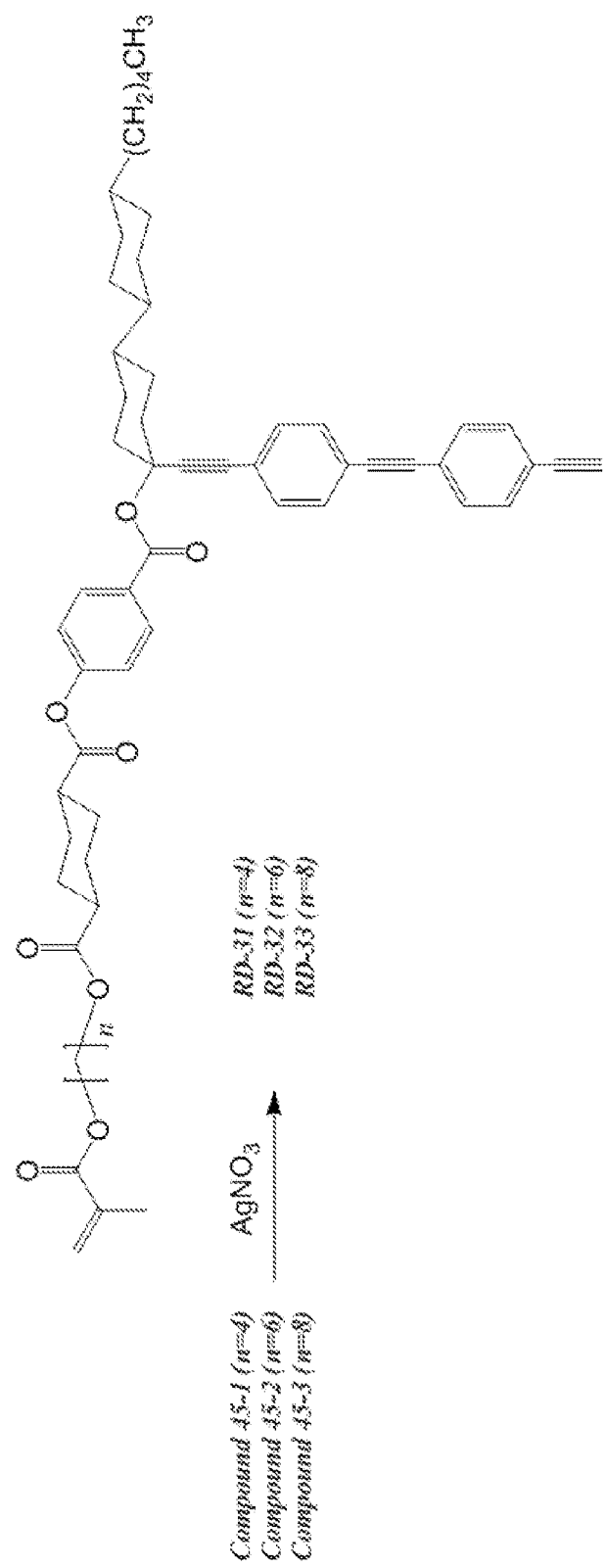

Compound RD-31 was synthesized according to the scheme shown in FIGS. 7a and 7b.

Synthesis of Compound 44-1

About 100 g of Compound 44-1 was obtained by the same method as the synthesis of Compound 12-1 of Example 1, except that Compound 38 of Example 16 was used instead of Compound 10 and Compound 43-1 [(1r,4r)-4-((4-(methacryloyloxy)butoxy)carbonyl)cyclohexanecarboxylic acid] was used instead of Compound 11-1.

Synthesis of Compound 45-1

About 30 g of Compound 45-1 was obtained by the same method as the synthesis of Compound 15-1 of Example 1, except that Compound 44-1 was used instead of Compound 14-1.

Synthesis of Compound RD-31

About 20 g of Compound RD-31 was obtained by the same method as the synthesis of Compound RD-01 of Example 1, except that Compound 45-1 was used instead of Compound 15-1.

The NMR spectrum of the obtained Compound RD-31 is as follows.

$^1$H NMR (CDCl$_3$, standard material TMS) δ(ppm): 8.04 (2H, d), 7.56 (4H, d), 7.51 (4H, d), 7.40 (2H, d), 6.48 (1H, d), 6.40 (1H, d), 5.59 (1H, d), 4.13 (2H, t), 4.05 (1H, s), 3.97 (2H, t), 3.52 (1H, s), 2.01 (3H, s), 1.60-1.12 (48H, m)

Example 32: Synthesis of Compound RD-32

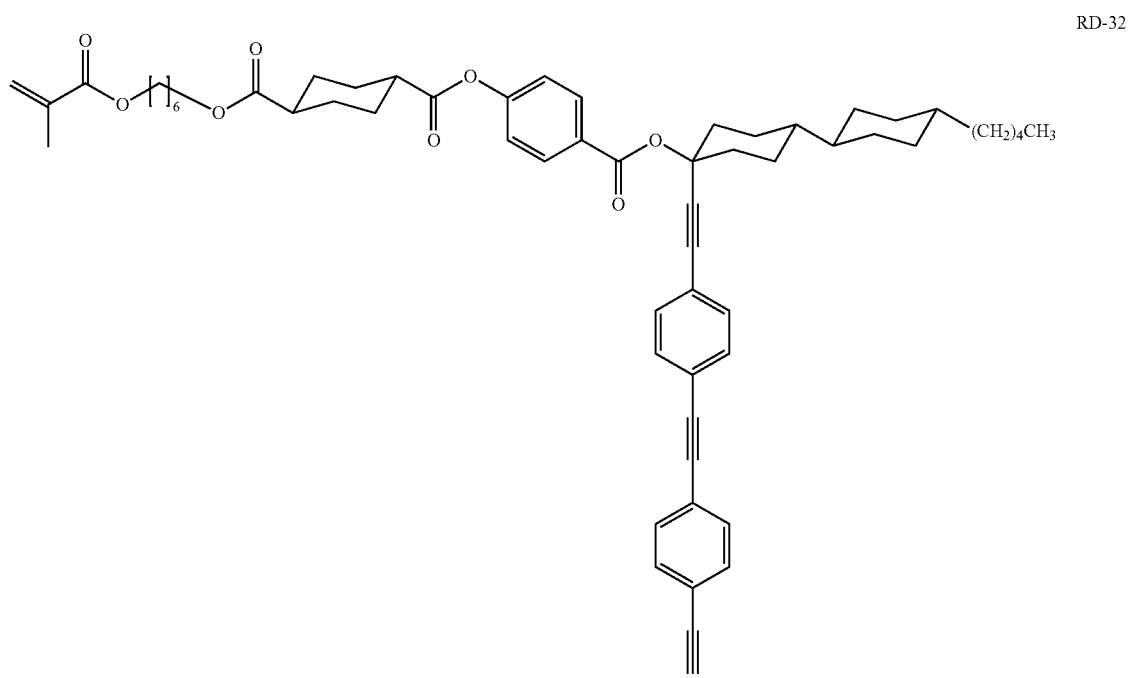

Compound RD-32 was synthesized according to the scheme shown in FIGS. 7a and 7b.

Synthesis of Compound 44-2

About 100 g of Compound 44-2 was obtained by the same method as the synthesis of Compound 12-1 of Example 1, except that Compound 38 of Example 16 was used instead of Compound 10 and Compound 43-2 [(1r,4r)-4-(((6-(methacryloyloxy)hexyl)oxy)carbonyl)cyclohexanecarboxylic acid] was used instead of Compound 11-1.

Synthesis of Compound 45-2

About 70 g of Compound 45-2 was obtained by the same method as the synthesis of Compound 15-1 of Example 1, except that Compound 44-2 was used instead of Compound 14-1.

Synthesis of Compound RD-32

About 50 g of Compound RD-32 was obtained by the same method as the synthesis of Compound RD-01 of Example 1, except that Compound 45-2 was used instead of Compound 15-1.

The NMR spectrum of the obtained Compound RD-32 is as follows.

$^1$H NMR (CDCl$_3$, standard material TMS) δ(ppm): 8.04 (2H, d), 7.56 (4H, d), 7.51 (4H, d), 7.40 (2H, d), 6.48 (1H, d), 6.40 (1H, d), 5.59 (1H, d), 4.13 (2H, t), 4.05 (1H, s), 3.97 (2H, t), 3.52 (1H, s), 2.01 (3H, s), 1.60-1.12 (52H, m)

Example 33: Synthesis of Compound RD-33

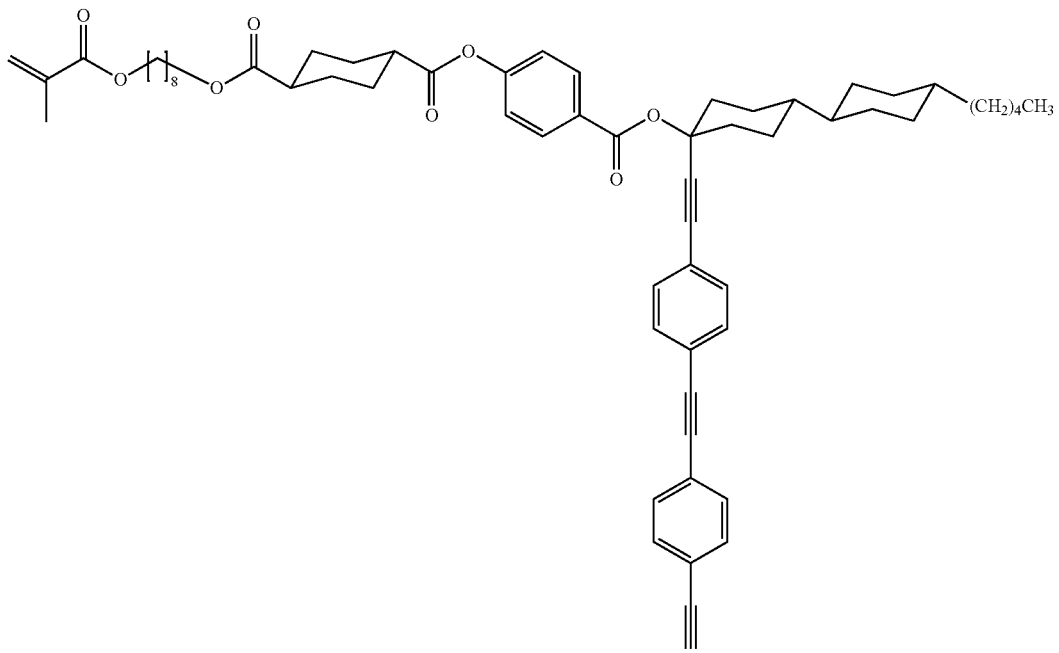

Compound RD-33 was synthesized according to the scheme shown in FIGS. 7a and 7b.

Synthesis of Compound 44-3

About 100 g of Compound 44-3 was obtained by the same method as the synthesis of Compound 12-1 of Example 1, except that Compound 38 of Example 16 was used instead of Compound 10 and Compound 43-3 [(1r,4r)-4-(((8-(methacryloyloxy)octyl)oxy)carbonyl)cyclohexanecarboxylic acid] was used instead of Compound 11-1.

Synthesis of Compound 45-3

About 70 g of Compound 45-3 was obtained by the same method as the synthesis of Compound 15-1 of Example 1, except that Compound 44-3 was used instead of Compound 14-1.

Synthesis of Compound RD-33

About 50 g of Compound RD-33 was obtained by the same method as the synthesis of Compound RD-01 of Example 1, except that Compound 45-3 was used instead of Compound 15-1.

The NMR spectrum of the obtained Compound RD-33 is as follows.

$^1$H NMR (CDCl$_3$, standard material TMS) δ(ppm): 8.04 (2H, d), 7.56 (4H, d), 7.51 (4H, d), 7.40 (2H, d), 6.48 (1H, d), 6.40 (1H, d), 5.59 (1H, d), 4.13 (2H, t), 4.05 (1H, s), 3.97 (2H, t), 3.52 (1H, s), 2.01 (3H, s), 1.60-1.12 (56H, m)

Example 34: Synthesis of Compound RD-34

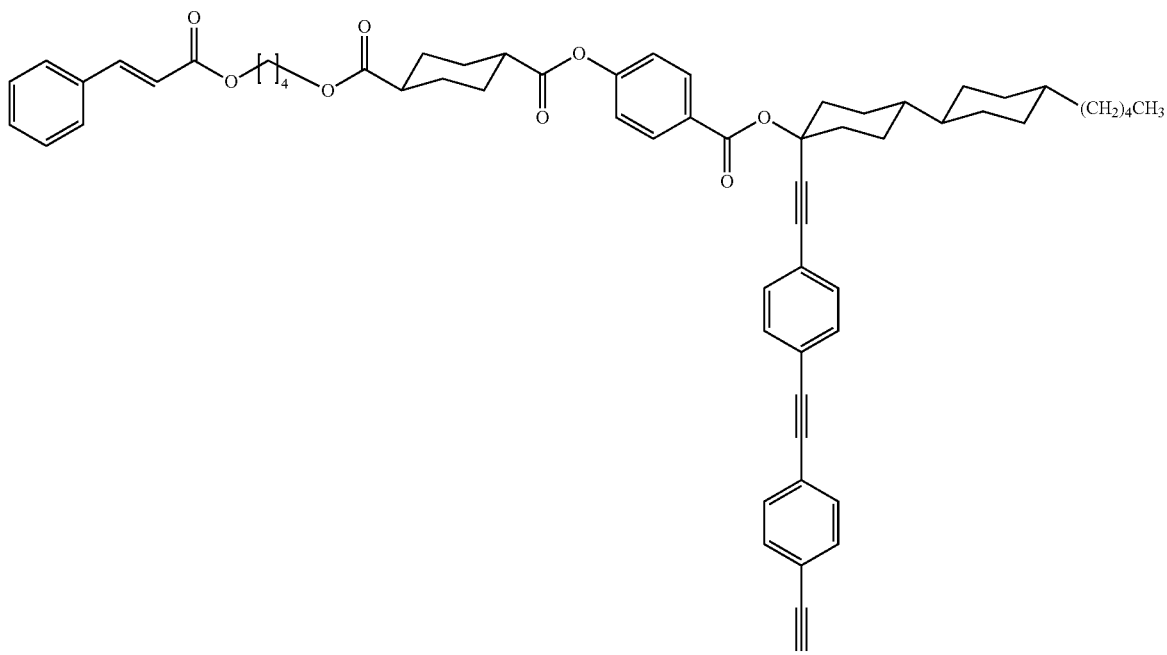

RD-34

Figure 8A:
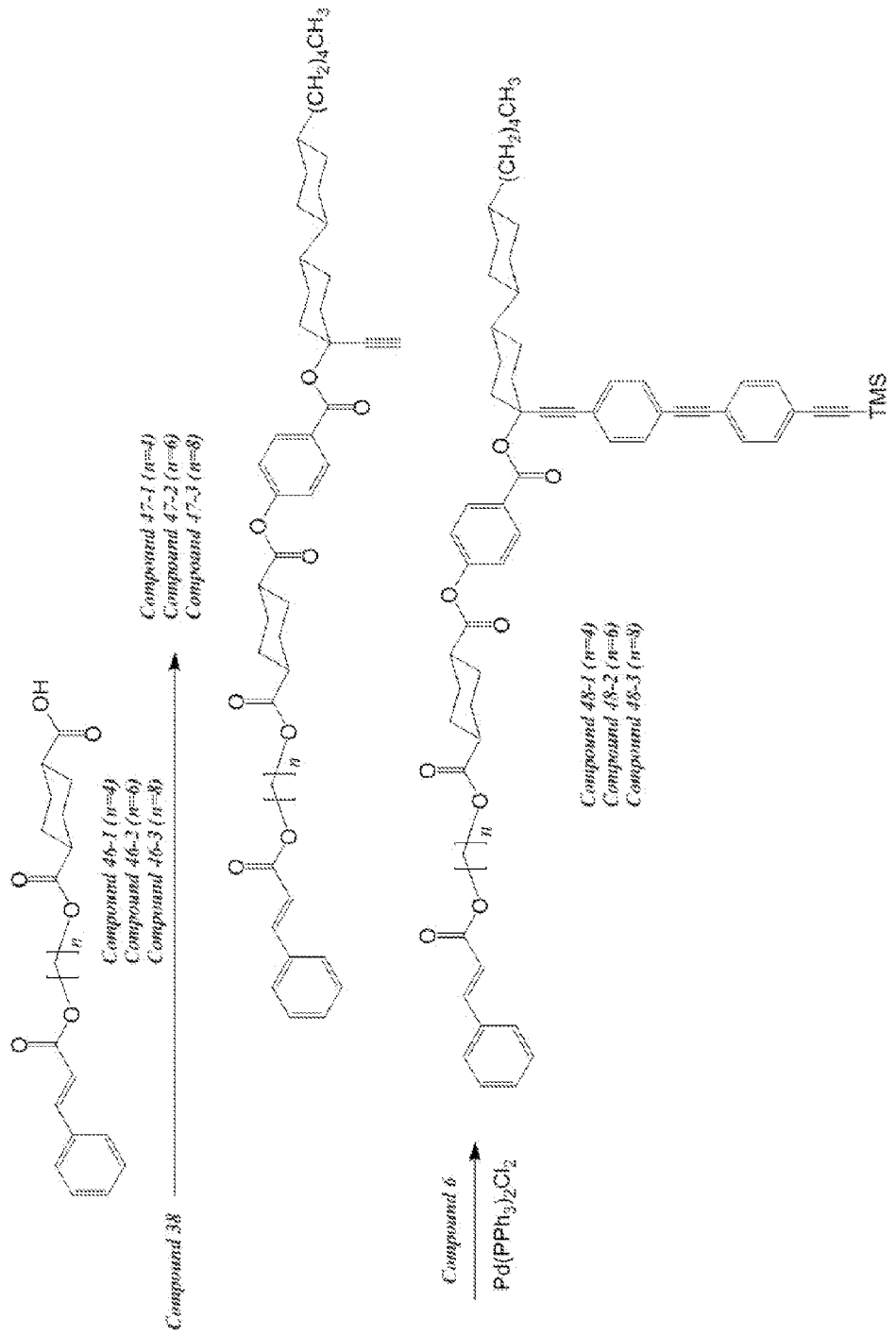
Figure 8B:
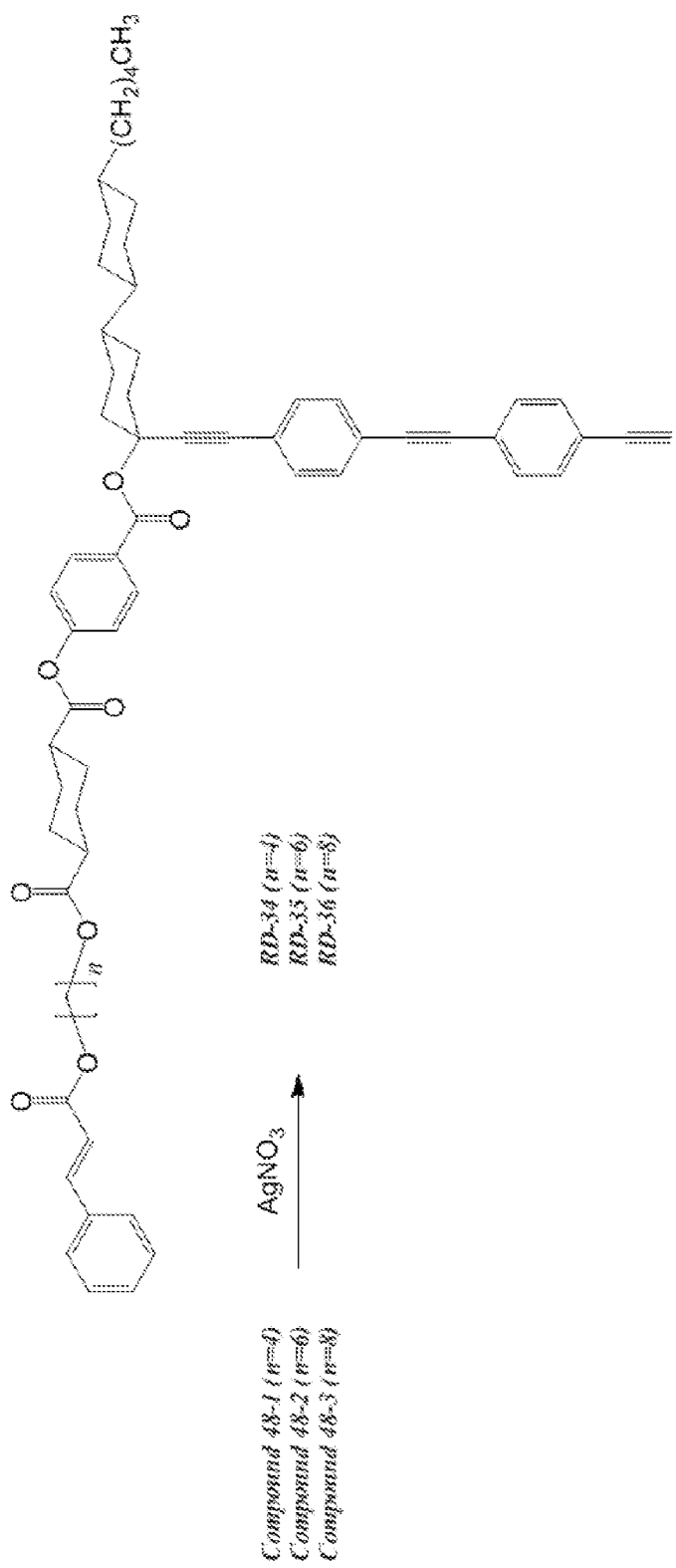

Compound RD-34 was synthesized according to the scheme shown in FIGS. 8a and 8b.

Synthesis of Compound 47-1

About 100 g of Compound 47-1 was obtained by the same method as the synthesis of Compound 12-1 of Example 1, except that Compound 38 of Example 16 was used instead of Compound 10 and Compound 46-1 [(1r,4r)-4-((4-(cinnamoyloxy)butoxy)carbonyl)cyclohexanecarboxylic acid] was used instead of Compound 11-1.

Synthesis of Compound 48-1

About 30 g of Compound 48-1 was obtained by the same method as the synthesis of Compound 15-1 of Example 1, except that Compound 47-1 was used instead of Compound 14-1.

Synthesis of Compound RD-34

About 20 g of Compound RD-34 was obtained by the same method as the synthesis of Compound RD-01 of Example 1, except that Compound 48-1 was used instead of Compound 15-1.

The NMR spectrum of the obtained Compound RD-34 is as follows.

$^1$H NMR (CDCl$_3$, standard material TMS) δ(ppm): 8.04 (2H, d), 7.60 (2H, d), 7.56 (4H, d), 7.51 (4H, d), 7.48 (1H, d), 7.40 (4H, d), 7.33 (1H, t), 6.31 (1H, d), 4.13 (2H, t), 4.05 (1H, s), 3.97 (2H, t), 3.52 (1H, s), 1.60-1.12 (48H, m)

Example 35: Synthesis of Compound RD-35

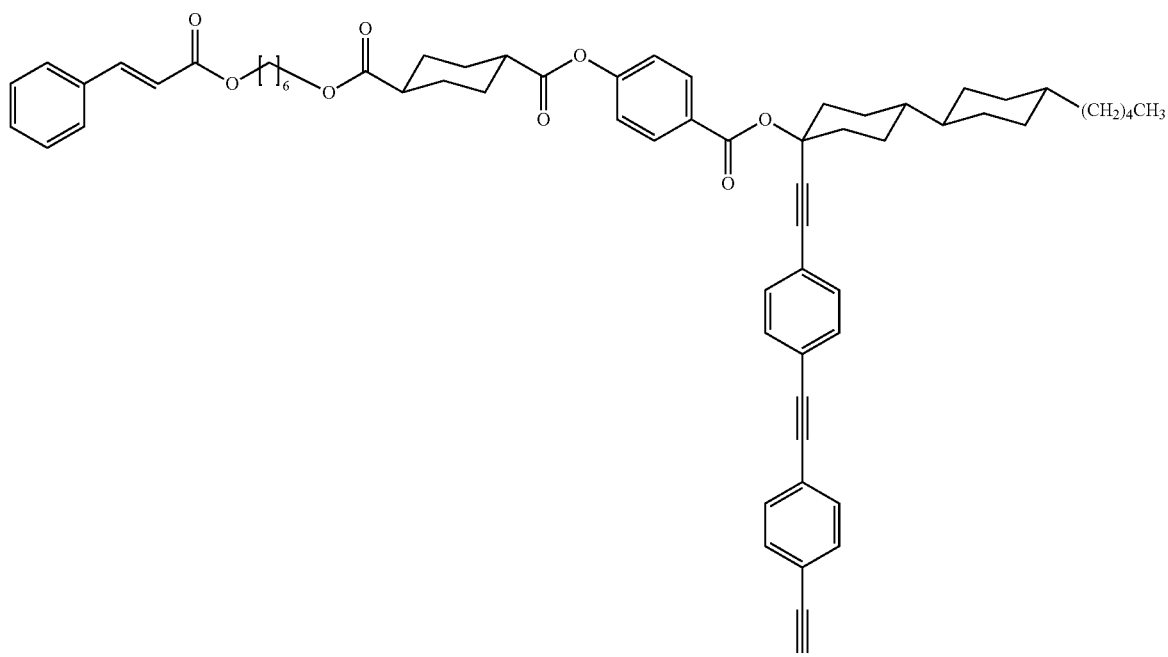

Compound RD-35 was synthesized according to the scheme shown in FIGS. 8a and 8b.

Synthesis of Compound 47-2

About 100 g of Compound 47-2 was obtained by the same method as the synthesis of Compound 12-1 of Example 1, except that Compound 38 of Example 16 was used instead of Compound 10 and Compound 46-2 [(1r,4r)-4-(((6-(cinnamoyloxy)hexyl)oxy)carbonyl)cyclohexanecarboxylic acid] was used instead of Compound 11-1.

Synthesis of Compound 48-2

About 70 g of Compound 48-2 was obtained by the same method as the synthesis of Compound 15-1 of Example 1, except that Compound 47-2 was used instead of Compound 14-1.

Synthesis of Compound RD-35

About 50 g of Compound RD-35 was obtained by the same method as the synthesis of Compound RD-01 of Example 1, except that Compound 48-2 was used instead of Compound 15-1.

The NMR spectrum of the obtained Compound RD-35 is as follows.

$^1$H NMR (CDCl$_3$, standard material TMS) δ(ppm): 8.04 (2H, d), 7.60 (2H, d), 7.56 (4H, d), 7.51 (4H, d), 7.48 (1H, d), 7.40 (4H, d), 7.33 (1H, t), 6.31 (1H, d), 4.13 (2H, t), 4.05 (1H, s), 3.97 (2H, t), 3.52 (1H, s), 1.60-1.12 (52H, m)

Example 36: Synthesis of Compound RD-36

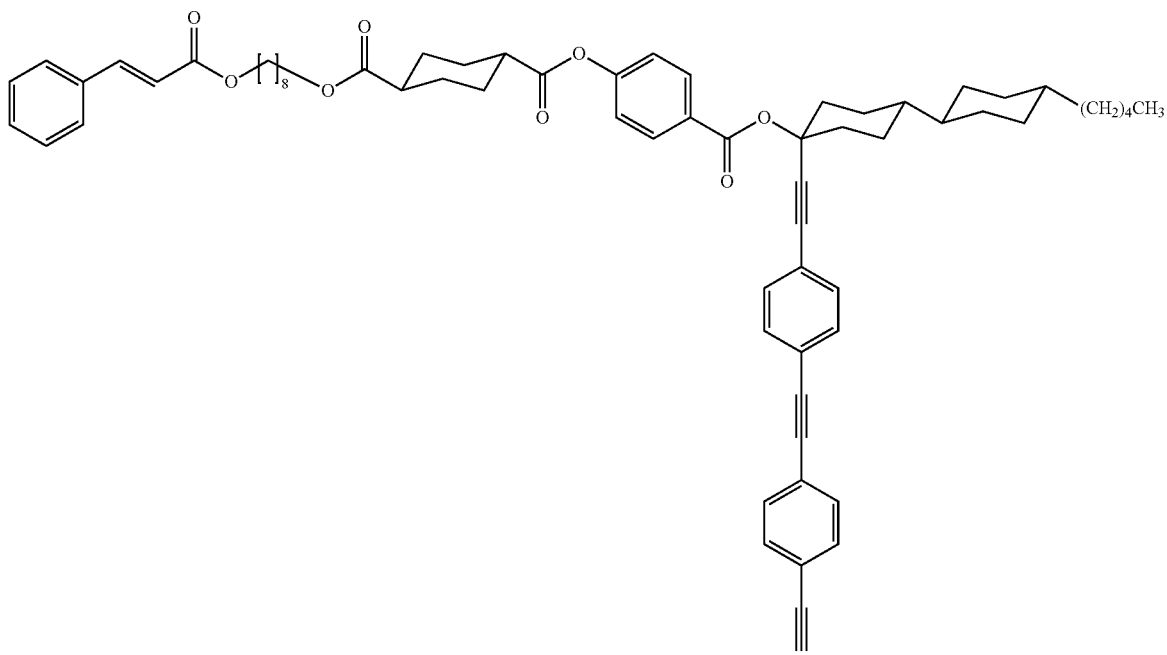

Compound RD-36 was synthesized according to the scheme shown in FIGS. 8a and 8b.

Synthesis of Compound 47-3

About 100 g of Compound 47-3 was obtained by the same method as the synthesis of Compound 12-1 of Example 1, except that Compound 38 of Example 16 was used instead of Compound 10 and Compound 46-3 [(1r,4r)-4-(((8-(cinnamoyloxy)octyl)oxy)carbonyl)cyclohexanecarboxylic acid] was used instead of Compound 11-1.

Synthesis of Compound 48-3

About 70 g of Compound 48-3 was obtained by the same method as the synthesis of Compound 15-1 of Example 1, except that Compound 47-3 was used instead of Compound 14-1.

Synthesis of Compound RD-36

About 50 g of Compound RD-36 was obtained by the same method as the synthesis of Compound RD-01 of Example 1, except that Compound 48-3 was used instead of Compound 15-1.

The NMR spectrum of the obtained Compound RD-36 is as follows.

$^1$H NMR (CDCl$_3$, standard material TMS) δ(ppm): 8.04 (2H, d), 7.60 (2H, d), 7.56 (4H, d), 7.51 (4H, d), 7.48 (1H, d), 7.40 (4H, d), 7.33 (1H, t), 6.31 (1H, d), 4.13 (2H, t), 4.05 (1H, s), 3.97 (2H, t), 3.52 (1H, s), 1.60-1.12 (56H, m)

Example 37: Synthesis of Compound RD-37

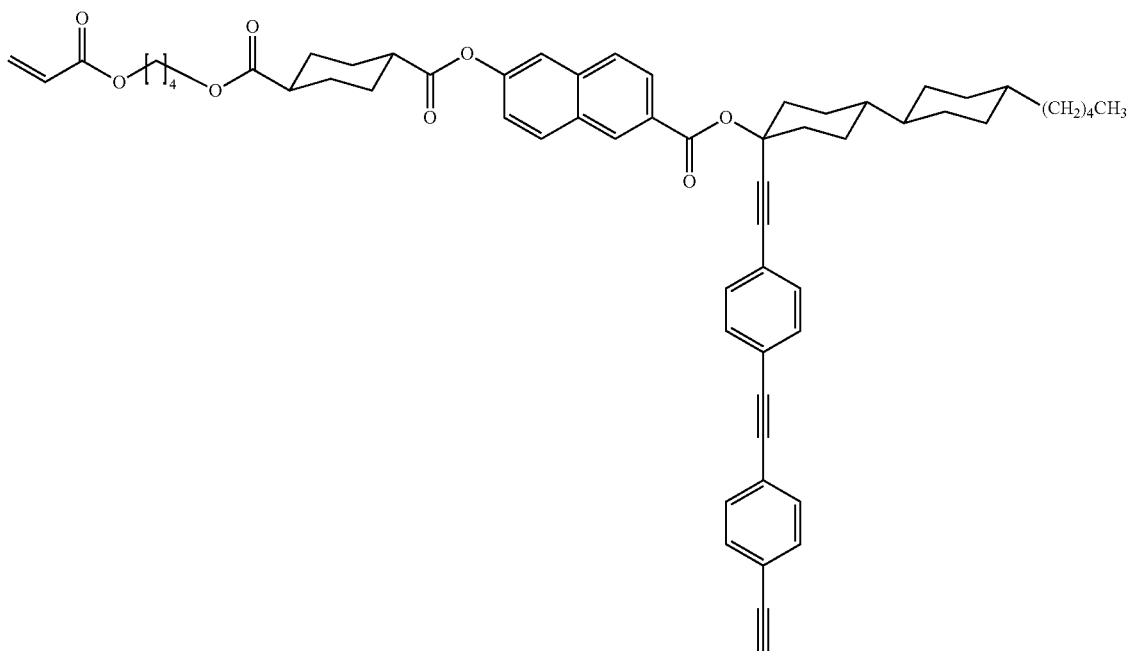

RD-37

Figure 9A:
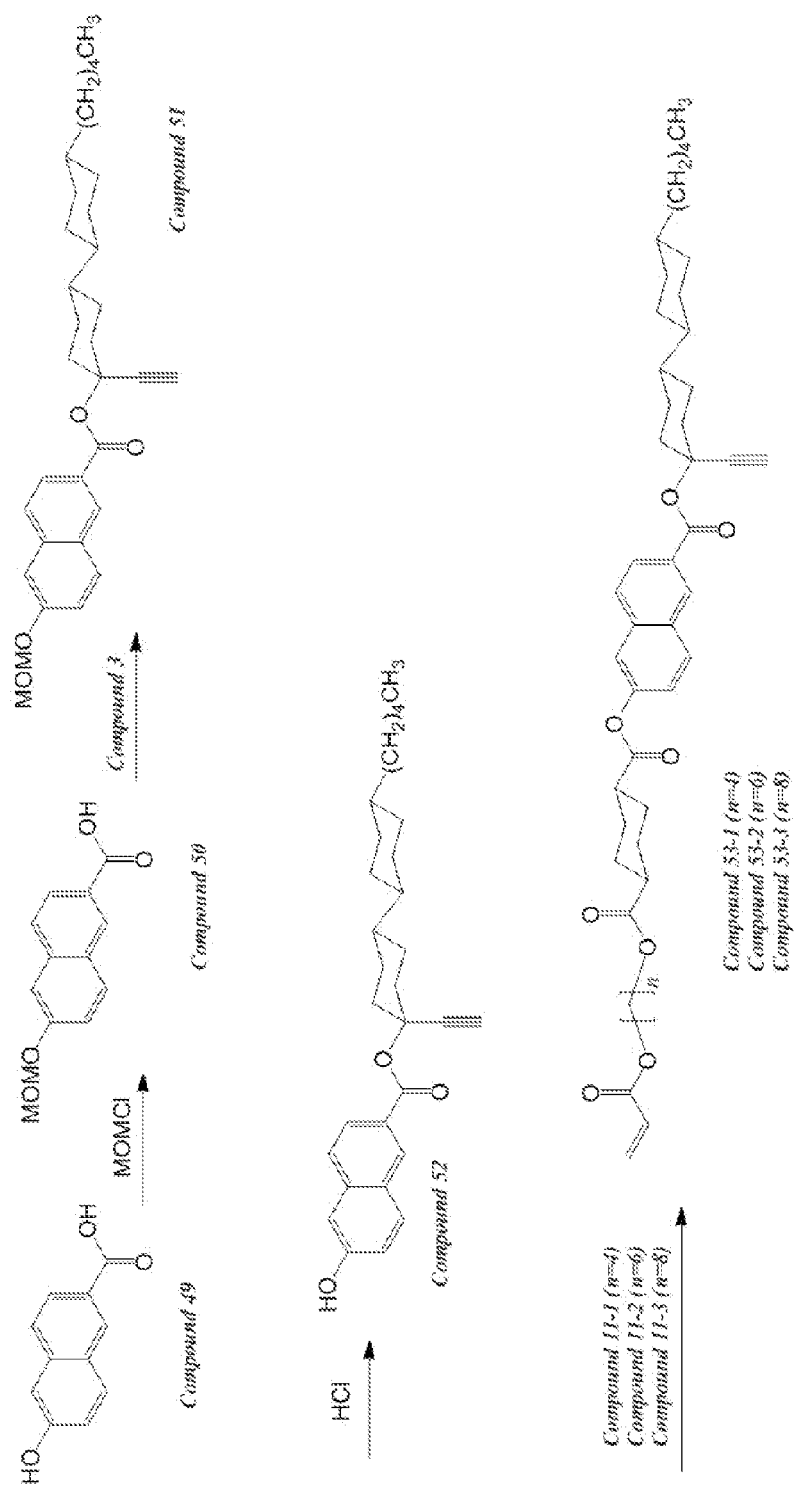
Figure 9B:
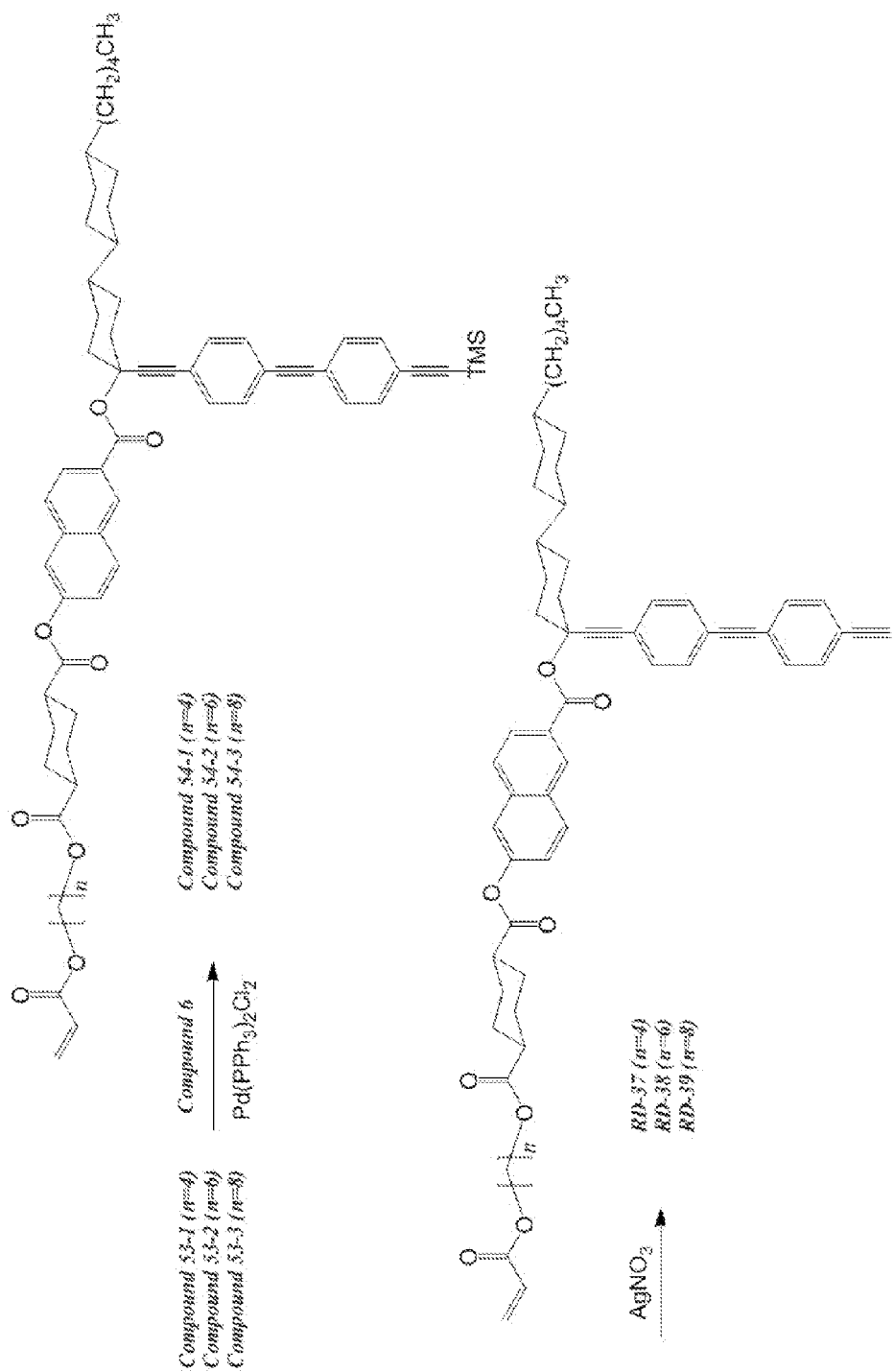

Compound RD-37 was synthesized according to the scheme shown in FIGS. 9a and 9b.

Synthesis of Compound 50

About 110 g of Compound 50 was obtained by the same method as the synthesis of Compound 8 of Example 1, except that Compound 49 (6-hydroxy-2-naphthoic acid) was used instead of Compound 7.

Synthesis of Compound 51

About 150 g of Compound 51 was obtained by the same method as the synthesis of Compound 9 of Example 1, except that Compound 50 was used instead of Compound 8.

Synthesis of Compound 52

About 80 g of Compound 52 was obtained by the same method as the synthesis of Compound 10 of Example 1, except that Compound 51 was used instead of Compound 9.

Synthesis of Compound 53-1

About 100 g of Compound 53-1 was obtained by the same method as the synthesis of Compound 12-1 of Example 1, except that Compound 52 was used instead of Compound 10.

Synthesis of Compound 54-1

About 30 g of Compound 54-1 was obtained by the same method as the synthesis of Compound 15-1 of Example 1, except that Compound 53-1 was used instead of Compound 14-1.

Synthesis of Compound RD-37

About 20 g of Compound RD-37 was obtained by the same method as the synthesis of Compound RD-01 of Example 1, except that Compound 54-1 was used instead of Compound 15-1.

The NMR spectrum of the obtained Compound RD-37 is as follows.

$^1$H NMR (CDCl$_3$, standard material TMS) δ(ppm): 8.68 (1H, s), 8.21 (1H, d), 8.18 (1H, d), 7.98 (1H, s), 7.97 (1H, d), 7.56 (4H, d), 7.51 (4H, d), 7.48 (1H, d), 6.27 (1H, d), 6.05 (1H, dd), 5.59 (1H, d), 4.13 (2H, t), 4.05 (1H, s), 3.97 (2H, t), 3.52 (1H, s), 1.60-1.12 (48H, m)

Example 38: Synthesis of Compound RD-38

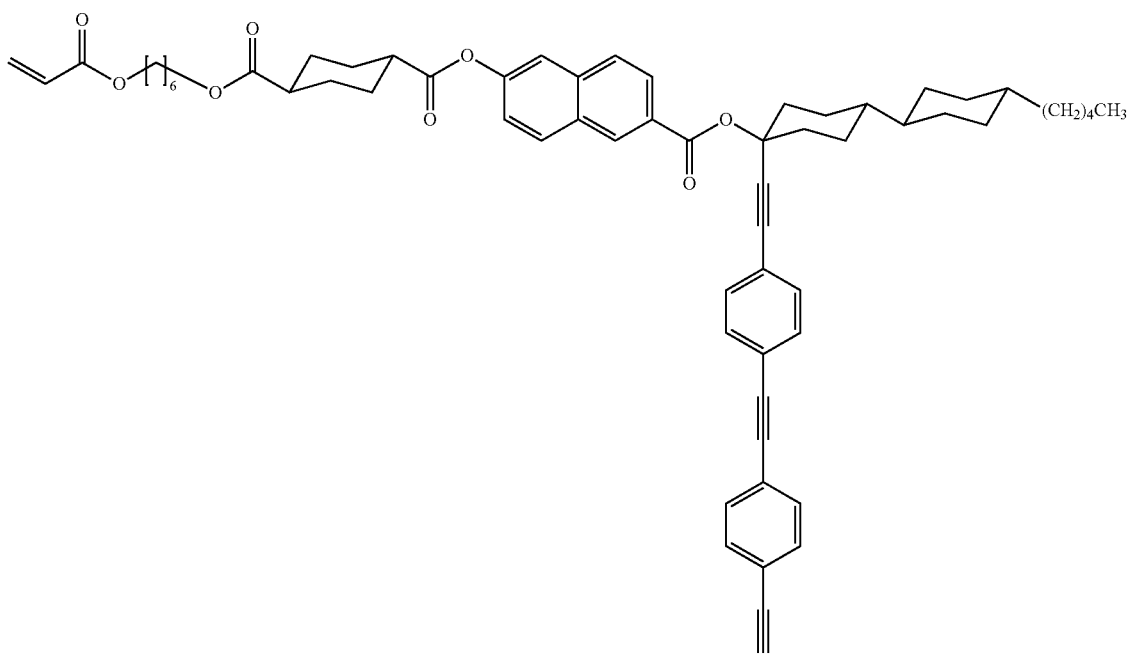

Compound RD-38 was synthesized according to the scheme shown in FIGS. 9a and 9b.

Synthesis of Compound 53-2

About 100 g of Compound 53-2 was obtained by the same method as the synthesis of Compound 12-1 of Example 1, except that Compound 52 was used instead of Compound 10 and Compound 11-2 [(1r,4r)-4-(((6-(acryloyloxy)hexyl)oxy)carbonyl)cyclohexanecarboxylic acid] was used instead of Compound 11-1.

Synthesis of Compound 54-2

About 70 g of Compound 54-2 was obtained by the same method as the synthesis of Compound 15-1 of Example 1, except that Compound 53-2 was used instead of Compound 14-1.

Synthesis of Compound RD-38

About 50 g of Compound RD-38 was obtained by the same method as the synthesis of Compound RD-01 of Example 1, except that Compound 54-2 was used instead of Compound 15-1.

The NMR spectrum of the obtained Compound RD-38 is as follows.

$^1$H NMR (CDCl$_3$, standard material TMS) δ(ppm): 8.68 (1H, s), 8.21 (1H, d), 8.18 (1H, d), 7.98 (1H, s), 7.97 (1H, d), 7.56 (4H, d), 7.51 (4H, d), 7.48 (1H, d), 6.27 (1H, d), 6.05 (1H, dd), 5.59 (1H, d), 4.13 (2H, t), 4.05 (1H, s), 3.97 (2H, t), 3.52 (1H, s), 1.60-1.12 (52H, m)

Example 39: Synthesis of Compound RD-39

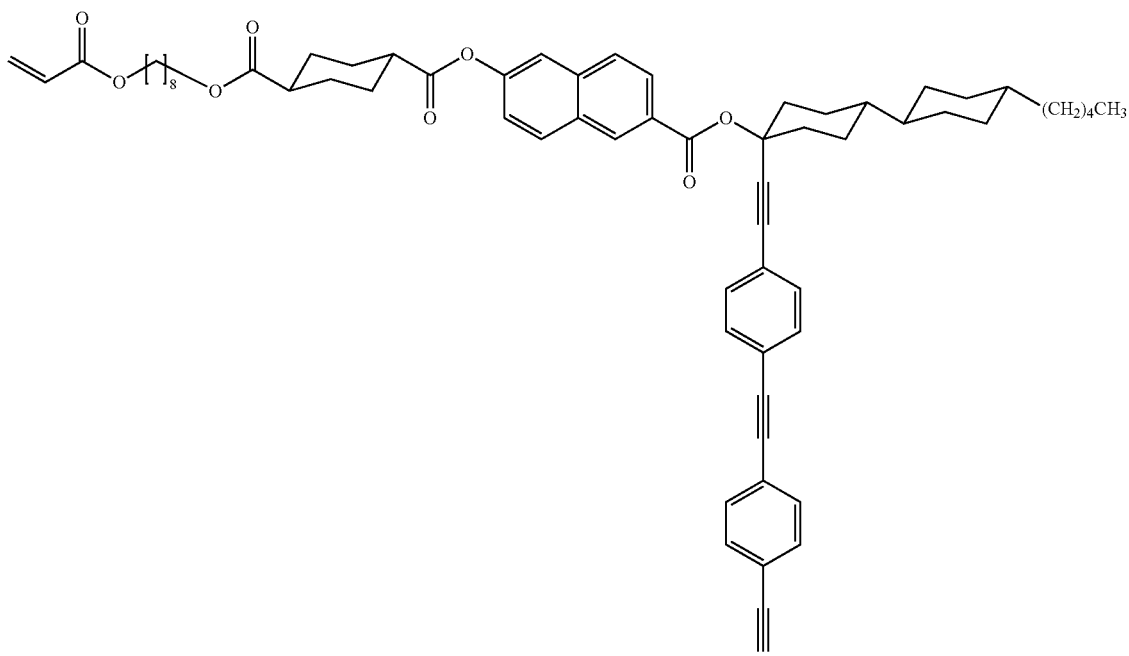

RD-39

Compound RD-39 was synthesized according to the scheme shown in FIGS. 9a and 9b.

Synthesis of Compound 53-3

About 100 g of Compound 53-3 was obtained by the same method as the synthesis of Compound 12-1 of Example 1, except that Compound 52 was used instead of Compound 10 and Compound 11-3 [(1r,4r)-4-(((8-(acryloyloxy)octyl)oxy)carbonyl)cyclohexanecarboxylic acid] was used instead of Compound 11-1.

Synthesis of Compound 54-3

About 70 g of Compound 54-3 was obtained by the same method as the synthesis of Compound 15-1 of Example 1, except that Compound 53-3 was used instead of Compound 14-1.

Synthesis of Compound RD-39

About 50 g of Compound RD-39 was obtained by the same method as the synthesis of Compound RD-01 of Example 1, except that Compound 54-3 was used instead of Compound 15-1.

The NMR spectrum of the obtained Compound RD-39 is as follows.

$^1$H NMR (CDCl$_3$, standard material TMS) δ(ppm): 8.68 (1H, s), 8.21 (1H, d), 8.18 (1H, d), 7.98 (1H, s), 7.97 (1H, d), 7.56 (4H, d), 7.51 (4H, d), 7.48 (1H, d), 6.27 (1H, d), 6.05 (1H, dd), 5.59 (1H, d), 4.13 (2H, t), 4.05 (1H, s), 3.97 (2H, t), 3.52 (1H, s), 1.60-1.12 (56H, m)

Example 40: Synthesis of Compound RD-40

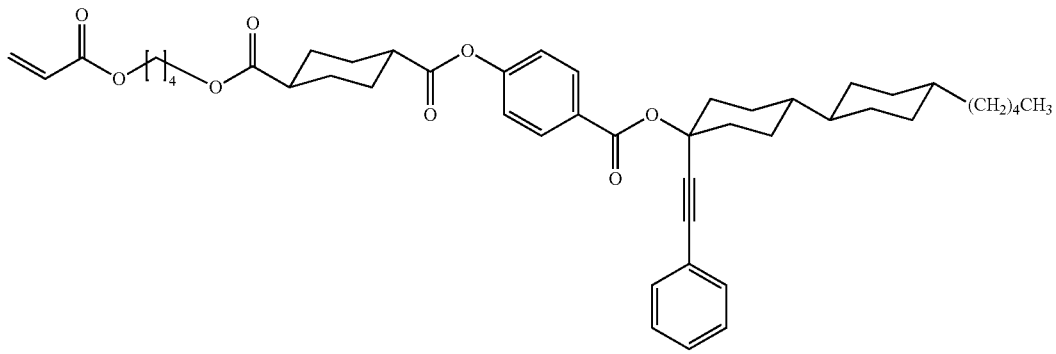

RD-40

Figure 10:
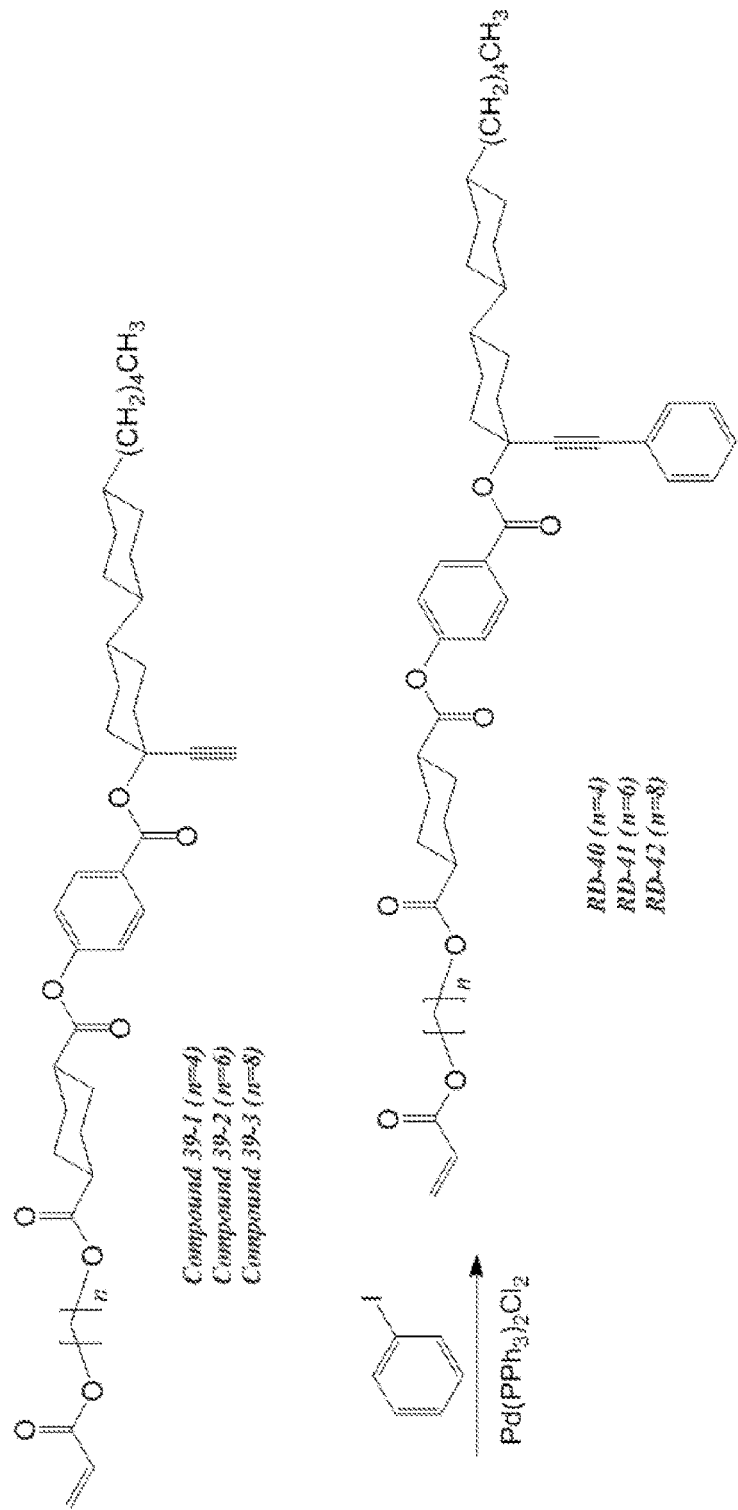

Compound RD-40 was synthesized according to the scheme shown in FIG. 10.

Namely, about 30 g of Compound RD-40 was obtained by the same method as the synthesis of Compound 15-1 of Example 1, except that Compound 39-1 of Example 16 was used instead of Compound 14-1 and about 10 g of iodobenzene was used instead of Compound 6.

The NMR spectrum of the obtained Compound RD-40 is as follows.

$^1$H NMR (CDCl$_3$, standard material TMS) δ(ppm): 8.04 (2H, d), 7.55 (2H, d), 7.43 (2H, d), 7.43 (2H, d), 7.40 (2H, d), 6.27 (1H, d), 6.05 (1H, dd), 5.59 (1H, d), 4.13 (2H, t), 3.97 (2H, t), 1.60-1.12 (48H, m)

Example 41: Synthesis of Compound RD-41

Compound RD-42 was synthesized according to the scheme shown in FIG. 10.

Namely, about 50 g of Compound RD-42 was obtained by the same method as the synthesis of Compound 15-1 of Example 1, except that Compound 39-3 of Example 18 was used instead of Compound 14-1 and about 10 g of iodobenzene was used instead of Compound 6.

The NMR spectrum of the obtained Compound RD-42 is as follows.

$^1$H NMR (CDCl$_3$, standard material TMS) δ(ppm): 8.04 (2H, d), 7.55 (2H, d), 7.43 (2H, d), 7.43 (2H, d), 7.40 (2H, d), 6.27 (1H, d), 6.05 (1H, dd), 5.59 (1H, d), 4.13 (2H, t), 3.97 (2H, t), 1.60-1.12 (56H, m)

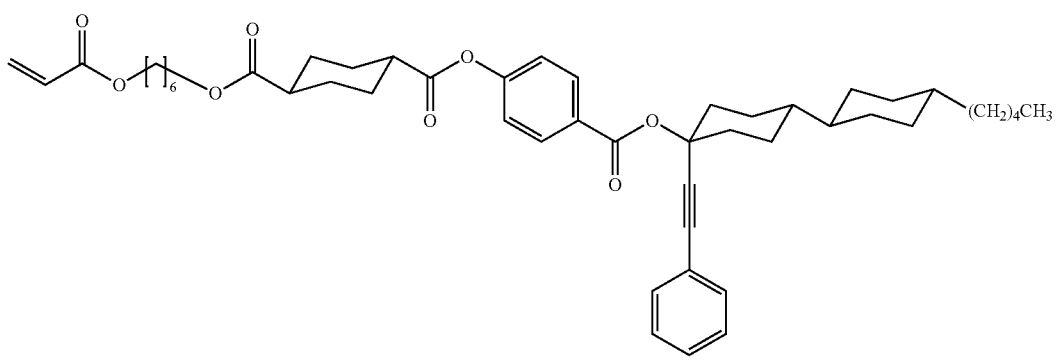

RD-41

Compound RD-41 was synthesized according to the scheme shown in FIG. 10.

Namely, about 50 g of Compound RD-41 was obtained by the same method as the synthesis of Compound 15-1 of Example 1, except that Compound 39-2 of Example 17 was used instead of Compound 14-1 and about 10 g of iodobenzene was used instead of Compound 6.

The NMR spectrum of the obtained Compound RD-41 is as follows.

$^1$H NMR (CDCl$_3$, standard material TMS) δ(ppm): 8.04 (2H, d), 7.55 (2H, d), 7.43 (2H, d), 7.43 (2H, d), 7.40 (2H, d), 6.27 (1H, d), 6.05 (1H, dd), 5.59 (1H, d), 4.13 (2H, t), 3.97 (2H, t), 1.60-1.12 (52H, m)

Example 42: Synthesis of Compound RD-42

Preparation Example 1

Preparation of Composition for Optical Elements

About 112.5 parts by weight of a mesogenic compound represented by the following Chemical Formula a, about 37.5 parts by weight of a mesogenic compound represented by the following Chemical Formula b, about 12.5 parts by weight of an initiator (Irgacure 907, Ciba-Geigy Co.), about 0.27 parts by weight of an antioxidant (Irganox 1076, Ciba-Geigy Co.), about 3.33 parts by weight of a fluorine-based surfactant (FC-171, 3M Co.), and about 1000 parts by weight of toluene were mixed with 100 parts by weight of Compound RD-18 of Example 18 for preparing the composition for optical elements (solid content: about 21 wt %).

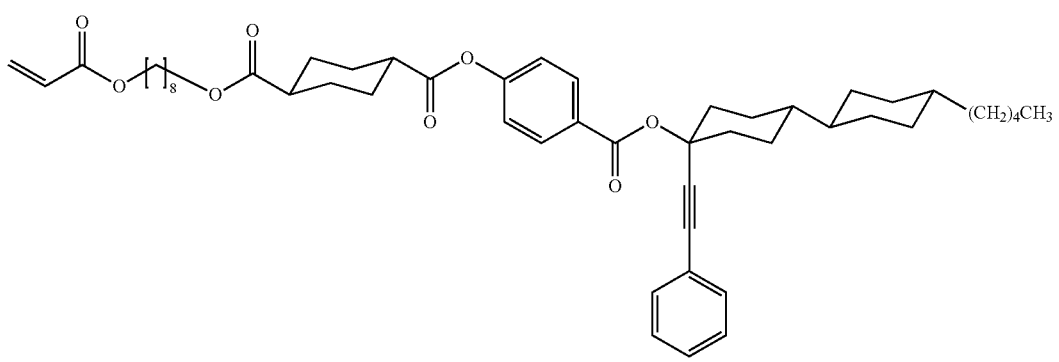

RD-42

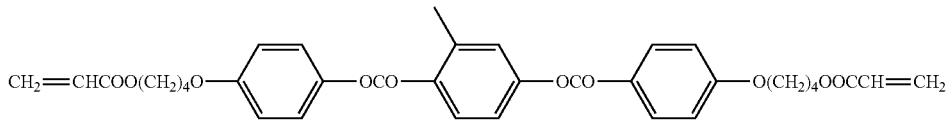

[Chemical Formula a]

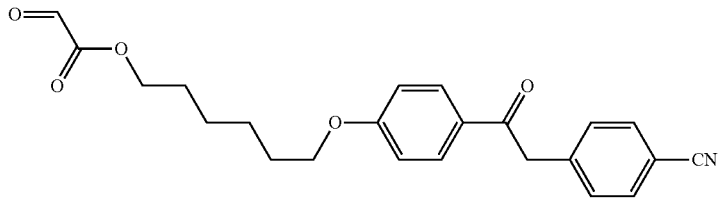

[Chemical Formula b]

Preparation of Retardation Film

Said composition was coated by a roll coating method on a TAC film on which a norbornene-based light alignment material had been coated, and dried for 2 min at about 80° C. in order to align the liquid crystal molecules. Subsequently, the retardation film was prepared by the method of exposing the film to a non-polarized UV originated from a high pressure mercury lamp of 200 mW/cm² for fixing the aligned state of the liquid crystal.

The quantitative retardation value of the prepared retardation film was measured by using Axoscan equipment (product of Axomatrix Co.). At this time, the thickness of the film was measured independently and the retardation value ($\Delta n \cdot d$) was obtained from the obtained value. As the result, $\Delta n \cdot d_{(450nm)}$, $\Delta n \cdot d_{(550nm)}$, and $\Delta n \cdot d_{(650nm)}$ were measured as 103, 110, and 114, respectively. Therefore, the value of $\Delta n_{(450nm)}/\Delta n_{(550nm)}$ was 0.94 and the value of $\Delta n(650\ nm)/\Delta n(550\ nm)$ was 1.04, and thus it was recognized that the film satisfied the conditions according to Equations I and II disclosed above.

Preparation Example 2

Preparation of Composition for Optical Elements

About 112.5 parts by weight of a mesogenic compound represented by Chemical Formula a, about 62.5 parts by weight of a mesogenic compound represented by Chemical Formula b, about 12.5 parts by weight of an initiator (Irgacure 907, Ciba-Geigy Co.), about 0.27 parts by weight of an antioxidant (Irganox 1076, Ciba-Geigy Co.), about 3.33 parts by weight of a fluorine-based surfactant (FC-171, 3M Co.), and about 1000 parts by weight of toluene were mixed with 75 parts by weight of Compound RD-18 of Example 18 for preparing the composition for optical elements (solid content: about 21 wt %).

Preparation of Retardation Film

Said composition was coated by a roll coating method on a TAC film on which a norbornene-based light alignment material had been coated, and dried for 2 min at about 80° C. in order to align the liquid crystal molecules. Subsequently, the retardation film was prepared by the method of exposing the film to non-polarized UV originated from a high pressure mercury lamp of 200 mW/cm² for fixing the aligned state of the liquid crystal.

The quantitative retardation value of the prepared retardation film was measured by using Axoscan equipment (product of Axomatrix Co.). At this time, the thickness of the film was measured independently and the retardation value ($\Delta n \cdot d$) was obtained from the obtained value. As the result, $\Delta n \cdot d_{(450\ nm)}$, $\Delta n \cdot d_{(550\ nm)}$, and $\Delta n \cdot d_{(650\ nm)}$ were measured as 115, 120, and 124, respectively. Therefore, the value of $\Delta n_{(450\ nm)}/\Delta n_{(550\ nm)}$ was 0.96 and the value of $\Delta n_{(650\ nm)}/\Delta n_{(550\ nm)}$ was 1.03, and thus it was recognized that the film satisfied the conditions according to Equations I and II disclosed above.

Preparation Example 3

Preparation of Composition for Optical Elements

About 112.5 parts by weight of a mesogenic compound represented by Chemical Formula a, about 37.5 parts by weight of a mesogenic compound represented by Chemical Formula b, about 12.5 parts by weight of an initiator (Irgacure 907, Ciba-Geigy Co.), about 0.27 parts by weight of an antioxidant (Irganox 1076, Ciba-Geigy Co.), about 3.33 parts by weight of a fluorine-based surfactant (FC-171, 3M Co.), and about 1000 parts by weight of toluene were mixed with 100 parts by weight of Compound RD-40 of Example 40 for preparing the composition for optical elements (solid content: about 21 wt %).

Preparation of Retardation Film

Said composition was coated by a roll coating method on a TAC film on which a norbornene-based light alignment material had been coated, and dried for 2 min at about 80° C. in order to align the liquid crystal molecules. Subsequently, the retardation film was prepared by the method of exposing the film to non-polarized UV originated from a high pressure mercury lamp of 200 mW/cm² for fixing the aligned state of the liquid crystal.

The quantitative retardation value of the prepared retardation film was measured by using Axoscan equipment (product of Axomatrix Co.). At this time, the thickness of the film was measured independently and the retardation value ($\Delta n \cdot d$) was obtained from the obtained value. As the result, $\Delta n \cdot d_{(450\ nm)}$, $\Delta n \cdot d_{(550\ nm)}$, and $\Delta n \cdot d_{(650\ nm)}$ were measured as 110, 113, and 115, respectively. Therefore, the value of $\Delta n_{450\ nm}/\Delta n_{(550\ nm)}$ was 0.97 and the value of $\Delta n_{(650\ nm)}/\Delta n(550\ nm)$ was 1.02, and thus it was recognized that the film satisfied the conditions according to Equations I and II disclosed above.

Preparation Example 4

Preparation of Composition for Optical Elements

About 112.5 parts by weight of a mesogenic compound represented by Chemical Formula a, about 62.5 parts by weight of a mesogenic compound represented by Chemical Formula b, about 12.5 parts by weight of an initiator (Irgacure 907, Ciba-Geigy Co.), about 0.27 parts by weight of an antioxidant (Irganox 1076, Ciba-Geigy Co.), about 3.33 parts by weight of a fluorine-based surfactant (FC-171, 3M Co.), and about 1000 parts by weight of toluene were mixed with 75 parts by weight of Compound RD-40 of Example 40 for preparing the composition for optical elements (solid content: about 21 wt %).

Preparation of Retardation Film

Said composition was coated by a roll coating method on a TAC film on which a norbornene-based light alignment material had been coated, and dried for 2 min at about 80° C. in order to align the liquid crystal molecules. Subsequently, the retardation film was prepared by the method of exposing the film to non-polarized UV originated from a high pressure mercury lamp of 200 mW/cm² for fixing the aligned state of the liquid crystal.

The quantitative retardation value of the prepared retardation film was measured by using Axoscan equipment (product of Axomatrix Co.). At this time, the thickness of the film was measured independently and the retardation value ($\Delta n \cdot d$) was obtained from the obtained value. As the result, $\Delta n \cdot d_{(450nm)}$, $\Delta n \cdot d_{(550\ nm)}$, and $\Delta n \cdot d_{(650\ nm)}$ were measured as 125, 126, and 127, respectively. Therefore, the value of $\Delta n_{(450\ nm)}/\Delta n_{(550\ nm)}$ was 0.99 and the value of $\Delta n_{(650\ nm)}/\Delta n_{(550\ nm)}$ was 1.01, and thus it was recognized that the film satisfied the conditions according to Equations I and II disclosed above.

Comparative Preparation Example 1

Preparation of Composition for Optical Elements

About 56.25 parts by weight of a mesogenic compound represented by Chemical Formula b, about 7.8 parts by weight of an initiator (Irgacure 907, Ciba-Geigy Co.), about 0.17 parts by weight of an antioxidant (Irganox 1076, Ciba-Geigy Co.), about 2.08 parts by weight of a fluorine-based surfactant (FC-171, 3M Co.), and about 625 parts by weight of toluene were mixed with about 100 parts by weight of a mesogenic compound represented by Chemical Formula a for preparing the composition for optical elements (solid content: about 21 wt %).

Preparation of Retardation Film

Said composition was coated by a roll coating method on a TAC film on which a norbornene-based light alignment material had been coated, and dried for 2 min at about 80° C. in order to align the liquid crystal molecules. Subsequently, the retardation film was prepared by the method of exposing the film to non-polarized UV originated from a high pressure mercury lamp of 200 mW/cm² for fixing the aligned state of the liquid crystal.

The quantitative retardation value of the prepared retardation film was measured by using Axoscan equipment (product of Axomatrix Co.). At this time, the thickness of the film was measured independently and the retardation value ($\Delta n \cdot d$) was obtained from the obtained value. As the result, $\Delta n \cdot d_{(450\ nm)}$, $\Delta n \cdot d_{(550\ nm)}$, and $\Delta n \cdot d_{(650\ nm)}$ were measured as 225, 210, and 203, respectively. Therefore, the value of $\Delta n_{(450\ nm)}/\Delta n_{(550\ nm)}$ was 1.07 and the value of $\Delta n_{(650\ nm)}/\Delta n(550\ nm)$ was 0.96, and thus it was recognized that the film did not satisfy the conditions according to Equations I and II disclosed above.

The invention claimed is:

1. A reverse wavelength dispersion compound having Chemical Formula 1:

$$L^1 + D^1-G^1 +_m E^1-A-E^2 + G^2-D^2 +_n L^2 \quad \text{[Chemical Formula 1]}$$

wherein, in Chemical Formula 1,

A is a $C_6$-$C_{20}$ aromatic group;

$E^1$, $E^2$, $D^1$, and $D^2$ are independently a single bond, —COO—, or —OCO—;

$L^1$ and $L^2$ are independently —H, $C_1$-$C_{20}$ alkyl or —$S_p$—P, wherein at least one of said $L^1$ and $L^2$ is —$S_p$—P, said P is $CH_2$=CH—COO— or $CH_2$=CH—OCO—, said $S_p$ is a $C_1$-$C_{20}$ alkylene;

m and n are independently an integer of 1 to 5, wherein if said m or n is 2 or more, each repeating unit of -($D^1$-$G^1$)- or -($G^2$-$D^2$)- repeating twice or more may be the same as or different from each other; and $G^1$ and $G^2$ are independently a $C_5$-$C_8$ non-aromatic carbocyclic group or a $C_6$-$C_{20}$ aromatic group, wherein at least one of said $G^1$ and $G^2$ is the carbocyclic group and any one of hydrogens included in the carbocyclic group is substituted by the group represented by the following Chemical Formula 2:

$$* + Q^1 +_p B^1 \quad \text{[Chemical Formula 2]}$$

wherein, in Chemical Formula 2, p is an integer of 1 to 10, wherein if said p is 2 or more, each repeating unit of -($Q^1$)- repeating twice or more may be the same as or different from each other, -($Q^1$)- is

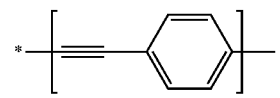

and $B^1$ is —H or a $C_2$-$C_6$ alkynyl group.

2. The reverse wavelength dispersion compound according to claim 1, wherein $G^1$, and $G^2$ of Chemical Formula 1 are independently a cyclohexane ring, a cyclohexene ring, a benzene ring, a naphthalene ring, or a phenanthrene ring; and at least one of said $G^1$ and $G^2$ is a cyclohexane ring or a cyclohexene ring, and wherein A of Chemical Formula 1 is a benzene ring, a naphthalene ring, or a phenanthrene ring.

3. An optically anisotropic film includes the reverse wavelength dispersion compound according to claim 1 and satisfies the following Equations I and II:

$$\Delta n_{(450\ nm)}/\Delta n_{(550\ nm)} < 1.0 \quad \text{(Equation I)}$$

$$\Delta n_{(650\ nm)}/\Delta n_{(550\ nm)} > 1.0 \quad \text{(Equation II)}$$

wherein, in Equations I and II, $\Delta n(\lambda)$ means a specific birefringent index at wavelength $\lambda$.

* * * * *